United States Patent [19]

Mueller et al.

[11] Patent Number: 5,536,734

[45] Date of Patent: Jul. 16, 1996

[54] DIHYDROPYRAN DERIVATIVES AND CROP PROTECTION AGENTS CONTAINING THEM

[75] Inventors: Bernd Mueller, Frankenthal; Siegbert Brand, Birkenheide; Hubert Sauter, Mannheim; Franz Roehl, Ludwigshafen; Eberhard Ammermann, Heppenheim; Gisela Lorenz, Neustadt, all of Germany

[73] Assignee: BASF Aktiengesellschaft, Ludwigshafen, Germany

[21] Appl. No.: 263,414

[22] Filed: Jun. 21, 1994

Related U.S. Application Data

[63] Continuation of Ser. No. 946,651, Sep. 18, 1992, abandoned.

[30] Foreign Application Priority Data

Sep. 20, 1991 [DE] Germany ............... 41 31 311.9

[51] Int. Cl.[6] ................. C07D 309/20; A61K 31/35
[52] U.S. Cl. .................. 514/336; 514/374; 514/451; 514/459; 546/210; 548/236; 549/426; 549/427
[58] Field of Search .................. 549/426, 427; 514/459, 451, 374, 336; 548/236; 546/210

[56] References Cited

U.S. PATENT DOCUMENTS

| 3,862,325 | 1/1975 | Plowman .................. 514/451 |
| 5,185,342 | 2/1993 | Hayase et al. ............. 514/459 |

FOREIGN PATENT DOCUMENTS 1194526  6/1970  United Kingdom .

OTHER PUBLICATIONS

The Pesticide Manual, vol. 8, C. Worthing, ed., p. 902, "Superseded Compounds." (1989).

Journal of Organic Chemistry, vol. 39, No. 23, pp. 3432–3433, Nov. 15, 1974, S. S. Hall, et al., "The Chemistry of 2–Alkoxy–3,4–Dihydro–2H–Pyrans. II. Addition of Dimethyl Acetylenedicarboxylate to 2–Alkoxy–6–Methyl–3, 4–Dihydro–2H–Pyrans".

Tetrahedron Letters, vol. 32, No. 24, pp. 2779–2782, Jun. 10, 1991, Han–Young Kang, et al., "Intramolecular[3+2] Nitrone–Alkyne Cycloaddition".

Tetrahedron Letters, vol. 31, No. 42, pp. 6077–6080, Oct. 8, 1990, D. Macleod, et al., "The Pd(0)–Catalysed Coupling Reactins of 2–(Tri–N–Butylstannyl)–3,4–Dihydrofuran and –5,6–Dihydropyran".

Synthesis, No. 8, pp. 610–613, Aug. 1979, A. Lebouc, et al., "New Synthesis of Dihydropyranylcarbinols, Dihydropyranyl Ketones, and 1–Dihydropyranylalkyl Carboxylates From Lithiated 3,4–Dihydro–2H–Pyrans".

Tetrahedron, vol. 46, No. 5, pp. 1625–1652, 1990, H. Booth, et al., "Experimental Studies of the Anomeric Effect. Part III.[1]Rotameric Preferences About the Exo–Cyclic $C_2$–X Bond in Equatorial and Axial 2–Methoxy–And 2–Methylamino–Tetrahydropyrans".

Tetrahedron Letters, vol. 29, No. 19, pp. 2353–2356, 1988, P. Kocienski, et al., "A Stereoselective Synthesis of Tri–Substituted Alkenes. The Nickel–Catalysed Coupling of Grignard Reagents With 6–Alkyl–3,4–Dihydro–2H–Pyrans".

Chemical Abstracts, vol. 111, No. 3, No. 23340k, Jul. 17, 1989, M. G. Voronkov, et al., "Regioselective Addition of Dichlorocarbene to 2–Vinyloxy–3,4–Dihydropyrans".

Chemical Abstracts, vol. 107, No. 8, No. 59586b, Aug. 24, 1987, J. Y. Lee, et al., "Synthesis of Alternating Head–to––Head Copolymers of Vinyl Ketones and Vinyl Ethers, and Their Properties. Ring–Opening Polymerization of 2,3, 6–Trisubstituted–3,4–Dihydro–2H–Pyrans".

Tetrahedron, vol. 42, No. 15, pp. 4333–4342, 1986, S. V. Ley, et al., "Alkylation Reactions of Anions Derived Form 2–Benzenesulphonyl Tetrahydropyran and Their Application to Spiroketal Synthesis".

Tetrahedron, vol. 37, No. 23, pp. 3997–4006, 1981, R. K. Boeckman, Jr., et al., "Cyclic Vinyl Ether Carbanions—II. Preparation and Applications to the Synthesis of Carbonyl Compounds".

Primary Examiner—Johann Richter
Assistant Examiner—John D. Peabody, III
Attorney, Agent, or Firm—Oblon, Spivak, McClelland, Maier & Neustadt

[57] ABSTRACT

Crop protection agents contain dihydropyrans of the formula

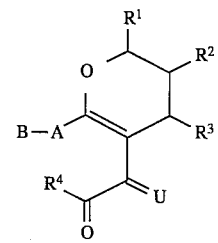

wherein the variable substituents are defined in the specification.

6 Claims, No Drawings

DIHYDROPYRAN DERIVATIVES AND CROP PROTECTION AGENTS CONTAINING THEM

This application is a continuation of application Ser. No. 07/946,651, filed on Sep. 18, 1992, now abandoned.

The present invention relates to dihydropyran derivatives and their use as crop protection agents, in particular for controlling fungi; insects, nematodes and mites.

It is known that dihydropyran derivatives, for example pyracarbolide (3,4-dihydro-6-methyl-2H-pyran-5-carboxanilide), can be used as fungicides (The Pesticide Manual, Eighth Edition, page 902, British Crop Protection Council). However, their biological action is unsatisfactory.

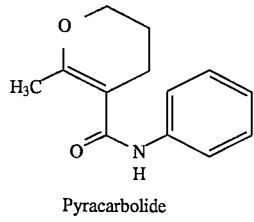

Pyracarbolide

We have found, surprisingly, that dihydropyran derivatives of the formula I

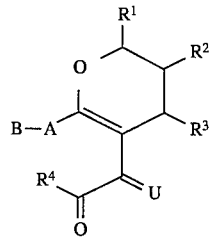

where U is $CH-OR^5$, $=CH-SR^5$, $=CH_2$, $=CH-R^5$, $=CH-$Halogen or $=N-OR^5$, A is a single bond or $-CHR^6-$, $-(CHR^7-CHR^6)_n-$, $-(CR^{21}=CR^{20})_m-CR^7=CR^6-$, $-C\equiv C-$, $-O-CHR^6-$, $-S-CHR^6-$, $-NR^{18}-CHR^6-$, $C(=O)-O-CHR^6-$ or $-R^{19}C=N-O-CHR^6-$, B is H or alkyl, alkenyl, alkynyl, cycloalkyl, aryl, hetaryl, heterocyclyl or cycloalkenyl, each of which is unsubstituted or substituted, $R^1$ is H, $O-R^8$ or unsubstituted or substituted $O$—aryl, $R^2$ is $R^9$ or unsubstituted or substituted aryl, $R^3$ is $R^{10}$ or unsubstituted or substituted aryl and, where $R^1$ and $R^2$ are each H, $R^3$ may additionally be $-CH(R^{11})-OR^{12}$, $-CO_2R^{12}$, $-CO-NR^{12}R^{13}$ or $-CH(R^{11})-CH(R^{14})-B$, and $R^4$ is $O-R^{15}$, $NR^{16}R^{17}$ or $R^{25}$, n is 1, 2 or 3, m is 0 or 1, $R^5$, $R^8$, $R^{12}$, $R^{13}$, $R^{15}$, $R^{18}$ and $R^{25}$ are each unsubstituted-or substituted straight-chain or branched $C_1$-$C_8$-alkyl, unsubstituted or substituted straight-chain or branched $C_2$-$C_8$-alkenyl, unsubstituted or substituted straight-chain or branched $C_2$-$C_8$-alkynyl or unsubstituted or substituted $C_3$-$C_{10}$-cycloalkyl, $R^6$, $R^7$, $R^{11}$, $R^{14}$, $R^{16}$, $R^{17}$, $R^{20}$ and $R^{21}$ are each hydrogen or have the same meanings as $R^5$, $R^{19}$ is hydrogen, cyano, unsubstituted or substituted straight-chain or branched $C_1$-$C_8$-alkyl or unsubstituted or substituted $C_3$-$C_{10}$-cycloalkyl, $R^9$ and $R^{10}$ are each hydrogen, unsubstituted or substituted straight-chain or branched $C_1$-$C_8$-alkyl, unsubstituted or substituted straight-chain or branched $C_2$-$C_8$-alkynyl or unsubstituted or substituted $C_3$-$C_{10}$-cycloalkyl, and plant-tolerated acid adducts or base adducts thereof not only have high fungitoxic, insecticidal, nematicidal or acaricidal activity but also are very well tolerated by plants.

The dihydropyran of formula (I) can, alternatively, be defined wherein:

U is $=CH-OR^5$, $=CH-SR^5$, $=CH_2$, $=CH-R^5$, $=CH-X$ or $=N-OR^5$, wherein $R^5$ is unsubstituted or substituted straight-chain or branched $C_{1-8}$-alkyl, unsubstituted or substituted straight-chain or branched $C_{2-8}$-alkenyl, unsubstituted or substituted straight-chain or branched $C_{2-8}$-alkynyl, or unsubstituted or substituted $C_{3-10}$-cycloalkyl, and wherein X is a halogen A is a single bond, $-CHR^6-$, $-(CHR^6-CHR^6)_n-$, $-(CR^6=CR^6)_m-CR^6=CR^6-$, $-C\equiv C-$, $-O-CHR^6-$, $-S-CHR^6$, $-NR^5-CHR^6-$, $-C(=O)-O-CHR^6-$, or $-R^{19}C=N-O-CHR^6-$, wherein $R^5$ is as above defined, $R^6$, independently, is hydrogen, unsubstituted or substituted straight-chain or branched $C_{1-8}$-alkyl, unsubstituted or substituted straight-chain or branched $C_{2-8}$-alkenyl, unsubstituted or substituted straight-chain or branched $C_{2-8}$-alkynyl, or unsubstituted or substituted $C_{3-10}$-cycloalkyl, $R^{19}$ is hydrogen, cyano, unsubstituted or substituted straight-chain or branched $C_{1-8}$-alkyl, or unsubstituted or substituted $C_{3-10}$-cycloalkyl, and wherein n is 1, 2, or 3, and wherein m is 0 or 1;

B is hydrogen, or alkyl, alkenyl, alkynyl, cycloalkyl, aryl, hetaryl, heterocyclyl or cyloalkenyl, each of which is substituted or unsubstituted;

$R^1$ is hydrogen, $-O-R^5$, or unsubstituted or substituted $-O$—aryl, wherein $R^5$ is as above defined;

$R^2$ is unsubstituted or substituted aryl, hydrogen, unsubstituted or substituted straight-chain or branched $C_{1-8}$-alkyl, unsubstituted or substituted straight-chain or branched $C_{2-8}$-alkynyl, or unsubstituted or substituted $C_{3-10}$-cycloalkyl;

$R^3$ is unsubstituted or substituted aryl, hydrogen, unsubstituted or substituted straight-chain or branched $C_{1-8}$-alkyl, unsubstituted or substituted straight-chain or branched $C_{2-8}$-alkenyl, or unsubstituted or substituted $C_{3-10}$-cycloalkyl, and when $R^1$ and $R^2$ are each hydrogen, $R^3$ may additionally be $-CH(R^6)-OR^5$, $-CO_2R^5$, $-CO-NR^5R^5$, or $-CH(R^6)-CH(R^6)-B$, wherein B, $R^5$ and $R^6$, independently, are as defined above; and $R^4$ is $-O-R^5$, $-NR^6R^6$, or $-R^5$, wherein $R^5$ and $R^6$, independently, are as above defined.

Acids for acid adducts are, for example, mineral acids, for example hydrochloric acid, hydrobromic acid, phosphoric acid, sulfuric acid or nitric acid, or carboxylic acids, such as formic acid, acetic acid, oxalic acid, malonic acid, lactic acid, malic acid, succinic acid, tartaric acid, citric acid or salicylic acid, or sulfonic acids, such as p-toluenesulfonic acid or dodecylbenzenesulfonic acid, as well as proton-acidic compounds generally, for example saccharin.

Bases for base adducts are, for example, potassium hydroxide, potassium carbonate, sodium hydroxide, sodium carbonate and ammonium hydroxide.

The invention relates both to the dihydropyran derivates as such and to their acid adducts and base adducts. The acid adducts and base adducts are prepared by dissolving a dihydropyran derivative in an organic solvent, mixing the solution with the acid or the base and evaporating off the solvent.

The novel compounds of the formula I can be obtained in the preparation in the form of mixtures of stereoisomers (E/Z isomers, diastereomers or enantiomers), which can be separated into the individual components in a conventional manner, for example by crystallization or chromatography. Both the individual isomers and mixtures thereof can be used as fungicides, nematicides, acaricides or insecticides and form the subject of the present invention.

Particularly if the group U can occur in the form of syn/anti isomers, the present invention also relates to the syn and the anti isomers.

The abovementioned alkyl radicals are of 1 to 10 carbon atoms and may be substituted as desired, for example by 1–4 identical or different substituents $R^{22}$.

The abovementioned alkenyl radicals are of 2–10 carbon atoms and may be substituted as desired, for example by 1–4 identical or different substituents $R^{22}$.

The abovementioned alkynyl radicals are of 2–10 carbon atoms and may be substituted as desired, for example by 1–4 identical or different substituents $R^{22}$.

The abovementioned cycloalkyl radicals are of 3–10 carbon atoms and may be substituted as desired, for example by 1–4 identical or different substituents $R^{22}$.

The abovementioned aryl radicals are of 6, 10 or 14 carbon atoms and may be substituted as desired, for example by 1–4 identical or different substituents $R^{22}$.

The abovementioned hetaryl radicals are of 5–14 ring atoms, including 1–4 hetero atoms selected from the group consisting of N, O and S, and may be substituted as desired, for example by 1–4 identical or different substituents $R^{22}$.

The abovementioned heterocyclyl radicals are of 5–14 ring atoms, including 1–4 hetero atoms selected from the group consisting of N, O and S, are saturated or partially unsaturated and may be substituted as desired, for example by 1–4 identical or different substituents $R^{22}$.

The abovementioned cycloalkenyl radicals are of 5–14 carbon atoms and may be substituted as desired, for example by 1–4 identical or different substituents $R^{22}$.

Two adjacent substituents $R^{22}$, together with the carbon atoms of which they are substituents, may form a carbocyclic hydrogenated, partially unsaturated or aromatic ring of 3–14 carbon atoms or a heterocyclic hydrogenated, partially unsaturated or heteroaromatic ring of 3–14 ring atoms, including 1–4 hetero atoms selected from the group consisting of N, O and S.

$R^{22}$ may be substituted as desired, for example by 1–4 identical or different substituents $R^{24}$, and is preferably hydrogen, halogen, cyano, nitro, haloalkyl, $R^{23}$, $R^{23}$—O—, $R^{23}$—O—N=, $R^{23}$—O—C(=O) —, —$CONR^{12}R^{13}$—, $R^{23}$—S—, $R^{23}$—N($R^{12}$)—, $R^{23}$—CO—, $R^{23}$—SO—, $R^{23}$—S(O)$_2$— or $R^{23}$—S(=O)—O—.

$R^{23}$ is, for example, hydrogen or alkyl, alkenyl, alkynyl, cycloalkyl, aryl, hetaryl or heterocyclyl or cycloalkenyl each of which is unsubstituted or substituted.

$R^{24}$ is, for example, hydrogen, halogen, cyano, nitro, haloalkyl, alkyl, haloalkoxy, alkenyl, alkynyl, cycloalkyl, aryl, hetaryl, heterocyclyl, cycloalkenyl, alkoxy, alkenyloxy, alkynyloxy, cycloalkoxy, aryloxy, hetaryloxy, heterocyclyloxy, cycloalkenyloxy, alkoximino, alkenyloximino, alkynyloximino, cycloalkyloximino, cycloalkenyloximino, aryloximino, hetaryloximino, heterocyclyloximino, alkoxycarbonyl, alkenyloxycarbonyl, alkynyloxycarbonyl, cycloalkoxycarbonyl, aryloxycarbonyl, hetaryloxycarbonyl, heterocyclyloxycarbonyl, cycloalkenyloxycarbonyl, —$CONR^{12}R^{13}$, —N($R^{12}$)—CO—, alkylthio, alkenylthio, alkynylthio, cycloalkylthio, arylthio, hetarylthio, heterocyclylthio, cylcoalkenylthio, alkylamino, alkenylamino, alkynylamino, cycloalkylamino, arylamino, hetarylamino, heterocyclylamino, cycloalkenylamino, alkylcarbonyl, alkenylcarbonyl, alkynylcarbonyl, cycloalkylcarbonyl, arylcarbonyl, hetarylcarbonyl, heterocyclylcarbonyl, cycloalkenylcarbonyl, alkylsulfoxyl, alkenylsulfoxyl, alkynylsulfoxyl, cycloalkylsulfoxyl, arylsulfoxyl, hetarylsulfoxyl, heterocyclylsulfoxyl, cycloalkenylsulfoxyl, alkylsulfonyl, alkenylsulfonyl, alkynylsulfonyl, cycloalkylsulfonyl, arylsulfonyl, hetarylsulfonyl, heterocyclylsulfonyl, cycloalkenylsulfonyl, alkylsulfinyl, alkenylsulfinyl, alkynylsulfinyl, cycloalkylsulfinyl, arylsulfinyl, hetarylsulfinyl, heterocyclylsulfinyl or cylcoalkenylsulfinyl.

The abovementioned alkyl radicals are preferably methyl, ethyl, propyl, n-propyl, isopropyl, butyl, n-butyl, isobutyl, tert-butyl, sec-butyl, pentyl, pent-1-yl, pent-2-yl, pent-3-yl, 2-methylbut-1-yl, 2-methylbut-2-yl, 2-methylbut-3-yl, 3-methylbut-1-yl, 2,2-dimethylprop-1-yl, hexyl, hex-1-yl, hex-2-yl, hex-3-yl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, hept-1-yl, hept-2-yl, hept-3-yl, hept-4-yl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylbutyl, 1-isopropylbutyl, octyl, oct-1-yl, oct-2-yl, oct-3-yl, oct-4-yl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 1-propylpentyl, 2-propylpentyl, nonyl, 1-nonyl, 2-nonyl, 3-nonyl, 4-nonyl, 5-nonyl, 1-methyloctyl, 2-methyloctyl, 3-methyloctyl, 4-methyloctyl, 5-methyloctyl, 6-methyloctyl, 7-methyloctyl, 4-methyl-2-propylpentyl, decyl, 1-decyl, 2-decyl, 3-decyl, 4-decyl, 5-decyl, 1-ethyloctyl, 2-ethyloctyl, 3-ethyloctyl, 4-ethyloctyl, 5-ethyloctyl, 6-ethyloctyl or 2-propylheptyl.

The abovementioned alkenyl radicals are preferably ethenyl, 1-propenyl, 2-propenyl, butenyl, 1-butenyl, 2-butenyl, 3-butenyl, 1-methyl-2-propenyl, 2-methyl-2-propenyl, pentenyl, 1-pentenyl, 2-pentenyl, 3-pentenyl 4-pentenyl, 1-methyl-2-butenyl, 2-methyl-2-butenyl, 3-methyl-2-butenyl, 1-methyl-3-butenyl, 2-methyl-3-butenyl, 3-methyl - 3 -butenyl, 1,1-dimethyl-2-propenyl, 1,2-dimethyl-2-propenyl, 1-ethyl-2-propenyl, hexenyl, 1-hexenyl, 2-hexenyl, 3-hexenyl, 4-hexenyl, 5-hexenyl, 1-methyl-2-pentenyl, 2-methyl-2-pentenyl, 3-methyl-2-pentenyl 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl- 3-butenyl, 1,1,2-trimethyl-2-propenyl, 1-ethyl -1-methyl-2-propenyl, heptenyl, octenyl, nonenyl or decenyl.

The abovementioned alkynyl radicals are preferably ethynyl, 1-propynyl, 2-propynyl, butynyl, 1-butynyl, 2-butynyl, 3-butynyl, 1-methyl-2-propynyl, pentynyl, 1-pentynyl, 2-pentynyl, 3-pentynyl, 4-pentynyl, 1-methyl-2-butynyl, 1-methyl-3-butynyl, 2-methyl-3-butynyl, 1,1-dimethyl-2-methyl-2-pentynyl, hexynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, heptynyl, octynyl, nonynyl or decynyl.

The abovementioned halogens are fluorine, chlorine, bromine or iodine.

The abovementioned cycloalkyl radicals are preferably cyclopropyl, cyclobutyl, cyclopentyl, cyclohexyl, cycloheptyl, cyclooctyl, cyclononyl, cyclodecyl, bornanyl, norbornanyl, dicyclohexyl, bicyclo[3.3.0]octyl, bicyclo[3.2.1]octyl, bicyclo[2.2.2]octyl or bicyclo[3.3.1]nonyl.

The abovementioned cycloalkenyl radicals are preferably cyclopropenyl, cyclobutenyl, cyclopentenyl, cyclohexenyl, cycloheptenyl, cyclooctenyl, cyclononenyl, cyclodecenyl, bornenyl, norbornenyl, bicyclo[3.3.0]octenyl, bicyclo[3.2.1]octenyl, bicyclo[2.2.2]octenyl or bicyclo[3.3.1]nonenyl.

The abovementioned haloalkyl radicals are preferably $C_1$-$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The abovementioned haloalkoxy radicals are preferably $C_1$-$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy.

The abovementioned aryl radicals are preferably phenyl, 1-naphthyl, 2-naphthyl, 1-anthracenyl, 2-anthracenyl or 9-anthracenyl.

The abovementioned hetaryl radicals are preferably furyl, 2-furyl, 3-furyl, thienyl, 2-thienyl, 3-thienyl, pyrryl, 1-pyrryl, 2-pyrryl, 3-pyrryl, isoxazolyl, 3-isoxazolyl, 4-isoxazolyl, 5-isoxazolyl, isothiazolyl, 3-isothiazolyl, 4-isothiazolyl, 5-isothiazolyl, pyrazolyl, 1-pyrazolyl, 3-pyrazolyl, 4-pyrazolyl, 5-pyrazolyl, oxazolyl, 2-oxazolyl, 4-oxazolyl, 5-oxazolyl, thiazolyl, 2-thiazolyl, 4-thiazolyl, 5-thiazolyl, imidazolyl, 1-imidazolyl, 2-imidazolyl, 4-imidazolyl, 5-imidazolyl, 1,2,3-thiadiazolyl, 1,2,4-thiadiazolyl, 1,2,5-thiazolyl, 1,3,4-thiadiazolyl, tetrazolyl, 1,2,3,4-thiatriazolyl, 1,2,3,4-oxatriazolyl, pyridyl, 2-pyridyl, 3-pyridyl, 4-pyridyl, pyridazinyl, 3-pyridazinyl, 4-pyridazinyl, pyrimidinyl, 2-pyrimidinyl, 4-pyrimidinyl, 5-pyrimidinyl, pyrazinyl, 2-pyrazinyl, 3-pyrazinyl, 1,2,4-triazinyl, 1,3,5-triazinyl or 1,2,4,5-tetrazinyl.

Adjacent substituents of the hetero atom may be condensed to form an aromatic or heteroaromatic ring, so that hetaryl also comprises fused ring systems, for example benzofuranyl, isobenzofuranyl, 1-benzothienyl, 2-benzothienyl, indolyl, isoindolyl, benzisoxazolyl, benzoxazol, benzisothiazolyl, benzothiazolyl, 2-benzothiazolyl, 4-benzothiazolyl, 5-benzothiazolyl, 6-benzothiazolyl, 7-benzothiazolyl, indazolyl, benzimidazolyl, benzothiazolyl, benzofurazanyl, dibenzofuranyl, dibenzothienyl, acridinyl, phenanthridinyl, carbazolyl, quinolyl, isoquinolyl, phthalazinyl, quinazolinyl, quinoxalinyl, cinnolinyl, 1,5-naphthyridinyl, 1,6-naphthyridinyl, 1,7-naphthyridinyl, 1,8-naphthyridinyl, pteridinyl, pyrrolopyridinyl, pyrrolopyridazinyl, pyrrolopyrimidinyl, pyrrolopyrazinyl, pyrrolotriazinyl, furopyridinyl, furopyridazinyl, furotriazinyl, furopyrimidinyl, furopyrazinyl, thienopyridyl, thienopyridazinyl, thienopyrimidinyl, thienopyrazinyl, thienotriazinyl, imidazopyridinyl, imidazopyridazinyl, imidazopyrimidinyl, imidazopyrazinyl, pyrazolopyridyl, pyrazolopyridazinyl, pyrazolopyrimidinyl, pyrazolopyrazinyl, isoxazolopyridyl, isoxazolopyridazinyl, isoxazolopyrimidinyl, isoxazolopyrazinyl, oxaolopyridyl, oxazolopyridazinyl, oxazolopyrimidinyl, oxazolopyrazinyl, thiazolopyridyl, thiazolopyridazinyl, thiazolopyrimidyl, thiazolopyrazinyl, isothiazolopyridyl, isothiazolopyridazinyl, isothiazolopyrimidinyl, isothiazolopyrazinyl, triazolopyridyl, triazolopyridazinyl, triazolopyrimidinyl or triazolopyrazinyl.

The abovementioned heterocyclyl radicals are preferably 2-tetrahydrofuranyl, oxiranyl, 3-tetrahydrofuranyl, 2-tetrathydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,5-dihydrofur-2-yl, 2,5-dihydrofur-3-yl, 2,3-dihydrofur-3-yl, 2,3-dihydrothien-2-yl, 2,3-dihydrothien-3-yl, 2,5-dihydrothien-2-yl, 2,5-dihydrothien-2-yl, 2,4-pyrrolin-2-yl, 2,3-pyrrolin-3-yl, 2,5-pyrrolin-2-yl, 2,5-pyrrolin-3-yl, 2,3-isoxazolin-3-yl, 3,4-isoxazolin-3-yl, 4,5-isoxazolin-2-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-2-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-2-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, oxazol-2-in-2-yl, 2-tetrahydropyranyl, 1,3-dioxolan-2-yl, thiazol-2-in-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, N-morpholinyl or dihydroquinazolinyl.

The novel compounds can be prepared, for example, by the following processes:

The nitrile 2 is obtained by a method similar to that described by H. Hoffmann et al. (Synthesis 1986, 548) from the dihydropyran 1. After deprotonation of the dihydropyran 1 by a strong organic base and treatment of the resulting anion with a formylating agent, such as dimethylformamide (similarly to A. Lozanova et al., Izv. Akad. Nauk. SSR, Ser. Khim (1989), 734; R. Boeckman et al., Tetrahedron Lett. 48 (1977), 4187), or reduction of the nitrile 2 with diisobutylaluminum hydride or Raney nickel, the aldehyde 3 is obtained (Scheme 1).

Scheme 1

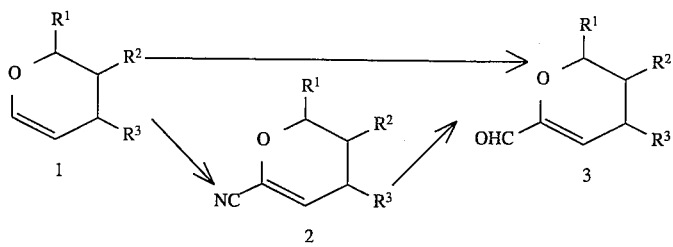

The aldehyde 3 can be reduced with a metal hydride, eg. sodium borohydride or lithium aluminum hydride, to give the alcohol 4. Alternatively, the aldehyde 3 can be reacted with an organometallic reagent ($R^5$-Metal, where Metal is Li, Mg, Na, Zn, Cd, Cu, etc.), the secondary alcohol 5 being obtained. This can be oxidized with oxidizing agents known from the literature (for example NaOCl, $Cr^{VI}$ reagents, dimethyl sulfoxide/oxalyl chloride) to give ketone 6 (Scheme 2).

Scheme 2

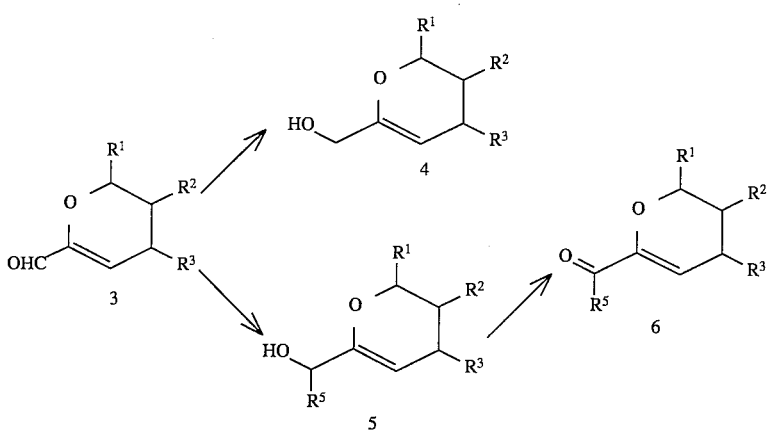

Mesylation (R. Cronland et al., J. Org. Chem. 35 (1970), 3195) of the alcohol 7 to give the methanesulfonic ester 8 and nucleophilic substitution of the mesyl radical give the dihydropyran 9, which can be reacted with Cl—CO—CO—$OR^{15}$/pyridine by a method similar to that described by M. Hajo et al., Synthesis 1986, 137, to give the glyoxylate 10. The novel compounds 11 (Scheme 3) are obtained by oximation of the ketoester 10 with $H_2N$—$OR^5$ or olefination of 10, for example with $(C_6H_5)_3 P^+$—$CH_2$—O—$R^5$ ($X^-$), $(C_6H_5)_3P^+$—$CH_2$—X ($X^-$) or $(C_6H_5)_3P^+$—$CH_2$—$R^6$ ($X^-$) (X=halogen) or the corresponding phosphonates or phosphine oxides.

Scheme 3

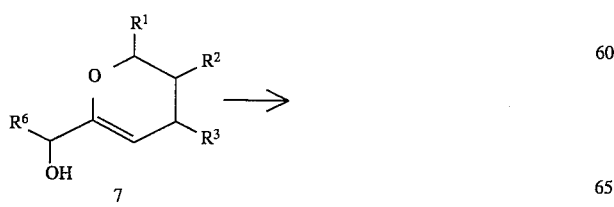

-continued
Scheme 3

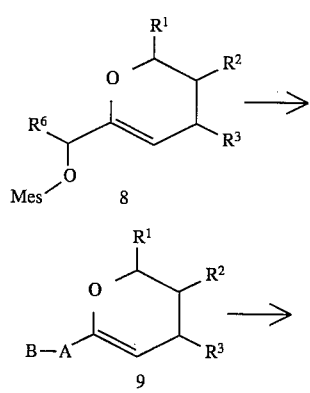

9
-continued
Scheme 3

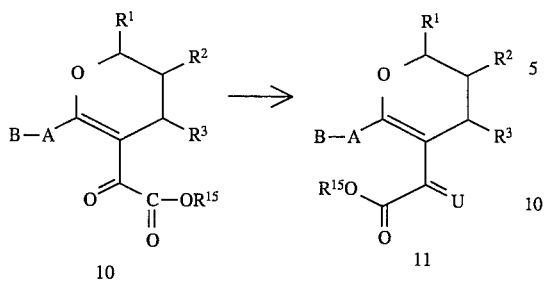

A: $-O-CHR^6-$, $-S-CH-R^6-$, $-NR^{18}-CHR^6-$,
$-C(=O)-O-CHR^6-$, $-(R^{19})C=N-O-CHR^6-$

U: $=CH-OR^5$, $=CHR^5$, $=CH$-Halogen, $=NOR^5$

Furthermore, the carbonyl compound 12 can be subjected to a Wittig reaction to give a di- or triunsaturated derivative 13. This reacts with Cl—CO—COOR$^{15}$/pyridine (cf. M. Hajo et al., Synthesis 1986, 137) to give the ketoester 14. Oximation of the glyoxylate 10 with $H_2N$—OR$^5$ or olefination of 10, for example with $(C_6H_5)_3P^+$—$CH_2$—OR$^5$ (X$^-$) $(C_6H_5)_3P^+$—$CH_2$—X (X$^-$) or $(C_6H_5)_3P^+$—CH —R$^6$ (X$^-$) (X=halogen) or the corresponding phosphonates or phosphine oxides, gives the novel compounds 15 (Scheme 4).

Scheme 4

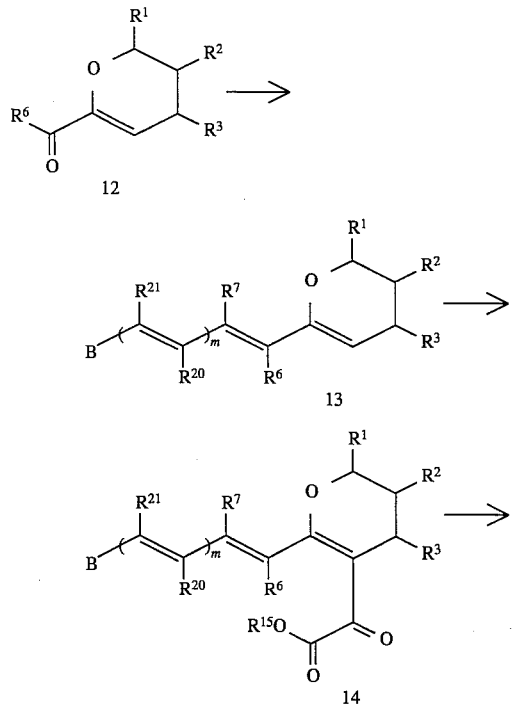

10
-continued
Scheme 4

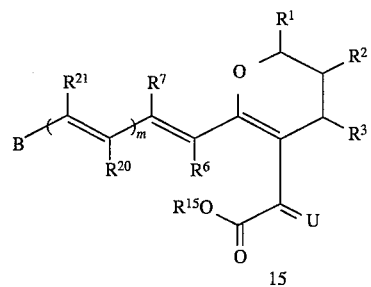

U: $=CH-OR^5$, $=CHR^6$, $=CH-X$, $=NOR^6$

In addition, the polyunsaturated compounds 14 can be selectively hydrogenated in the side chain with hydrogen in the presence of suitable catalysts, such as Pd, Pt or Ni, so that dihydropyran derivatives 16 are obtained. These can be converted into the novel compounds 17 by oximation with $H_2N$—OR$^5$ or by olefination, for example with $(C_6H_5)_3P^+$—$CH_2$—OR$^5$ (X$^-$), $(C_6H_5)_3P^+$ —$CH_2$ —X (X$^-$) or $(C_6H_5)_3P^+$—$CH_2$—R$^6$ (X$^-$) (X=halogen) or the corresponding phosphonates or phosphine oxides (Scheme 5).

Scheme 5

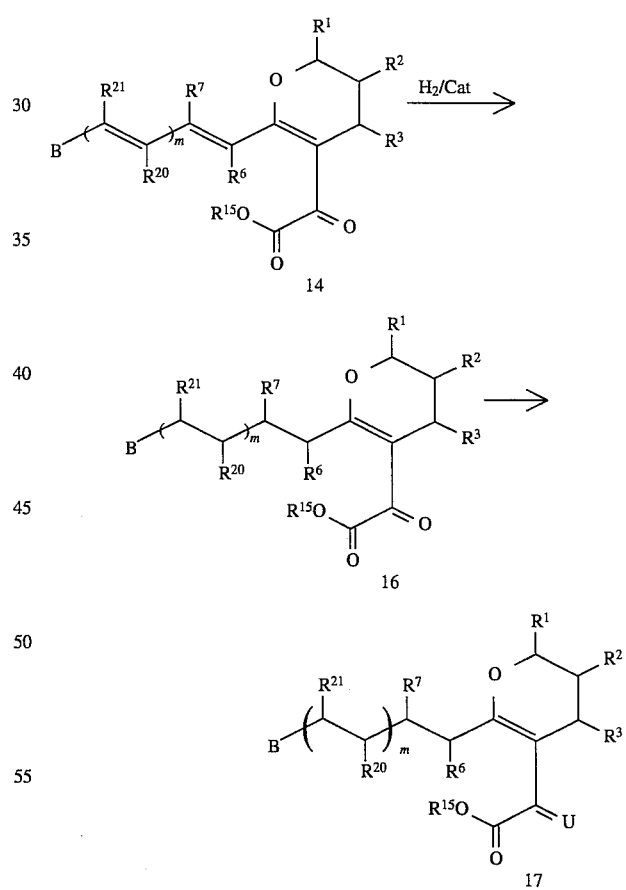

The thioenol ethers 19 are obtainable by reacting the derivatives 18 with mercaptans under basic conditions (Scheme 6).

Scheme 6

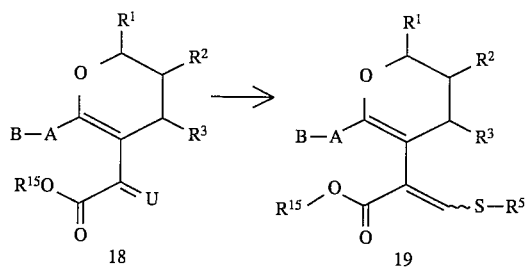

U: CHX (X = halogen), =CH—OR$^5$

The esters 20 react with amines HNR$^{16}$R$^{17}$ to give the corresponding amides 21 (Scheme 7).

Scheme 7

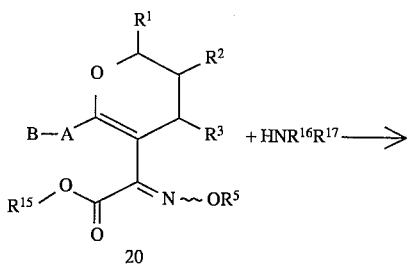

Alternatively, the esters 20 can also be reacted with carboxylic ester enolates (cf. for example E. Tao et al., Org. Prep. Proc. Int. Briefs 17 (1985), 235) to give the β-ketoesters 22, which, after decarboxylation with lithium chloride in dimethyl sulfoxide (cf. for example, S. Takai et al., Tetrahedron Lett. 49 (1975), 4389), give the ketones 23 (Scheme 8).

Scheme 8

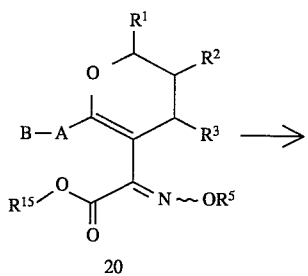

-continued
Scheme 8

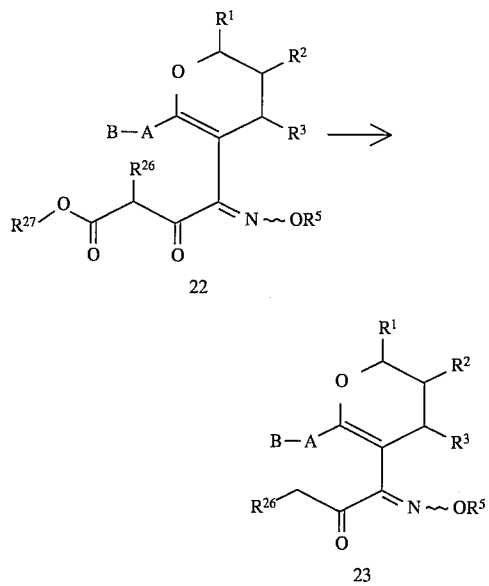

R$^{26}$: H, C$_1$–C$_6$-alkyl, aryl, hetaryl
R$^{27}$: C$_1$-alkyl.

Acetylenes of the formula 26 can be obtained by methods known from the literature, for example by addition of halogen at the double bond of the side chains of 24, the dihalide 25 being obtained, and subsequent thermal or base-catalyzed elimination of HX (X=halogen; Scheme 9).

Scheme 9

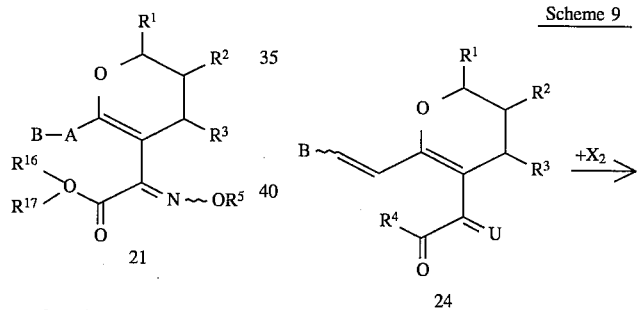

Alternatively, the novel compounds can also be synthesized using protective groups. For example, the carbonyl compound 27 can be converted into its cyclic or acyclic acetal, thioacetal or hemithioacetal 28 (SG1=protective group of the carbonyl group; cf. for example: T. Greene, Protective Groups in Organic Synthesis, J. Wiley & Sons 1981, page 152 et seq.). The protected carbonyl compound 28 can then be converted, similarly to Schemes 4, 6, 7 and 8, into the compound 29, from which the free carbonyl compound 30 is obtainable by elimination of the protective group (cf. for example: T. Greene, Protective Groups in Organic Synthesis, J. Wiley & Sons 1981, page 152 et seq.). Alternatively, 30 can be obtained by oxidation of 35. 30 can then be rected similarly to Schemes 4, 5, 6, 7, 8 and 9 to give the active ingredients 31 (Scheme 10).

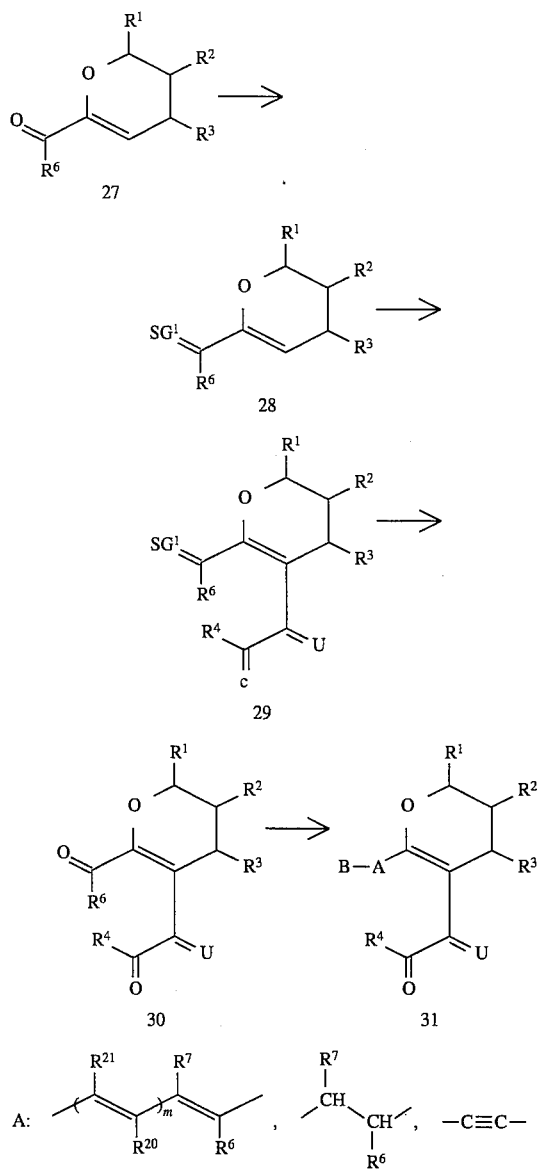

Scheme 10

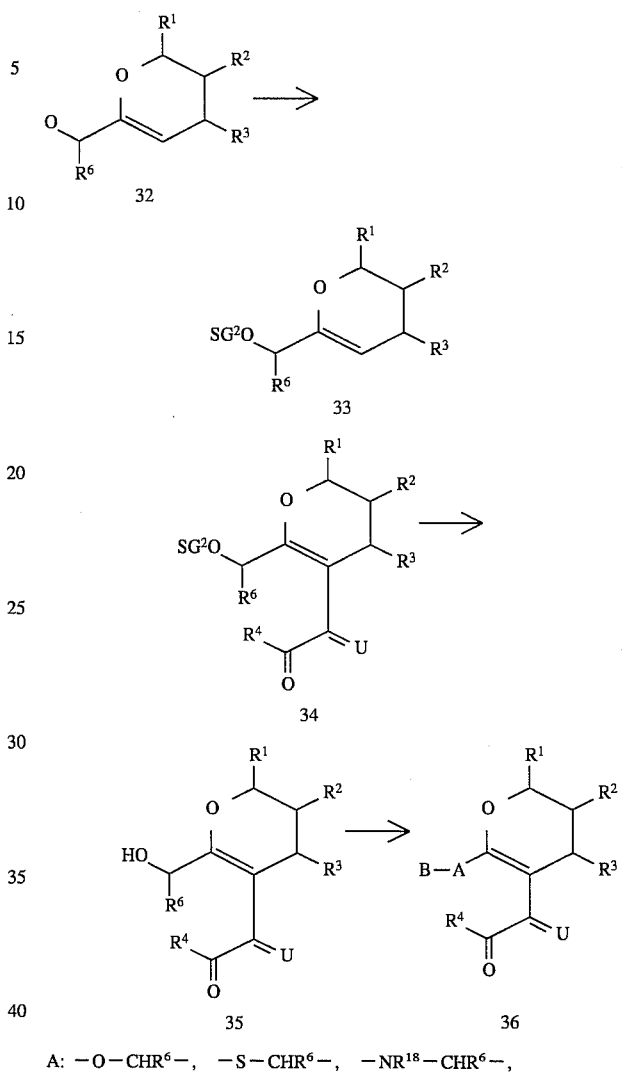

Scheme 11

A: $-O-CHR^6-$, $-S-CHR^6-$, $-NR^{18}-CHR^6-$, $-C(=O)-OCHR^6-$, $-CR^{19}=N-$ $O-CHR^6-$.

The Examples which follow illustrate the preparation of the novel compounds.

It is also possible to protect the alcohol 31 (SG2=protective group of the hydroxyl function), for example as an ether, ester or acetal 33 (cf. for example: T. Greene, Protective Groups in Organic Synthesis, J. Wiley & Sons 1981, page 10 et seq.). The protected alcohol 33 can then be converted, similarly to Schemes 3, 6, 7 and 8, into the compound 34, from which the free alcohol 35 is obtainable by elimination of the protective group (cf. for example: T. Greene, Protective Groups in Organic Synthesis, J. Wiley & Sons 1981, page 10 et seq.). Alternatively, 35 can also be obtained by reducing 30. 35 can be reacted similarly to Schemes 3, 6, 7 and 8 to give the active ingredients 36 (Scheme 11).

EXAMPLE 1

Methyl 2-(6-phenethenyl-2,3-dihydropyran-5-yl)-crotonate (Table 1, No. III/1)

a) 6-Formyl-2,3-dihydropyran 750 ml of a 1.5M solution of diisobutylaluminum hydride in toluene (1.1 mol) are added dropwise to 100 g (0.91 mol) of 6-cyano-2,3-dihydropyran (H. Hoffmann et al., Synthesis 1986, 548) in 200 ml of toluene at −70° to −60° C. Stirring is carried out at −60° C. for about 30 minutes and the reaction mixture is poured onto ice water. It is then carefully acidified with concentrated hydrochloric acid so that the total precipitate dissolves. The organic phase is separated off and the aqueous phase is extracted a further three times with methylene chloride. The combined organic phases are washed with 10% strength hydrochloric acid and water, dried over MgSO$_4$ and evaporated down under reduced pressure. The residue is distilled. 80 g (78%) of the title compound (cf. R. Boeckmann et al., Tetrahedron Lett. 48 (1977), 4187) are obtained as a colorless liquid.

bp.$^{0.3}$=45°–47° C. $^1$H-NMR (CDCl$_3$): δ (ppm): 9.1 (s, 1H, CHO); 5.9 (t, 1H, J=4 Hz, HC=C); 4.15 (t, 2H, J=5 Hz, O—CH$_2$), 2.15 (m, 2H, CH$_2$); 1.95 (m, 2H, CH$_1$)

b) 6-Phenethenyl-2,3-dihydropyran 40 g (0.36 mol) of potassium tert-butylate are added a little at a time to 150 g (0.39 mol) of benzyltriphenylphosphonium chloride in 500 ml of tetrahydrofuran at 0°–10° C. The orange reaction mixture is stirred for 30 minutes at about 0° C. Thereafter, 37.5 g (0.34 mol) of 6-formyl-2,3-dihydropyran (Example 1a) are added, the cooling is removed and stirring is carried out for a further 30 minutes. The reaction mixture is then poured onto NH$_4$Cl solution and the aqueous phase is extracted with methylene chloride. The combined organic phases are dried over MgSO$_4$ and evaporated down. The semisolid residue is stirred up with 300 ml of ether and filtered under suction over a short silica gel column. The filtrate is evaporated down and the residue is chromatographed using 3:1 cyclohexane/ethyl acetate. 53.5 g (0.29 mol=85%) of the title compound (about 5:1 isomer mixture) are obtained as a pale oil.

$^1$H-NMR (CDCl$_3$): δ (ppm): 7.1–7.9 (m, 5H, aromatic), 6.8 (d, 1H (secondary component), J=16 Hz, —C=C—H); 6.45 (d, 1H (secondary component), J=16 Hz, —C=C—H); 6.3 (d, 1H (main component); J=13 Hz, —C=C—H); 5.85 (d, 1H (main component), J=13 Hz, —C=C—H); 4.9 (m, 1H, O—C=C—H); 4.1 (t, 2H (secondary component), J=5 Hz, O—CH$_2$), 3.9 (t, 2H (main component), J=5 Hz, O—CH$_2$), 2.1 (m, 2H, CH$_2$); 1.8 (m, 2H, CH$_2$)

c) Methyl 6-trans-phenethenyl-2,3-dihyropyran-5-yl-glyoxylate 44 g (0.36 mol) of methyl oxalate are added dropwise to 53.5 g (0.29 mol) of 6-phenethenyl-2,3-dihydropyran (Example 1b) and 31 g (0.4 mol) of pyridine in 250 ml of methylene chloride. During this procedure, the reaction mixture heats up to the reflux temperature. Stirring is carried out overnight at room temperature (20° C). The reaction mixture is then extracted with dilute hydrochloric acid and water. The organic phase is dried over MgSO$_4$ and evaporated down. The residue is purified by column chromatography using cyclohexane/ethyl acetate mixtures. 82.5 g (about 90% purity; 0.27 mol=94%) of the title compound (trans configuration) are obtained as a colorless oil.

$^1$H-NMR (CDCl$_3$): δ (ppm): 7.2–7.4 (m, 7H, aromatic, H—C=C—H); 4.25 (t, 2H, O—CH$_2$); 3.8 (s, 3H, OCH$_3$), 2.5 (t, 2H, CH$_2$); 1.95 (t, 2H, CH$_2$)

d) Methyl 2-(6-trans-phenethenyl-2,3-dihydropyran-5-yl)-trans-crotonate (Table 1, No. III/1)

4.1 g (36.5 mmol) of potassium tert-butylate are added a little at a time to 21 g (50.2 mmol) of ethyltriphenylphosphonium chloride in 100 ml of tetrahydrofuran at 0°–5° C. Stirring is carried out for 15 minutes at 0°–5° C., the mixture is cooled to −20° C. and 7 g (26 mmol) of methyl 6-trans-phenethenyl-2,3-dihydropyran-5-ylglyoxylate (Example 1c) are added. Thereafter, the reaction mixture is allowed to warm up to room temperature and is poured onto NH$_4$Cl solution, and the aqueous phase is extracted three times with methylene chloride. The combined organic phases are dried over MgSO$_4$ and evaporated down. The residue is purified by column chromatography using cyclohexane/ethyl acetate mixtures. 2.7 g (9.5 mmol=37%) of the title compound are obtained as a colorless oil.

$^1$H-NMR (CDCl$_3$): δ (ppm): 7.15–7.4 (m, 5H, aromatic); 7.1 (q, 1H, Me—C=CH); 6.8 (d, 1H, J=16 Hz, —H—C=C—); 6.45 (d, 1H, J=16 Hz, —C=C—H—); 4.15 (m, 2H, O—CH$_2$); 3.65 (s, 3H, OCH$_3$); 2.2 (m, 2H, CH$_2$); 1.95 (t, broad, 2H, CH$_2$); 1.75 (d, 3H, J=8 Hz, CH$_3$)

EXAMPLE 2

Methyl 2-(6'-phenethyl-2',3'-dihydropyran-5'-yl)-3-methoxyacrylate (Table 4, No. I/422)

a) Methyl 6-phenethyl-2,3-dihydropyran-5-ylglyoxylate 30 g (0.11 mol) of methyl 6-phenethenyl-2,3-dihydropyran-5-ylglyoxylate and 3 g of PtO$_2$ (5% on SiO$_2$) in 250 ml of methanol are vigorously stirred under a H$_2$ atmosphere at room temperature for 24 hours. Thereafter, an additional 1 g of PtO$_2$ (5% of SiO$_2$) is added and stirring is continued for 8 hours at 50° C. and then overnight at room temperature. The catalyst is then filtered off under suction and the filtrate is evaporated down. The residue is purified by column chromatography using cyclohexane/ethyl acetate mixtures. 15.6 g (57 mmol=52%) of the title compound are obtained as a colorless oil.

$^1$H-NMR (CDCl$_3$): δ (ppm): 7.25 (m, 5 H, aromatic); 4.15 (t, 2H, J=6 Hz, O—CH$_2$), 3.85 (s, 3H, OCH$_3$); 2.8 (m, 4H, Ph—CH$_2$—CH$_2$), 2.35 (t, 2H, J=6 Hz, CH$_2$); 1.85 (m, 2H, CH$_2$)

b) Methyl 2-(6'-phenethyl-2',3'-dihydropyran-5'-yl)-3-methoxyacrylate (Table 4, No. I/422)

2.8 g (25 mmol) of potassium tert-butylate are added a little at a time to 10 g (29 mmol) of methoxytriphenylphosphonium chloride in 40 ml of tetrahydrofuran at 0°–5° C. Stirring is carried out for 15 minutes at 0° C., the mixture is cooled to −60° C. and 4 g (14.6 mmol) of methyl 6-phenethyl-2,3-dihydropyran-5-ylglyoxylate (Example 2a) are added. The mixture is allowed to warm up to room temperature and is poured onto NH$_4$Cl solution, and the aqueous phase is extracted three times with diethyl ether. The combined organic phases are dried over MgSO$_4$ and evaporated down. The residue is purified by column chromatography using hexane/ethyl acetate mixtures. 2.1 g (6.9 mmol=48%) of the trans isomer (colorless crystals, mp.=83°–85° C.), and 1.6 g (5.3 mmol =36%) of the cis isomer (colorless oil) of the title compound are obtained.

trans-Isomer, $^1$H-NMR (CDCl$_3$): δ (ppm): 7.3 (s, 1H, —C=C—H); 7.1–7.3 (m, 5H, aromatic); 4.05 (t, 3H, J=6 Hz, OCH$_2$); 3.8 (s, 3H, OCH$_3$); 3.65 (s, 3H, OCH$_3$); 2.75 (m, 2H, CH$_2$); 2.25 (m, 2H, CH$_2$); 2.05 (t, broad, 2H, CH$_2$), 1.9 (m, 2H, CH$_2$)

cis-Isomer, $^1$H-NMR (CDCl$_3$): δ (ppm): 7–7.4 (m, 5H, aromatic), 5.45 (s, 1H, =—H); 4.05 (t, 2H, J=6 Hz, O—CH$_2$); 3.65 (s, 3H, OCH$_3$); 3.6 (s, 3H, OCH$_3$); 2.75 (t, 2H, J=8 Hz, CH$_2$); 2.35 (t, 2H, J=8Hz, CH$_2$); 2.0 (t, broad, 2H, CH$_2$); 1.85 (m, 2H, —CH$_2$)

EXAMPLE 3

Methyl 2-(6'-trans-ortho-methylphenethenyl-2',3'-dihydropyran-5'-yl)-3-chloroacrylate (Table 7, No. 42)

2.8 g (25 mmol) of potassium tert-butylate are added a little at a time to 12 g (34 mmol) of chloromethyltriphenylphosphonium chloride, 50 g (17 mmol) of methyl trans-6-ortho-methylphenethenyl-2,3-dihydropyran-5-ylglyoxylate (prepared similarly to Example 1c) and 1 ml of methanol in 100 ml of tetrahydrofuran at room temperature. Stirring is carried out for 3 hours at room temperature and the reaction mixture is poured onto water. The aqueous phase is extracted three times with diethyl ether. The combined organic phases are dried over MgSO$_4$ and evaporated down. The semisolid residue is stirred with diethyl ether and filtered off under suction. Thereafter, the filtrate is evaporated down and the remaining residue is purified by column chromatography using hexane/ethyl acetate mixtures. The cis-chloro- and trans-chloroacrylate isomers of the title compound are obtained as a mixture: 0.9 g (2.8 mmol=16%; pale yellow oil) in a cis/trans ratio of 1:10 and 3.7 g (11.5 mmol=67%; pale yellow oil) in a cis/trans ratio of 1:3.

$^1$H-NMR (CDCl$_3$): δ (ppm): 7.5 (s, 1H (trans), C=CCl—H); 7.04–7.45 (m, 5H, aromatic, —C=C—H); 6.65 (d, 1H (cis), J=16 Hz, —C=C—H), 6.4 (s, 1H (cis), C=CCl—H); 6.3 (d, 1H (trans), J=16 Hz, —C=C—H); 4.2 (m, 2H, O—CH$_2$); 3.8 (s, 3H (cis), OCH$_3$); 3.75 (s, 3H (trans), OCH$_3$); 2.35 (s, 3H, CH$_3$); 2.25 (t, broad, 2H, CH$_2$); 2.0 (m, 2H, CH$_2$)

EXAMPLE 4

Methyl 2-(6'-trans-ortho-methylphenethenyl-2',3'-dihydropyran-5'-yl)-3-trans-methylthioacrylate (Table 7, No. 44)

0.22 g (3.1 mmol) of sodium thiomethylate is added to 0.9 g (2.8 mmol) of methyl 2-(6'-trans-ortho-methylphenethenyl-2',3'-dihydropyran -5'-yl)-3-transchloroacrylate (Example 3) in 8 ml of dimethylformamide, the reaction mixture warming up to about 35° C. Stirring is carried out for about 30 minutes, the reaction mixture is poured onto water and the aqueous phase is extracted three times with diethyl ether. The combined organic phases are dried over MgSO$_4$ and evaporated down. The residue is purified by column chromatography using hexane/ethyl acetate mixtures. 0.68 g (2 mmol=72%) of the title compound are obtained as a pale yellow oil.

$^1$H-NMR (CDCl$_3$): δ (ppm): 7.7 (s, 1H, C=C(SMe)—H); 7.4 (m, 1H, aromatic); 7–7.2 (m, 4H, aromatic, —C=C—H); 6.35 (d, 1H, J=16 Hz, —H—C=C—); 4.15 (t, 1H, J=6 Hz, O—CH$_2$); 3.7 (s, 3H, OCH$_3$); 2.4 (s, 3H, CH$_3$); 2.35 (s, 3H, CH$_3$); 2.2 (m, 2H, CH$_2$); 1.95 (m, 2H, CH$_2$)

EXAMPLE 5

Methyl 2-[6'-(4'''-chlorophenyl-3''-isoxazol-5''-ylethenyl)-2',3'-dihydropyran -5'-yl]-3-methoxyacrylate (Table 2, No. I/396)

a) 6'-(4'''-chlorophenyl-3''-isoxazol-5''-ylethenyl)-2',3'-dihydropyran 0.8 g (33 mmol) of sodium hydride is added a little at a time to 10 g (30 mmol) of diethyl 4'''-chlorophenyl-3''-isoxazol-5''-ylmethylphosphonate in 100 ml of tetrahydrofuran while cooling with a water bath. Stirring is carried out for 15 minutes at room temperature, after which 3 g (27 mmol) of 6-formyl-2,3-dihydropyran (Example 1a) are added. Stirring is carried out for 1 hour at room temperature, and the reaction mixture is poured over dilute hydrochloric acid (pH=3-4) and the aqueous phase is extracted three times with methylene chloride. The combined organic phases are dried over MgSO$_4$ and evaporated down. The remaining solid is stirred with methyl tert-butyl ether and filtered off under suction. The residue obtained comprises 5.2 g (18 mmol=67%) of the title compound as pale yellow crystals.

$^1$H-NMR (CDCl$_3$): δ (ppm): 7.7 (d, 2H, J=8 Hz, phenyl); 7.4 (d, 2H, J=8 Hz, phenyl); 6.65 (s, 2H, H—C=C—H); 6.4 (s, 1H, isoxazolyl); 5.15 (t, 2H, J=4 Hz, —C=C—H); 4.1 (t, 2H, J=5 Hz, O—CH$_2$); 2.2 (m, 2H, CH$_2$); 1.9 (m, 2H, CH$_2$)

b) Methyl 6'-(4'''-chlorophenyl-3''-isoxazol-5''-yl-trans-ethenyl)-2',3'-dihydropyran -5'-ylglyoxylate 5.5 g (19 mmol) of 6'-(4'''-chlorophenyl-3''-isoxazol-5''-ylethenyl)-2',3'-dihydropyran (Example 5a), 2.5 g (32 mmol) of pyridine and 3 g (24.6 mmol) of methoxyalyl chloride are stirred for 4 days at room temperature. The reaction mixture is poured onto water and the aqueous phase is extracted three times with methylene chloride. The combined organic phases are dried over MgSO$_4$ and evaporated down. The residue is recrystallized with methyl tert-butyl ether. 3.4 g (9.1 mmol=48%) of the title compound are obtained as pale yellow crystals.

$^1$H-NMR (CDCl$_3$): δ (ppm): 7.75 (d, 2H, J=8 Hz, phenyl); 7.65 (d, 1H, J =16 Hz, vinyl); 7.4 (d, 2H, J=8 Hz, phenyl); 7.15 (d, 1H, J=16 Hz, vinyl); 6.65 (s, 1H, isoxazolyl); 4.25 (t, 2H, J=5 Hz, O—CH$_2$); 3.9 (s, 3H, OCH$_3$); 2.5 (t, 2H, J=6 Hz, CH$_2$); 2.0 (m, 2H, CH$_2$)

c) Methyl 2-[6'-(4'''-chlorophenyl-3''-isoxazol-5''-yl-trans-ethenyl)-2',3'-dihydropyran-5'-yl]-3-methoxyacrylate (Table 2, No. I/396)

2.1 g (19 mmol) of potassium tert-butylate are added a little at a time to 7.5 g (22 mmol) of methoxytriphenylphosphonium chloride in 50 ml of tetrahydrofuran at 0°–5° C. Stirring is carried out for 30 minutes at 0°–5° C., 3.4 g (9.1 mmol) of methyl 6'-(4'''-chlorophenyl-3''-isoxazol -5''-yl-trans-ethenyl)-2',3'-dihydropyran-5'-ylglyoxylate (Example 5b) are added and the mixture is allowed to warm up to room temperature. After 30 minutes, the reaction mixture is poured onto water and the aqueous phase is extracted three times with ether. The combined ether phases are dried over MgSO$_4$ and evaporated down. An oily residue is obtained and is purified by column chromatography using hexane/ethyl acetate mixtures. 1.4 g (3.5 mmol=38%; colorless crystals, mp.=170° C.) of the trans-methoxy isomer and 0.44 g (1.1 mmol=12%, colorless crystals, mp.=181° C.) of the cis-methoxy isomer of the title compound are obtained.

trans-Isomer, $^1$H-NMR (CDCl$_3$): δ (ppm): 7.75 (d, 2H, J=8 Hz, phenyl); 7.45 (s, 1H, C=C(OMe)—H); 7.4 (d, 2H, J=8 Hz, phenyl); 6.85 (d, 1H, J=16 Hz; —C=C—H); 6.7 (d, 1H, J=16 Hz, —C=C—H); 6.4 (s, 1H, isoxazolyl); 4.15 (t, 2H, J=5 Hz, O—CH$_2$); 3.85 (s, 3H, OCH$_3$); 3.75 (s, 3H, OCH$_3$), 2.25 (t, broad, CH$_2$); 1.95 (t, broad, CH$_2$)

cis-Isomer, $^1$H-NMR (CDCl$_3$): δ (ppm): 7.75 (d, 2H, J=8 Hz, phenyl); 7.45 (d, 2H, J=8 Hz, phenyl); 7.1 (d, 1H, J=16 Hz, —C=C—H); 6.75 (d, 1H, J=16 Hz, =—H); 6.4, 6.45 (2s, each 1 H, isoxazolyl and C=C—(OMe)—H); 4.15 (t, 2H, J=5 Hz, OCH$_2$); 3.9 (s, 3H, OCH$_3$); 3.8 (s, 3H, OCH$_3$); 2.3 (t, 2H, J=6 Hz, CH$_2$); 19 (m, 2H, CH$_2$)

EXAMPLE 6

N-Methyl-6'-(2'',5''-dimethylphenyl-trans-ethenyl)-2',3'-dihydropyran-5'-ylglyoxylamide trans-O-methyloxime (Table 77, No. 47)

A mixture of 0.6 g (1.8 mmol) of methyl 6'-(2'',5''-dimethylphenyl -trans-ethenyl)-2',3'-dihydropyran-5'-ylglyoxylate trans-O-methyloxime (Table 1, No. II/133; prepared similarly to Examples 1a–c and 7 e, f) and 10 ml of 40% strength aqueous methylamine solution is stirred at 50° C. for 2 hours. The heterogeneous reaction mixture is allowed to cool and is extracted three times with methylene chloride. The combined organic phases are dried over MgSO$_4$ and evaporated down. After chromatographic purification of the residue using hexane/ethyl acetate mixtures, 0.45 g (1.4 mmol=76%) of the title compound is obtained as a colorless solid.

mp.=165°–168° C. $^1$H-NMR (CDCl$_3$): δ (ppm): 6.9–7.2 (m, 4H, aromatic, vinyl); 6.7 (s, broad, 1H, N—H); 6.1 (d, 1H, J=16 Hz, vinyl); 4.2 (t, 2H, J=5 Hz, O—CH$_2$), 4.0 (s, 3H, OCH$_3$); 2.9 (d, 3H, J=5 Hz, NCH$_3$); 2.3 (m, 8 H, 2×CH$_3$, CH$_2$); 2.0 (m, 2H, CH$_2$)

EXAMPLE 7

Methyl 6-phenoxymethyl-2,3-dihydropyran-5-ylglyoxylate trans-O-methyloxime (Table 7, No. 23)

a) 6-Hydroxymethyl-2,3-dihydropyran 9.5 g (0.25 mol) of sodium borohydride are added a little at a time to 56 g (0.5 mol) of 6-formyl-2,3-dihydropyran (Example 1a) in 400 ml of isopropanol while cooling with an ice-water bath. The reaction mixtrue warms up to 40° C. during this procedure. Stirring is carried out for 1 hour at 0° C., after which the reaction mixture is poured onto water and the aqueous phase is extracted three times with methylene chloride. The combined organic phases are dried over $MgSO_4$ and evaporated down. 45 g of the title compound are obtained as a yellow oil, which is used as the crude product in the next reaction.

b) 2,3-Dihydropyran-6-ylmethyl methanesulfonate 51.5 g (0.45 mol) of methanesulfonyl chloride are added dropwise to 45 g (0.39 mmol) of 6-hydroxymethyl-2,3-dihydropyran (Example 7a) and 50 g (0.5 mol) of triethylamine in 400 ml of methylene chloride at 0°–5° C. Stirring is carried out for 1 hour at 0° C. and the reaction mixture is poured onto water. The aqueous phase is separated off and the organic phase is extracted once again with water and is then dried over $MgSO_4$ and evaporated down. 84 g of title compound are obtained as a red oil, which is used directly in the next reaction.

c) 6-Phenoxymethyl-2,3-dihydropyran 6.0 g (0.25 mol) of sodium hydride are added a little at a time at room temperature to 20.5 g (0.22 mol) of phenol in 200 ml of dimethylformamide. Stirring is carried out for 30 minutes at room temperature, after which 42 g (0.22 mol) of 2,3-dihydropyran-6-ylmethyl methanesulfonate (Example 7b) are added dropwise with slight cooling. Stirring is carried out for 4 hours at room temperature, after which the reaction mixture is poured onto water. The aqueous phase is extracted three times with diethyl ether and the organic phase is dried over $MgSO_4$ and evaporated down under reduced pressure. The residue is distilled. 27 g (0.14 mol= 57%, based on 6-formyl-2,3-dihydropyran) of the title compound are obtained as a pale yellow oil.

bp$_{0.3}$=70° C. $^1$H-NMR (CDCl$_3$): δ (ppm): 7.3 (t, 2H, J=8 Hz, phenyl); 6.95 (m, 3H, phenyl); 4.9 (t, 1H, J=4 Hz, vinyl), 4.35 (s, 2H, O—CH$_2$); 4.1 (t, 2H, J=5 Hz, O—CH$_2$); 2.05 (m, 2H, CH$_2$); 1.85 (m, 2H, CH$_2$)

d) Methyl 6-phenoxymethyl-2,3-dihydropyran-5-ylglyoxylate 35 g (0.29 mol) of methoxalyl chloride are added dropwise to 31 g (0.16 mol) of 6-phenoxymethyl-2,3dihydropyran (Example 7c), 39.5 g (0.5 mol) of pyridine and 2.5 g (0.02 mol) of p-dimethylaminopyridine in 200 ml of methylene chloride. During this procedure, the reaction mixture warms up to 30°–35 ° C. Stirring is carried out overnight and the reaction mixture is then poured onto water. The aqueous phase is separated off and the organic phase is extracted once again with water. The organic phase is then dried over $MgSO_4$ and evaporated down. The residue is purified by column chromatography using hexane/ethyl acetate mixtures. 16 g of starting material and 8.5 g (0.031 mol=19%, pale yellow oil) of the title compound are obtained.

$^1$H-NMR (CDCl$_3$): δ (ppm): 7.3 (t, 2H, J=8 Hz, phenyl); 6.8–7.1 (m, 3H, phenyl); 4.8 (s, 2H, O—CH$_2$); 4.2 (t, 2H, J=5 Hz, O—CH$_2$); 3.6 (s, 3H, OCH$_3$); 2.4 (t, 2H, J=6 Hz, CH$_2$); 1.9 (m, 2H, CH$_2$)

e) Methyl 6-phenoxymethyl-2,3-dihydropyran-5-ylglyoxylate cis-O-methyloxime (Table 7, No. 23a)

6 g (22 mmol) of methyl 6-phenoxymethyl-2,3-dihydropyran-5-ylglyoxylate (Example 7d), 3 g (38 mmol) of pyridine and 3 g (36 mmol) of o-methylhydroxylamine hydrochloride in 50 ml of methanol are stirred overnight at room temperature. The reaction mixture is evaporated down under reduced pressure, the residue is taken up in methylene chloride and the solution is extracted with water. Thereafter, the organic phase is dried over $MgSO_4$ and evaporated down. The residue is purified by column chromatography using hexane/ethyl acetate mixtures. 2.9 g (9.5 mmol=43%) of the title compound are obtained as a colorless oil.

$^1$H-NMR (CDCl$_3$): δ (ppm): 7.3 (t, 2H, J=8 Hz, phenyl); 6.9 (m, 3H, phenyl); 4.6 (s, 2H, O—CH$_2$); 4.1 (t, 2H, J=5 Hz, O—CH$_2$); 3.85 (s, 3H, OCH$_3$); 2.3 (t, 2H, J=6 Hz, CH$_2$); 1.9 (m, 2H, CH$_2$)

f) Methyl 6-phenoxymethyl-2,3-dihydropyran-5-ylglyoxylate trans-O-methyloxime (Table 7, No. 23b)

1 ml of 4M hydrogen chloride gas in diethyl ether is added to 5 g (16 mmol) of methyl 6-phenoxymethyl-2,3-dihydropyran-5-ylglyoxylate cis-O-methyloxime (Example 7e) in 20 ml of methylene chloride, and the mixture is stirred overnight at room temperature. The reaction mixture is then evaporated down under reduced pressure and the residue is purified by column chromatography using hexane/ethyl acetate mixtures. 0.8 g of starting material and 2.2 g (7.2 mmol=44%) of the title compound are obtained, the latter being in the form of a pale yellow oil.

$^1$H-NMR (CDCl$_3$): δ (ppm): 7.25 (t, 2H, J=8 Hz, phenyl); 6.9 (m, 3H, phenyl); 4.35 (s, 2H, O—CH$_2$); 4.15 (t, 2H, J=5 Hz, O—CH$_2$); 3.95 (s, 3H, OCH$_3$); 3.75 (s, 3H, OCH$_3$); 2.2 (t, 2H, J=6 Hz, CH$_2$); 1.9 (m, 2H, CH$_2$)

EXAMPLE 8

Methyl 6-(6'-ethylpyrid-2'-yloxymethyl)-2,3-dihydropyran-5-ylglyoxylate trans-O-methyloxime (Table 7, No. 25)

a) 6-(6'-Ethylpyrid-2'-yloxymethyl)-2,3-dihydropyran 6.6 g (0.275 mol) of sodium hydride are added a little at a time to 28 g (0.227 mol) of 2-hydroxy-6-ethylpyridine in 400 ml of dimethylformamide with slight cooling. Stirring is carried out for 30 minutes at room temperature, after which 41 g (0.213 mol) of 2,3-dihydropyran-6-ylmethyl methanesulfonate (Example 7b), dissolved in 50 ml of dimethylformamide, are added dropwise. Stirring is carried out overnight at room temperature, the reaction mixture is poured onto water and the aqueous phase is extracted three times with diethyl ether. The combined organic phases are washed once with water, dried over $MgSO_4$ and evaporated down. The residue is purified by distillation. 21.5 g (0.098 mol= 43%, based on 6-formyl-2,3-dihydropyran) of the title compound are obtained as a pale yellow oil.

$^1$H-NMR (CDCl$_3$): δ (ppm): 7.45 (t, 1H, J=8 Hz, pyridyl); 6.7 (d, 1H, J=8 Hz, pyridyl); 6.6 (d, 1H, J=8 Hz, pyridyl); 4.95 (t, 1H, J=4 Hz, vinyl); 4.7 (s, 2H, OCH$_2$); 4.1 (t, 2H, J=5 Hz, O—CH$_2$); 2.7 (q, 2H, J=8 Hz, CH$_2$); 2.1 (t, broad, 2H, CH$_2$); 2.8 (m, 2H, CH$_2$); 1.3 (t, 3H, J=8 Hz, CH$_3$)

b) Methyl 6-(6'-ethylpyrid-2'-yloxymethyl)-2,3-dihydropyran-5-ylglyoxylate 9 g (46.5 mmol) of 6-(6'-ethylpyrid-2'-yloxymethyl)-2,3-dihydropyran (Example 8a), 8 g (100 mmol) of pyridine and 8 g (65 mmol) of methoxalyl chloride in 100 ml of methylene chloride are stirred overnight at room temperature. Thereafer, the reaction solution is extracted with water, dried over $MgSO_4$ and evaporated down under reduced pressure. The residue is purified by column chromatography using hexane/ethyl acetate mixtures. 1.9 g of starting material and 6.6 g (21.6 mmol=47%) of the title compound are obtained, the latter being in the form of a pale yellow oil.

$^1$H-NMR (CDCl$_3$): δ (ppm): 7.5 (t, 1H, J=8 Hz, pyridyl); 6.75 (d, 1H, J =8 Hz, pyridyl); 6.55 (d, 1H, J=8 Hz, pyridyl); 5.15 (s, 2H, OCH$_2$); 4.15 (t, 2H, J=5 Hz, O—CH$_2$); 3.7 (s, 3H, OCH$_3$); 2.65 (q, 2H, J=8 Hz, CH$_2$); 2.4 (t, 2H, J=6 Hz, CH$_2$); 1.9 (m, 2H, CH$_2$); 1.3 (t, 3H, J=8 Hz, CH$_3$)

c) Methyl 6-(6'-ethylpyrid-2'-yloxymethyl)-2,3-dihydropyran-5-ylglyoxylate cis-O-methyloxime (Table 7, No. 25a)

12.2 g (40 mmol) of methyl 6-(6'-ethylpyrid-2'-yloxymethyl)-2,3-dihydropyran-5-ylglyoxylate (Example 8b), 7 g (88 mmol) of pyridine and 6 g (71 mmol) of O-methylhydroxylamine hydrochloride in 100 ml of methanol are stirred overnight at room temperature. Thereafter, the reaction mixture is evaporated down, the residue is taken up in methylene chloride and the organic phase is extracted with water, dried over $MgSO_4$ and then evaporated down. The residue is purified by column chromatography using hexane/ethyl acetate mixtures. 4.5 g (13.5 mmol=34%) of the title compound are obtained as a pale yellow oil.

$^1$H-NMR (CDCl$_3$): δ (ppm): 7.45 (t, 1H, J=8 Hz, pyridyl); 6.7 (d, 1H, J =8 Hz, pyridyl); 6.6 (d, 1H, J=8 Hz, pyridyl); 4.95 (s, 2H, O—CH$_2$); 4.1 (t, 2H, J=5 Hz, O—CH$_2$); 3.8 (s, 3H, OCH$_3$); 3.7 (s, 3H, OCH$_3$); 2.7 (q, 2H, J=8 Hz, CH$_2$); 2.3 (t, 2H, J=6 Hz, CH$_2$); 1.9 (m, 2H, CH$_2$); 1.3 (t, 3H, J=8 Hz, 3H)

d) Methyl 6-(6'-ethylpyrid-2'-yloxymethyl)-2,3-dihydropyran-5-ylglyoxylate trans-O-methyloxime (Table 7, No. 25b)

2 ml of a 2N solution of hydrogen chloride gas in ether are added to 8 g (26 mmol) of methyl 6-(6'-ethylpyrid-2'-yloxymethyl) -2,3-dihydropyran-5-ylglyoxylate cis-O-methyloxime (Example 8c) in 50 ml of methylene chloride in an open crystallizing dish, and the mixture is exposed to a 300 W UV lamp for about 5 hours from above. The evaporated solvent is replaced from time to time. The reaction solution is then transferred to a flask and evaporated down. The residue is purified by column chromatography using hexane/ethyl acetate mixtures. 2.8 g of starting material and 1.8 g (5.9 mmol =23%) of the title compound are obtained, the latter being in the form of a pale yellow oil.

$^1$H-NMR (CDCl$_3$): δ (ppm): 7.45 (t, 1H, J=8 Hz, pyridyl); 6.7 (d, 1H, J=8 Hz, pyridyl); 6.55 (d, 1H, J=8 Hz, pyridyl); 4.7 (s, 2H, OCH$_2$); 4.15 (t, 2H, J=5 Hz, OCH$_2$); 4.0 (s, 3H, OCH$_3$); 3.8 (s, 3H, OCH$_3$); 2.65 (q, 2H, J=8 Hz, CH$_2$); 2.2 (t, broad, CH$_2$); 1.95 (m, 2H, CH$_2$); 1.25 (t, 3H, J=8 Hz, CH$_3$)

EXAMPLE 9

Methyl 6-[1'-(4"-bromophenyl)-1'-methyliminooxymeth-4'-yl]-2,3-dihydropyran-5-ylglyoxylate trans-O-methyloxime (Table 7, No. 26)

a) 6-[1'-(4"-Bromophenyl)-1'-methyliminooxymeth-4'-yl]-2,3-dihydropyran 6 g (0.25 mol) of sodium hydride are added a little at a time to 46 g (0.215 mol) of 4-bromoacetophenone oxime in 300 ml of dimethylformamide. Stirring is carried out for about 1 hour at room temperature, after which 41.5 g (0.213 mol) of 2,3-dihydropyran-6ylmethyl methanesulfonate (Example 7b) are added dropwise with slight cooling. Stirring is carried out overnight at room temperature, the reaction mixture is poured onto water and the aqueous phase is extracted three times with diethyl ether. The ether phase is washed once with water, dried over $MgSO_4$ and evaporated down. The residue is purified by column chromatography using hexane/ethyl acetate mixtures. 53 g (0.171 mol=80%) of the title compound are obtained as a pale yellow oil.

$^1$H-NMR (CDCl$_3$): δ (ppm): 7.5 (m, 4H, phenyl); 4.9 (t, 1H, J=4 Hz, vinyl); 4.55 (s, 2H, OCH$_2$); 4.05 (t, 2H, J=5 Hz, O—CH$_2$); 2.25 (s, 3H, CH$_3$); 2.05 (m, 2H, CH$_2$); 1.85 (m, 2H, CH$_2$)

b) Methyl 6-[1'-(4"-bromophenyl)-1'-methyliminoxymeth-4'-yl]-2,3 -dihydropyran-5-ylglyoxylate 28 g (0.23 mol) of methoxalyl chloride are added dropwise to 53 g (0.17 mol) of 6-[1'-(4"-bromophenyl)-1'-methyliminooxymeth -4'-yl]-2,3-dihydropyran (Example 9a) and 20 g (0.38 mol) of pyridine in 30 ml of methylene chloride. Stirring is carried out overnight at room temperature, the reaction mixture is poured onto water and the aqueous phase is extracted three times with diethyl ether. The combined ether phases are dried over $MgSO_4$ and evaporated down. The residue is purified by column chromatography using hexane/ethyl acetate mixtures. 25.7 g (0.065 mol=38%) of the title compound are obtained as a yellow oil.

$^1$H-NMR (CDCl$_3$): δ (ppm): 7.5 (m, 4H, phenyl); 5.0 (s, 2H, OCH$_2$); 4.2 (t, 2H, J=5 Hz, O—CH$_2$); 3.8 (s, 3H, OCH$_3$); 2.4 (t, 2H, J=6 Hz, CH$_2$); 2.9 (m, 2H, CH$_2$)

c) Methyl 6-[1'-(4"-bromophenyl)-1'-methyliminoxymeth-4'-yl]-2,3-dihydropyran-5 -ylglyoxylate cis-O-methyloxime (Table 7, No. 26a)

25.7 g (65 mmol) of methyl 6-[1'-(4"-bromophenyl)-1'-methyliminooxymeth -4'-yl]-2,3-dihydropyran-5-ylglyoxylate (Example 9b), 10 g (127 mmol) of pyridine and 8.5 g (100 mmol) of O-methylhydroxylamine hydrochloride in 200 ml of methanol are stirred overnight at room temperature. The reaction mixture is then evaporated down under reduced pressure and the residue is taken up in methylene chloride. The organic phase is extracted with water, dried over $MgSO_4$ and evaporated down. The residue is purified by column chromatography using hexane/ethyl acetate mixtures. 7.3 g (17 mmol=26%) of the title compound are obtained as a colorless solid.

mp.=87°–89° C. $^1$H-NMR (CDCl$_3$): δ (ppm): 7.55 (d, 2H, J=8 Hz, phenyl); 7.45 (d, 2H, J =8 Hz, phenyl); 4.8 (s, 2H, OCH$_2$); 4.1 (t, 2H, J=8 Hz, phenyl); 4.8 (s, 2H, OCH$_2$); 4.1 (t, 2H, J=5 Hz, OCH$_2$); 3.8 (s, 3H, OCH$_3$); 2.3 (t, 2H, J=6 Hz, CH$_2$); 2.2 (s, 3H, CH$_3$); 2.9 (m, 2H, CH$_2$)

d) Methyl 6-[1'-(4"-bromophenyl)-1'-methyliminoxymeth-4'-yl]-2,3-dihydropyran-5 -ylglyoxylate trans-O-methyloxime (Table 7, No. 26b)

7.3 g (17 mmol) of methyl 6-[1'-(4"-bromophenyl)-1'-methyliminooxymeth-4'-yl]-2,3-dihydropyran-5-ylglyoxylate cis-O-methyloxime (Example 9c), in 20 ml of methylene chloride is exposed to a 300 W UV lamp in an open crystallizing dish for 8 hours. The evaporated solvent is replaced from time to time. Thereafter, 2 ml of a 2N solution of hydrogen chloride in ether are added and exposure is carried out for a further 4 hours. The reaction mixture is then evaporated down under reduced pressure and the residue is purified by column chromatography using hexane/ethyl acetate mixtures. 4 g of starting material and 1.2 g (2.8 mmol =17%) of the title compound are obtained, the latter being in the form of a pale yellow oil.

$^1$H-NMR (CDCl$_3$): δ (ppm): 7.5 (m, 4H, phenyl); 4.5 (s, 2H, OCH$_2$); 4.1 (t, 2H, J=5 Hz, OCH$_2$); 4.0 (s, 3H, OCH$_3$); 3.8 (s, 3H, OCH$_3$); 2.2 (m, 5H, CH$_2$, CH$_3$); 1.95 (m, 2H, CH$_2$)

The compounds listed in the Tables below can be prepared in a similar manner. In the individual tables, I, II and III are to be understood as follows.

In Table I compound no. 1 has the following formula:

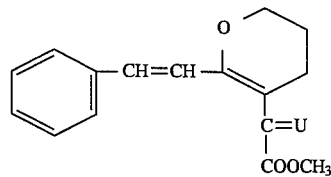

Comopund no. I/1 in Table 1 has the following formula:

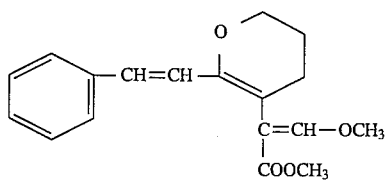

Comopund no. II/1 in Table 1 has the following formula:

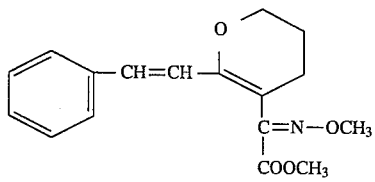

Comopund no. III/1 in Table 1 has the following formula:

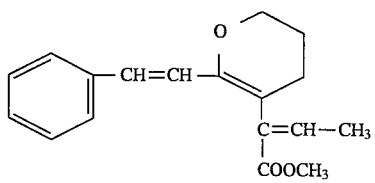

TABLE 1

| No. | $X_m$ |
|---|---|
| 1 | H |
| 2 | 2-F |
| 3 | 3-F |
| 4 | 4-F |
| 5 | 2,3-$F_2$ |
| 6 | 2,4-$F_2$ |
| 7 | 2,5-$F_2$ |
| 8 | 2,6-$F_2$ |
| 9 | 3,4-$F_2$ |
| 10 | 3,5-$F_2$ |
| 11 | 2,3,4-$F_3$ |
| 12 | 2,3,5-$F_3$ |
| 13 | 2,3,6-$F_3$ |
| 14 | 2,4,5-$F_3$ |
| 15 | 2,3,6-$F_3$ |
| 16 | 3,4,5-$F_3$ |
| 17 | 2,3,4,5-$F_4$ |
| 18 | 2,3,4,6-$F_4$ |
| 19 | 2,3,5,6-$F_4$ |
| 20 | 2,3,4,5,6-$F_5$ |
| 21 | 2-Cl |
| 22 | 3-Cl |
| 23 | 4-Cl |
| 24 | 2,3-$Cl_2$ |
| 25 | 2,4-$Cl_2$ |
| 26 | 2,5-$Cl_2$ |
| 27 | 2,6-$Cl_2$ |
| 28 | 3,4-$Cl_2$ |
| 29 | 3,5-$Cl_2$ |
| 30 | 2,3,4-$Cl_3$ |
| 31 | 2,3,5-$Cl_3$ |
| 32 | 2,3,6-$Cl_3$ |
| 33 | 2,4,5-$Cl_3$ |

I: U: =CH—OCH$_3$
II: U: =N—OCH$_3$
III: U: =CH—CH$_3$

TABLE 1-continued

| No. | $X_m$ |
|---|---|
| 34 | 2,4,6-$Cl_3$ |
| 35 | 3,4,5-$Cl_3$ |
| 36 | 2,3,4,5-$Cl_4$ |
| 37 | 2,3,4,6-$Cl_4$ |
| 38 | 2,3,5,6-$Cl_4$ |
| 39 | 2,3,4,5,6-$Cl_5$ |
| 40 | 2-Br |
| 41 | 3-Br |
| 42 | 4-Br |
| 43 | 2,3-$Br_2$ |
| 44 | 2,4-$Br_2$ |
| 45 | 2,5-$Br_2$ |
| 46 | 2,6-$Br_2$ |
| 47 | 3,4-$Br_2$ |
| 48 | 3,5-$Br_2$ |
| 49 | 2,3,4-$Br_3$ |
| 50 | 2,3,5-$Br_3$ |
| 51 | 2,3,6-$Br_3$ |
| 52 | 2,4,5-$Br_3$ |
| 53 | 2,4,6-$Br_3$ |
| 54 | 3,4,5-Br3 |
| 55 | 2,3,4,5-$Br_4$ |
| 56 | 2,3,4,6-$Br_4$ |
| 57 | 2,3,4,6-$Br_4$ |
| 58 | 2,3,4,5,6-$Br_5$ |
| 59 | 2-I |
| 60 | 3-I |
| 61 | 4-I |
| 62 | 2,3-$I_2$ |
| 63 | 2,4-$I_2$ |
| 64 | 2,5-$I_2$ |
| 66 | 2,6-$I_2$ |
| 66 | 3,4-$I_2$ |
| 67 | 3,5-$I_2$ |
| 68 | 2-F, 3-Cl |
| 69 | 2-F, 4-Cl |
| 70 | 2-F, 5-Cl |
| 71 | 2-F, 6-Cl |
| 72 | 2-F, 3-Br |
| 73 | 2-F, 4-Br |
| 74 | 2-F, 5-Br |
| 75 | 2-F, 6-Br |
| 76 | 2-F, 3-I |
| 77 | 2-F, 4-I |
| 78 | 2-F, 5-I |
| 79 | 2-F, 6-I |
| 80 | 2-Cl, 3-Br |
| 81 | 2-Cl, 4-Br |
| 82 | 2-Cl, 5-Br |
| 83 | 2-Cl, 6-Br |
| 84 | 2-Cl, 3-I |
| 85 | 2-Cl, 4-I |
| 86 | 2-Cl, 5-I |
| 87 | 2-Cl, 6-I |
| 88 | 2-Br, 3-I |
| 89 | 2-Br, 4-I |
| 90 | 2-Br, 5-I |
| 91 | 2-Br, 6-I |
| 92 | 3-F, 4-Cl |
| 93 | 3-F, 5-Cl |
| 94 | 3-F, 6-Cl |
| 95 | 3-F, 4-Br |
| 96 | 3-F, 5-Br |
| 97 | 3-F, 6-Br |
| 98 | 3-F, 4-I |
| 99 | 3-F, 5-I |
| 100 | 3-F, 6-I |
| 101 | 3-Cl, 4-Br |
| 102 | 3-Cl, 5-Br |

I: U: =CH—OCH$_3$
II: U: =N—OCH$_3$
III: U: =CH—CH$_3$

TABLE 1-continued

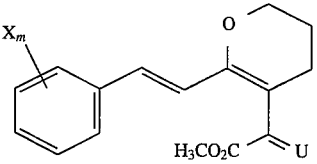

I: U: =CH—OCH$_3$
II: U: =N—OCH$_3$
III: U: =CH—CH$_3$

| No. | X$_m$ |
|---|---|
| 103 | 3-Cl, 6-Br |
| 104 | 3-Cl, 4-I |
| 105 | 3-Cl, 5-I |
| 106 | 3-Cl, 6-I |
| 107 | 3-Br, 4-I |
| 108 | 3-Br, 5-I |
| 109 | 3-Br, 6-I |
| 110 | 4-F, 5-Cl |
| 111 | 4-F, 6-Cl |
| 112 | 4-F, 5-Br |
| 113 | 4-F, 6-Br |
| 114 | 4-F, 5-I |
| 115 | 4-F, 6-I |
| 116 | 4-Cl, 5-Br |
| 117 | 4-Cl, 6-Br |
| 118 | 4-Cl, 5-I |
| 119 | 4-Cl, 6-I |
| 120 | 4-Br, 5-I |
| 121 | 4-Br, 6-I |
| 122 | 5-F, 6-Cl |
| 123 | 5-F, 6-Br |
| 124 | 5-F, 6-I |
| 125 | 5-Cl, 6-Br |
| 126 | 5-Cl, 6-I |
| 127 | 5-Br, 6-I |
| 128 | 2-CH$_3$ |
| 129 | 3-CH$_3$ |
| 130 | 4-CH$_3$ |
| 131 | 2,3-(CH$_3$)$_2$ |
| 132 | 2,4-(CH$_3$)$_2$ |
| 133 | 2,5-(CH$_3$)$_2$ |
| 134 | 2,6-(CH$_3$)$_2$ |
| 135 | 3,4-(CH$_3$)$_2$ |
| 136 | 3,5-(CH$_3$)$_2$ |
| 137 | 2,3,4-(CH$_3$)$_3$ |
| 138 | 2,3,5-(CH$_3$)$_3$ |
| 139 | 2,3,6-(CH$_3$)$_3$ |
| 140 | 2,4,5-(CH$_3$)$_3$ |
| 141 | 2,4,6-(CH$_3$)$_3$ |
| 142 | 3,4,5-(CH$_3$)$_3$ |
| 143 | 2,3,4,5-(CH$_3$)$_4$ |
| 144 | 2,3,4,6-(CH$_3$)$_4$ |
| 145 | 2,3,5,6-(CH$_3$)$_4$ |
| 146 | 2,3,4,5,6-(CH$_3$)$_5$ |
| 147 | 2-C$_2$H$_5$ |
| 148 | 3-C$_2$H$_5$ |
| 149 | 4-C$_2$H$_5$ |
| 150 | 2,4-(C$_2$H$_5$)$_2$ |
| 151 | 2,6-(C$_2$H$_5$)$_2$ |
| 152 | 3,5-(C$_2$H$_5$)$_2$ |
| 153 | 2,4,6-(C$_2$H$_5$)$_3$ |
| 154 | 2-n-C$_3$H$_7$ |
| 155 | 3-n-C$_3$H$_7$ |
| 156 | 4-n-C$_3$H$_7$ |
| 157 | 2-i-C$_3$H$_7$ |
| 158 | 3-i-C$_3$H$_7$ |
| 159 | 4-i-C$_3$H$_7$ |
| 160 | 2,4-(i-C$_3$H$_7$)$_2$ |
| 161 | 3,6-(i-C$_3$H$_7$)$_2$ |
| 162 | 3,5-(i-C$_3$H$_7$)$_2$ |
| 163 | 2,4,6-(i-C$_3$H$_7$)$_3$ |
| 164 | 2-s-C$_4$H$_9$ |
| 165 | 3-s-C$_4$H$_9$t |
| 166 | 4-s-C$_4$H$_9$ |
| 167 | 2-t-C$_4$H$_9$ |
| 168 | 3-t-C$_4$H$_9$ |
| 169 | 4-t-C$_4$H$_9$ |
| 170 | 2,3-(t-C$_4$H$_9$)$_2$ |
| 171 | 2,4-(t-C$_4$H$_9$)$_2$ |

TABLE 1-continued

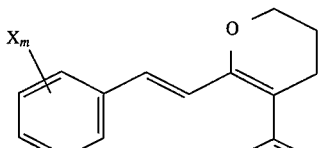

I: U: =CH—OCH$_3$
II: U: =N—OCH$_3$
III: U: =CH—CH$_3$

| No. | X$_m$ |
|---|---|
| 172 | 2,5-(t-C$_4$H$_9$)$_2$ |
| 173 | 2,6-(t-C$_4$H$_9$)$_2$ |
| 174 | 3,4-(t-C$_4$H$_9$)$_2$ |
| 175 | 2,4,6-(t-C$_4$H$_9$)$_3$ |
| 176 | 2-n-C$_4$H$_9$ |
| 177 | 3-n-C$_4$H$_9$ |
| 178 | 4-n-C$_4$H$_9$ |
| 179 | 2-cyclo-C$_6$H$_{11}$ |
| 180 | 3-cyclo-C$_6$H$_{11}$ |
| 181 | 4-cyclo-C$_6$H$_{11}$ |
| 182 | 2-Phenyl |
| 183 | 3-Phenyl |
| 184 | 4-Phenyl |
| 185 | 2-Allyl |
| 186 | 3-Allyl |
| 187 | 4-Allyl |
| 188 | 2-Propargyl |
| 189 | 3-Propargyl |
| 190 | 4-Propargyl |
| 191 | 2-Benzyl |
| 192 | 3-Benzyl |
| 193 | 4-Benzyl |
| 194 | 2-CH$_3$, 3-C$_2$H$_5$ |
| 195 | 2-CH$_3$, 4-C$_2$H$_5$ |
| 196 | 2-CH$_3$, 5-C$_2$H$_5$ |
| 197 | 2-CH$_3$, 6-C$_2$H$_5$ |
| 198 | 2-CH$_3$, 3-i-C$_3$H$_7$ |
| 199 | 2-CH$_3$, 4-i-C$_3$H$_7$ |
| 200 | 2-CH$_3$, 5-i-C$_3$H$_7$ |
| 201 | 2-CH$_3$, 6-i-C$_3$H$_7$ |
| 202 | 2-CH$_3$, 3-n-C$_3$H$_7$ |
| 203 | 2-CH$_3$, 4-n-C$_3$H$_7$ |
| 204 | 2-CH$_3$, 5-n-C$_3$H$_7$ |
| 205 | 2-CH$_3$, 6-n-C$_3$H$_7$ |
| 206 | 2-CH$_3$, 3-n-C$_4$H$_9$ |
| 207 | 2-CH$_3$, 4-n-C$_4$H$_9$ |
| 208 | 2-CH$_3$, 5-n-C$_4$H$_9$ |
| 209 | 2-CH$_3$, 6-n-C$_4$H$_9$ |
| 210 | 2-CH$_3$, 3-s-C$_4$H$_9$ |
| 211 | 2-CH$_3$, 4-s-C$_4$H$_9$ |
| 212 | 2-CH$_3$, 5-s-C$_4$H$_9$ |
| 213 | 2-CH$_3$, 6-s-C$_4$H$_9$ |
| 214 | 2-CH$_3$, 3-i-C$_4$H$_9$ |
| 215 | 2-CH$_3$, 4-i-C$_4$H$_9$ |
| 216 | 2-CH$_3$, 5-i-C$_4$H$_9$ |
| 217 | 2-CH$_3$, 6-i-C$_4$H$_9$ |
| 218 | 2-CH$_3$, 3-t-C$_4$H$_9$ |
| 219 | 2-CH$_3$, 4-t-C$_4$H$_9$ |
| 220 | 2-CH$_3$, 5-t-C$_4$H$_9$ |
| 221 | 2-CH$_3$, 6-t-C$_4$H$_9$ |
| 222 | 2-CH$_3$, 3-cyclo-C$_6$H$_{11}$ |
| 223 | 2-CH$_3$, 4-cyclo-C$_6$H$_{11}$ |
| 224 | 2-CH$_3$, 5-cyclo-C$_6$H$_{11}$ |
| 225 | 2-CH$_3$, 6-cyclo-C$_6$H$_{11}$ |
| 226 | 2-CH$_3$, 3-Benzyl |
| 227 | 2-CH$_3$, 4-Benzyl |
| 228 | 2-CH$_3$, 5-Benzyl |
| 229 | 2-CH$_3$, 6-Benzyl |
| 230 | 2-CH$_3$, 3-Phenyl |
| 231 | 2-CH$_3$, 4-Phenyl |
| 232 | 2-CH$_3$, 5-Phenyl |
| 233 | 2-CH$_3$, 6-Phenyl |
| 234 | 2-CH$_3$, 3-Allyl |
| 235 | 2-CH$_3$, 4-Allyl |
| 236 | 2-CH$_3$, 5-Allyl |
| 237 | 2-CH$_3$, 6-Allyl |
| 238 | 2-CH$_3$, 3-Propargyl |
| 239 | 2-CH$_3$, 4-Propargyl |
| 240 | 2-CH$_3$, 5-Propargyl |

TABLE 1-continued

[Structure: Xm-substituted phenyl-CH=CH- connected to dihydropyran ring with H3CO2C-C(=U) group]

I: U: =CH—OCH3
II: U: =N—OCH3
III: U: =CH—CH3

| No. | Xm |
|---|---|
| 241 | 2-CH3, 6-Propargyl |
| 242 | 3-CH3, 4-C2H5 |
| 243 | 3-CH3, 5-C2H5 |
| 244 | 3-CH3, 6-C2H5 |
| 245 | 3-CH3, 4-i-C3H7 |
| 246 | 3-CH3, 5-i-C3H7 |
| 247 | 3-CH3, 6-i-C3H7 |
| 248 | 3-CH3, 4-n-C3H7 |
| 249 | 3-CH3, 5-n-C3H7 |
| 250 | 3-CH3, 6-n-C3H7 |
| 251 | 3-CH3, 4-n-C4H9 |
| 252 | 3-CH3, 5-n-C4H9 |
| 253 | 3-CH3, 6-n-C4H9 |
| 254 | 3-CH3, 4-s-C4H9 |
| 255 | 3-CH3, 5-s-C4H9 |
| 256 | 3-CH3, 6-s-C4H9 |
| 257 | 3-CH3, 4-i-C4H9 |
| 258 | 3-CH3, 5-i-C4H9 |
| 259 | 3-CH3, 6-i-C4H9 |
| 260 | 3-CH3, 4-t-C4H9 |
| 261 | 3-CH3, 5-t-C4H9 |
| 262 | 3-CH3, 6-t-C4H9 |
| 263 | 3-CH3, 4-cyclo-C6H11 |
| 264 | 3-CH3, 5-cyclo-C6H11 |
| 265 | 3-CH3, 6-cyclo-C6H11 |
| 266 | 3-CH3, 4-Benzyl |
| 267 | 3-CH3, 5-Benzyl |
| 268 | 3-CH3, 6-Benzyl |
| 269 | 3-CH3, 4-Phenyl |
| 270 | 3-CH3, 5-Phenyl |
| 271 | 3-CH3, 6-Phenyl |
| 272 | 3-CH3, 4-Allyl |
| 273 | 3-CH3, 5-Allyl |
| 274 | 3-CH3, 6-Allyl |
| 275 | 3-CH3, 4-Propargyl |
| 276 | 3-CH3, 5-Propargyl |
| 277 | 3-CH3, 6-Propargyl |
| 278 | 4-CH3, 5-C2H5 |
| 279 | 4-CH3, 6-C2H5 |
| 280 | 4-CH3, 5-i-C3H7 |
| 281 | 4-CH3, 6-i-C3H7 |
| 282 | 4-CH3, 5-n-C3H7 |
| 283 | 4-CH3, 6-n-C3H7 |
| 284 | 4-CH3, 5-n-C4H9 |
| 285 | 4-CH3, 6-n-C4H9 |
| 286 | 4-CH3, 5-s-C4H9 |
| 287 | 4-CH3, 6-s-C4H9 |
| 288 | 4-CH3, 5-i-C4H9 |
| 289 | 4-CH3, 6-i-C4H9 |
| 290 | 4-CH3, 5-t-C4H9 |
| 291 | 4-CH3, 6-t-C4H9 |
| 292 | 4-CH3, 5-cyclo-C6H11 |
| 293 | 4-CH3, 6-cyclo-C6H11 |
| 294 | 4-CH3, 5-Benzyl |
| 295 | 4-CH3, 6-Benzyl |
| 296 | 4-CH3, 5-Phenyl |
| 297 | 4-CH3, 6-Phenyl |
| 298 | 4-CH3, 5-Allyl |
| 299 | 4-CH3, 6-Allyl |
| 300 | 4-CH3, 5-Propargyl |
| 301 | 4-CH3, 6-Propargyl |
| 302 | 5-CH3, 6-C2H5 |
| 303 | 5-CH3, 6-i-C3H7 |
| 304 | 5-CH3, 6-n-C3H7 |
| 305 | 5-CH3, 6-n-C4H9 |
| 306 | 5-CH3, 6-s-C4H9 |
| 307 | 5-CH3, 6-i-C4H9 |
| 308 | 5-CH3, 6-t-C4H9 |
| 309 | 5-CH3, 6-cyclo-C4H9 |
| 310 | 5-CH3, 6-Benzyl |
| 311 | 5-CH3, 6-Phenyl |
| 312 | 5-CH3, 6-Allyl |
| 313 | 5-CH3, 6-Propargyl |
| 314 | 2-OCH3 |
| 315 | 3-OCH3 |
| 316 | 4-OCH3 |
| 317 | 2-OC2H5 |
| 318 | 3-O—C2H5 |
| 319 | 4-O—C2H5 |
| 320 | 2-O-n-C3H7 |
| 321 | 3-O-n-C3H7 |
| 322 | 4-O-n-C3H7 |
| 323 | 2-O-i-C3H7 |
| 324 | 3-O-i-C3H7 |
| 325 | 4-O-i-C3H7 |
| 326 | 2-O-n-C4H9 |
| 327 | 3-O-n-C4H9 |
| 328 | 4-O-n-C4H9 |
| 329 | 2-O-s-C4H9 |
| 330 | 3-O-s-C4H9 |
| 331 | 4-O-s-C4H9 |
| 332 | 2-O-i-C4H9 |
| 333 | 3-O-i-C4H9 |
| 334 | 4-O-i-C4H9 |
| 335 | 2-O-t-C4H9 |
| 336 | 3-O-t-C4H9 |
| 337 | 4-O-t-C4H9 |
| 338 | 2-O-n-C6H13 |
| 339 | 3-O-n-C6H13 |
| 340 | 4-O-n-C6H13 |
| 341 | 2-O-n-C8H17 |
| 342 | 3-O-n-C8H17 |
| 343 | 4-O-n-C8H17 |
| 344 | 2-O—CH2C6H5 |
| 345 | 3-O—CH2C6H5 |
| 346 | 4-O—CH2C6H5 |
| 347 | 2-O—(CH2)3C6H5 |
| 348 | 3-O—(CH2)3C6H5 |
| 349 | 4-O—(CH2)3C6H5 |
| 350 | 2,3-(OCH3)2 |
| 351 | 2,4-(OCH3)2 |
| 352 | 2,5-(OCH3)2 |
| 353 | 2,6-(OCH3)2 |
| 354 | 3,4-(OCH3)2 |
| 355 | 3,5-(OCH3)2 |
| 356 | 2-CF3 |
| 357 | 3-CF3 |
| 358 | 4-CF3 |
| 359 | 2-OCF3 |
| 360 | 3-OCF3 |
| 361 | 4-OCF3 |
| 362 | 2-OCH2CHF2 |
| 363 | 3-OCH2CHF3 |
| 364 | 4-OCH2CHF2 |
| 365 | 2-NO2 |
| 366 | 3-NO2 |
| 367 | 4-NO2 |
| 368 | 2-CN |
| 369 | 3-CN |
| 370 | 4-CN |
| 371 | 2-OC6H5 |
| 372 | 3-OC6H5 |
| 373 | 4-OC6H5 |
| 374 | 2-O-(2'-F—C6H4) |
| 375 | 2-O-(3'-F—C6H4) |
| 376 | 2-O-(4'-F—C6H4) |
| 377 | 3-O-(2'-F—C6H4) |
| 378 | 3-O-(3'-F—C6H4) |

TABLE 1-continued

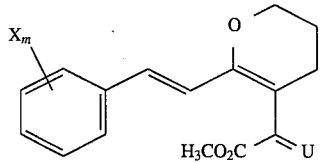

I: U: =CH—OCH$_3$
II: U: =N—OCH$_3$
III: U: =CH—CH$_3$

| No. | X$_m$ |
|---|---|
| 379 | 3-O-(4'-F—C$_6$H$_4$) |
| 380 | 4-O-(2'-F—C$_6$H$_4$) |
| 381 | 4-O-(3'-F—C$_6$H$_4$) |
| 382 | 4-O-(4'-F—C$_6$H$_4$) |
| 383 | 2-O-(2'-Cl—C$_6$H$_4$) |
| 384 | 2-O-(3'-Cl—C$_6$H$_4$) |
| 385 | 2-O-(4'-Cl—C$_6$H$_4$) |
| 386 | 3-O-(2'-Cl—C$_6$H$_4$) |
| 387 | 3-O-(3'-Cl—C$_6$H$_4$) |
| 388 | 3-O-(4'-Cl—C$_6$H$_4$) |
| 389 | 4-O-(2'-Cl—C$_6$H$_4$) |
| 390 | 4-O-(3'-Cl—C$_6$H$_4$) |
| 391 | 4-O-(4'-Cl—C$_6$H$_4$) |
| 392 | 2-O-(2'-CH$_3$—C$_6$H$_4$) |
| 393 | 2-O-(3'-CH$_3$—C$_6$H$_4$) |
| 394 | 2-O-(4'-CH$_3$—C$_6$H$_4$) |
| 395 | 3-O-(2'-CH$_3$—C$_6$H$_4$) |
| 396 | 3-O-(3'-CH$_3$—C$_6$H$_4$) |
| 397 | 3-O-(4'-CH$_3$—C$_6$H$_4$) |
| 398 | 4-O-(2'-CH$_3$—C$_6$H$_4$) |
| 399 | 4-O-(3'-CH$_3$—C$_6$H$_4$) |
| 400 | 4-O-(4'-CH$_3$—C$_6$H$_4$) |
| 401 | 2-O-(2'-CH$_3$—CO—C$_6$H$_4$) |
| 402 | 2-O-(3'-CH$_3$—CO—C$_6$H$_4$) |
| 403 | 2-O-(4'-CH$_3$—CO—C$_6$H$_4$) |
| 404 | 3-O-(2'-CH$_3$—CO—C$_6$H$_4$) |
| 405 | 3-O-(3'-CH$_3$—CO—C$_6$H$_4$) |
| 406 | 3-O-(4'-CH$_3$—CO—C$_6$H$_4$) |
| 407 | 4-O-(2'-CH$_3$—CO—C$_6$H$_4$) |
| 408 | 4-O-(3'-CH$_3$—CO—C$_6$H$_4$) |
| 409 | 4-O-(4'-CH$_3$—CO—C$_6$H$_4$) |
| 410 | 2-O-(2'-(CH$_3$—C(=NOAllyl))-C$_6$H$_4$) |
| 411 | 2-O-(3'-(CH$_3$—C(=NOAllyl))-C$_6$H$_4$) |
| 412 | 2-O-(4'-(CH$_3$—C(=NOAllyl))-C$_6$H$_4$) |
| 413 | 3-O-(2'-(CH$_3$—C(=NOAllyl))-C$_6$H$_4$) |
| 414 | 3-O-(3'-(CH$_3$—C(=NOAllyl))-C$_6$H$_4$) |
| 415 | 3-O-(4'-(CH$_3$—C(=NOAllyl))-C$_6$H$_4$) |
| 416 | 4-O-(2'-(CH$_3$—C(=NOAllyl))-C$_6$H$_4$) |
| 417 | 4-O-(3'-(CH$_3$—C(=NOAllyl))-C$_6$H$_4$) |
| 418 | 4-O-(4'-(CH$_3$—C(=NOAllyl))-C$_6$H$_4$) |
| 419 | 2-O-(2'-CH$_3$O$_2$C—C$_6$H$_4$) |
| 420 | 2-O-(3'-CH$_3$O$_2$C—C$_6$H$_4$) |
| 421 | 2-O-(4'-CH$_3$O$_2$C—C$_6$H$_4$) |
| 422 | 3-O-(2'-CH$_3$O$_2$C—C$_6$H$_4$) |
| 423 | 3-O-(3'-CH$_3$O$_2$C—C$_6$H$_4$) |
| 424 | 3-O-(4'-CH$_3$O$_2$C—C$_6$H$_4$) |
| 425 | 4-O-(2'-CH$_3$O$_2$C—C$_6$H$_4$) |
| 426 | 4-O-(3'-CH$_3$O$_2$C—C$_6$H$_4$) |
| 427 | 4-O-(4'-CH$_3$O$_2$C—C$_6$H$_4$) |
| 428 | 2-O-(2'-CH$_3$O—C$_6$H$_4$) |
| 429 | 2-O-(3'-CH$_3$O—C$_6$H$_4$) |
| 430 | 2-O-(4'-CH$_3$O—C$_6$H$_4$) |
| 431 | 3-O-(2'-CH$_3$O—C$_6$H$_4$) |
| 432 | 3-O-(3'-CH$_3$O—C$_6$H$_4$) |
| 433 | 3-O-(4'-CH$_3$O—C$_6$H$_4$) |
| 434 | 4-O-(2'-CH$_3$O—C$_6$H$_4$) |
| 435 | 4-O-(3'-CH$_3$O—C$_6$H$_4$) |
| 436 | 4-O-(4'-CH$_3$O—C$_6$H$_4$) |
| 437 | 2-O-(2'-O$_2$N—C$_6$H$_4$) |
| 438 | 2-O-(3'-O$_2$N—C$_6$H$_4$) |
| 439 | 2-O-(4'-O$_2$N—C$_6$H$_4$) |
| 440 | 3-O-(2'-O$_2$N—C$_6$H$_4$) |
| 441 | 3-O-(3'-O$_2$N—C$_6$H$_4$) |
| 442 | 3-O-(4'-O$_2$N—C$_6$H$_4$) |
| 443 | 4-O-(2'-O$_2$N—C$_6$H$_4$) |
| 444 | 4-O-(3'-O$_2$N—C$_6$H$_4$) |
| 445 | 4-O-(4'-O$_2$N—C$_6$H$_4$) |
| 446 | 2-O-(2'-NC—C$_6$H$_4$) |
| 447 | 2-O-(3'-NC—C$_6$H$_4$) |

TABLE 1-continued

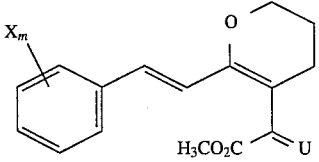

I: U: =CH—OCH$_3$
II: U: =N—OCH$_3$
III: U: =CH—CH$_3$

| No. | X$_m$ |
|---|---|
| 448 | 2-O-(4'-NC—C$_6$H$_4$) |
| 449 | 3-O-(2'-NC—C$_6$H$_4$) |
| 450 | 3-O-(3'-NC—C$_6$H$_4$) |
| 451 | 3-O-(4'-NC—C$_6$H$_4$) |
| 452 | 4-O-(2'-NC—C$_6$H$_4$) |
| 453 | 4-O-(3'-NC—C$_6$H$_4$) |
| 454 | 4-O-(4'-NC—C$_6$H$_4$) |
| 455 | 2-O-(2'-CF$_3$—C$_6$H$_4$) |
| 456 | 2-O-(3'-CF$_3$—C$_6$H$_4$) |
| 457 | 2-O-(4'-CF$_3$—C$_6$H$_4$) |
| 458 | 3-O-(2'-CF$_3$—C$_6$H$_4$) |
| 459 | 3-O-(3'-CF$_3$—C$_6$H$_4$) |
| 460 | 3-O-(4'-CF$_3$—C$_6$H$_4$) |
| 461 | 4-O-(2'-CF$_3$—C$_6$H$_4$) |
| 462 | 4-O-(3'-CF$_3$—C$_6$H$_4$) |
| 463 | 4-O-(4'-CF$_3$—C$_6$H$_4$) |
| 464 | 2-O-(2'-F$_3$CO—C$_6$H$_4$) |
| 465 | 2-O-(3'-F$_3$CO—C$_6$H$_4$) |
| 466 | 2-O-(4'-F$_3$CO—C$_6$H$_4$) |
| 467 | 3-O-(2'-F$_3$CO—C$_6$H$_4$) |
| 468 | 3-O-(3'-F$_3$CO—C$_6$H$_4$) |
| 469 | 3-O-(4'-F$_3$CO—C$_6$H$_4$) |
| 470 | 4-O-(2'-F$_3$CO—C$_6$H$_4$) |
| 471 | 4-O-(3'-F$_3$CO—C$_6$H$_4$) |
| 472 | 4-O-(4'-F$_3$CO—C$_6$H$_4$) |
| 473 | 2-CO$_2$CH$_3$ |
| 474 | 3-CO$_2$CH$_3$ |
| 475 | 4-CO$_2$CH$_3$ |
| 476 | 2-CO$_2$(C$_2$H$_5$) |
| 477 | 3-CO$_2$(C$_2$H$_5$) |
| 478 | 4-CO$_2$(C$_2$H$_5$) |
| 479 | 2-CO$_2$(n-C$_3$H$_7$) |
| 480 | 3-CO$_2$(n-C$_3$H$_7$) |
| 481 | 4-CO$_2$(n-C$_3$H$_7$) |
| 482 | 2-CO$_2$(i-C$_3$H$_7$) |
| 483 | 3-CO$_2$(i-C$_3$H$_7$) |
| 484 | 4-CO$_2$(i-C$_3$H$_7$) |
| 485 | 2-CO$_2$(n-C$_6$H$_{13}$) |
| 486 | 3-CO$_2$(n-C$_6$H$_{13}$) |
| 487 | 4-CO$_2$(n-C$_6$H$_{13}$) |
| 488 | 2-CO$_2$(n-C$_8$H$_{17}$) |
| 489 | 3-CO$_2$(n-C$_8$H$_{17}$) |
| 490 | 4-CO$_2$(n-C$_8$H$_{17}$) |
| 491 | 2-CH$_2$—OCH$_3$ |
| 492 | 3-CH$_2$—OCH$_3$ |
| 493 | 4-CH$_2$—OCH$_3$ |
| 494 | 2-CH$_2$O(C$_2$H$_5$) |
| 495 | 3-CH$_2$O(C$_2$H$_5$) |
| 496 | 4-CH$_2$O(C$_2$H$_5$) |
| 497 | 2-CH$_2$O(n-C$_3$H$_7$) |
| 498 | 3-CH$_2$O(n-C$_3$H$_7$) |
| 499 | 4-CH$_2$O(n-C$_3$H$_7$) |
| 500 | 2-CH$_2$O(i-C$_3$H$_7$) |
| 501 | 3-CH$_2$O(i-C$_3$H$_7$) |
| 502 | 4-CH$_2$O(i-C$_3$H$_7$) |
| 503 | 2-CH$_2$O(n-C$_6$H$_{13}$) |
| 504 | 3-CH$_2$O(n-C$_6$H$_{13}$) |
| 505 | 4-CH$_2$O(n-C$_6$H$_{13}$) |
| 506 | 2-CH$_2$O(n-C$_8$H$_{17}$) |
| 507 | 3-CH$_2$O(n-C$_8$H$_{17}$) |
| 508 | 4-CH$_2$O(n-C$_8$H$_{17}$) |
| 509 | 2-CH$_2$OCH$_2$(C$_6$H$_5$) |
| 510 | 3-CH$_2$OCH$_2$(C$_6$H$_5$) |
| 511 | 4-CH$_2$OCH$_2$(C$_6$H$_5$) |
| 512 | 2-CH$_2$O(CH$_2$)$_3$(C$_6$H$_5$) |
| 513 | 3-CH$_2$O(CH$_2$)$_3$(C$_6$H$_5$) |
| 514 | 4-CH$_2$O(CH$_2$)$_3$(C$_6$H$_5$) |
| 515 | 2-CHO |
| 516 | 3-CHO |

TABLE 1-continued

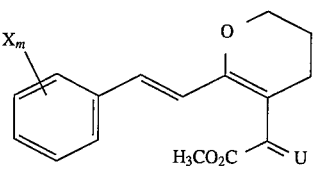

I: U: =CH—OCH₃
II: U: =N—OCH₃
III: U: =CH—CH₃

| No. | $X_m$ |
|---|---|
| 517 | 4-CHO |
| 518 | 2-CO—CH₃ |
| 519 | 3-CO—CH₃ |
| 520 | 4-CO—CH₃ |
| 521 | 2-CO—CH₂—CH₃ |
| 522 | 3-CO—CH₂—CH₃ |
| 523 | 4-CO—CH₂—CH₃ |
| 524 | 2-CO—CH₂—CH₂—CH₃ |
| 525 | 3-CO—CH₂—CH₂—CH₃ |
| 526 | 4-CO—CH₂—CH₂—CH₃ |
| 527 | 2-CO—CH(CH₃)—CH₃ |
| 528 | 3-CO—CH(CH₃)—CH₃ |
| 529 | 4-CO—CH(CH₃)—CH₃ |
| 530 | 2-Me-4-CHO |
| 531 | 2-Me-4-CH₃—CO |
| 532 | 2-Me-4-CH₃—CH₂—CO |
| 533 | 2-Me-4-CH₃—CH₂—CH₂—CO |
| 534 | 2-Me-4-CH₃—CH(CH₃)—CO |
| 535 | 2,5-Me₂-4-CHO |
| 536 | 2,5-Me₂-4-CH₃—CO |
| 537 | 2,5-Me₂-4-CH₃—CH₂—CO |
| 538 | 2,5-Me₂-4-CH₃—CH₂—CH₂—CO |
| 539 | 2,5-Me₂-4-CH₃—CH(CH₃)—CO |
| 540 | 2-Cl-4-CHO |
| 541 | 2-Cl-4-CH₃—CO |
| 542 | 2-Cl-4-CH₃—CH₂—CO |
| 543 | 2-Cl-4-CH₃—CH(CH₃)—CO |
| 544 | 2,5-Cl₂-4-CHO |
| 546 | 2,5-Cl₂-4-CH₃—CO |
| 547 | 2,4-Cl₂-4-CH₃—CH₂—CO |
| 548 | 2,5-Cl₂-4-CH₃—CH₂—CH₂—CO |
| 549 | 2,5-Cl₂-4-CH₃—CH(CH₃)—CO |
| 550 | 2-CH=NOCH₃ |
| 551 | 3-CH=NOCH₃ |
| 552 | 4-CH=NOCH₃ |
| 553 | 2-CH=NOC₂H₅ |
| 554 | 3-CH=NOC₂H₅ |
| 555 | 4-CH=NOC₂H₅ |
| 556 | 2-CH=NO-i-C₃H₇ |
| 557 | 3-CH=NO-i-C₃H₇ |
| 558 | 4-CH=NO-i-C₃H₇ |
| 559 | 2-CH=NO-Allyl |
| 560 | 3-CH=NO-Allyl |
| 561 | 4-CH=NO-Allyl |
| 562 | 2-CH=NO-trans-chloroalkyl |
| 563 | 3-CH=NO-trans-chloroalkyl |
| 564 | 4-CH=NO-trans-chloroalkyl |
| 565 | 2-CH=NO-Propargyl |
| 566 | 3-CH=NO-Propargyl |
| 567 | 4-CH=NO-Propargyl |
| 568 | 2-CH=NO—CH₂—C₆H₅ |
| 569 | 3-CH=NO—CH₂—C₆H₅ |
| 570 | 4-CH=NO—CH₂—C₆H₅ |
| 571 | 2-C(=NOCH₃)—CH₃ |
| 572 | 3-C(=NOCH₃)—CH₃ |
| 573 | 4-C(=NOCH₃)—CH₃ |
| 574 | 2-C(=NOC₂H₅)—CH₃ |
| 575 | 3-C(=NOC₂H₅)—CH₃ |
| 576 | 4-C(=NOC₂H₅)—CH₃ |
| 577 | 2-C(=NO-i-C₃H₇)—CH₃ |
| 578 | 3-C(=NO-i-C₃H₇)—CH₃ |
| 579 | 4-C(=NO-i-C₃H₇)—CH₃ |
| 580 | 2-C(=NO-Allyl)—CH₃ |
| 581 | 3-C(=NO-Allyl)—CH₃ |
| 582 | 4-C(=NO-Allyl)—CH₃ |
| 583 | 2-C(=NO-trans-chloroallyl)—CH₃ |
| 584 | 3-C(=NO-trans-chloroallyl)—CH₃ |
| 585 | 4-C(=NO-trans-chloroallyl)—CH₃ |
| 586 | 2-C(=NO-Propargyl)—CH₃ |
| 587 | 3-C(=NO-Propargyl)—CH₃ |
| 588 | 4-C(=NO-Propargyl)—CH₃ |
| 589 | 2-C(=NO—CH₂—C₆H₅)—CH₃ |
| 590 | 3-C(=NO—CH₂—C₆H₅)—CH₃ |
| 591 | 4-C(=NO—CH₂—C₆H₅)—CH₃ |
| 592 | 2-C(=NOCH₃)—C₂H₅ |
| 593 | 3-C(=NOCH₃)—C₂H₅ |
| 594 | 4-C(=NOCH₃)—C₂H₅ |
| 595 | 2-C(=NOC₂H₅)—C₂H₅ |
| 596 | 3-C(=NOC₂H₅)—C₂H₅ |
| 597 | 4-C(=NOC₂H₅)—C₂H₅ |
| 598 | 2-C(=NO-i-C₃H₇)—C₂H₅ |
| 599 | 3-C(=NO-i-C₃H₇)—C₂H₅ |
| 600 | 4-C(=NO-i-C₃H₇)—C₂H₅ |
| 601 | 2-C(=NO-Allyl)—C₂H₅ |
| 602 | 3-C(=NO-Allyl)—C₂H₅ |
| 603 | 4-C(=NO-Allyl)—C₂H₅ |
| 604 | 2-C(=NO-trans-chloroallyl)—C₂H₅ |
| 605 | 3-C(=NO-trans-chloroallyl)—C₂H₅ |
| 606 | 4-C(=NO-trans-chloroallyl)—C₂H₅ |
| 607 | 2-C(=NO-Propargyl)—C₂H₅ |
| 608 | 3-C(=NO-Propargyl)—C₂H₅ |
| 609 | 4-C(=NO-Propargyl)—C₂H₅ |
| 610 | 2-C(=NO—CH₂—C₆H₅)—C₂H₅ |
| 611 | 3-C(=NO—CH₂—C₆H₅)—C₂H₅ |
| 612 | 4-C(=NO—CH₂—C₆H₅)—C₂H₅ |
| 613 | 2-C(=NOCH₃)-n-C₃H₇ |
| 614 | 3-C(=NOCH₃)-n-C₃H₇ |
| 615 | 4-C(=NOCH₃)-n-C₃H₇ |
| 616 | 2-C(=NOC₂H₅)-n-C₃H₇ |
| 617 | 3-C(=NOC₂H₅)-n-C₃H₇ |
| 618 | 4-C(=NOC₂H₅)-n-C₃H₇ |
| 619 | 2-C(=NO-i-C₃H₇)-n-C₃H₇ |
| 620 | 3-C(=NO-i-C₃H₇)-n-C₃H₇ |
| 621 | 4-C(=NO-i-C₃H₇)-n-C₃H₇ |
| 622 | 2-C(=NO-Allyl)-n-C₃H₇ |
| 623 | 3-C(=NO-Allyl)-n-C₃H₇ |
| 624 | 4-C(=NO-Allyl)-n-C₃H₇ |
| 625 | 2-C(=NO-trans-chloroallyl)-n-C₃H₇ |
| 626 | 3-C(=NO-trans-chloroallyl)-n-C₃H₇ |
| 627 | 4-C(=NO-trans-chloroallyl)-n-C₃H₇ |
| 628 | 2-C(=NO-Propargyl)-n-C₃H₇ |
| 629 | 3-C(=NO-Propargyl)-n-C₃H₇ |
| 630 | 4-C(=NO-Propargyl)-n-C₃H₇ |
| 631 | 2-C(=NO—CH₂—C₆H₅)-n-C₃H₇ |
| 632 | 3-C(=NO—CH₂—C₆H₅)-n-C₃H₇ |
| 633 | 4-C(=NO—CH₂—C₆H₅)-n-C₃H₇ |
| 634 | 2-C(=NOCH₃)-i-C₃H₇ |
| 635 | 3-C(=NOCH₃)-i-C₃H₇ |
| 636 | 4-C(=NOCH₃)-i-C₃H₇ |
| 637 | 2-C(=NOC₂H₅)-i-C₃H₇ |
| 638 | 3-C(=NOC₂H₅)-i-C₃H₇ |
| 639 | 4-C(=NOC₂H₅)-i-C₃H₇ |
| 640 | 2-C(=NO-i-C₃H₇)-i-C₃H₇ |
| 641 | 3-C(=NO-i-C₃H₇)-i-C₃H₇ |
| 642 | 4-C(=NO-i-C₃H₇)-i-C₃H₇ |
| 643 | 2-C(=NO-Allyl)-i-C₃H₇ |
| 644 | 3-C(=NO-Allyl)-i-C₃H₇ |
| 645 | 4-C(=NO-Allyl)-i-C₃H₇ |
| 646 | 2-C(=NO-trans-chloroallyl)-i-C₃H₇ |
| 647 | 3-C(=NO-trans-chloroallyl)-i-C₃H₇ |
| 648 | 4-C(=NO-trans-chloroallyl)-i-C₃H₇ |
| 649 | 2-C(=NO-Propargyl)-i-C₃H₇ |
| 650 | 3-C(=NO-Propargyl)-i-C₃H₇ |
| 651 | 4-C(=NO-Propargyl)-i-C₃H₇ |
| 652 | 2-C(=NO—CH₂—C₆H₅)-i-C₃H₇ |
| 653 | 3-C(=NO—CH₂—C₆H₅)-i-C₃H₇ |
| 654 | 4-C(=NO—CH₂—C₆H₅)-i-C₃H₇ |
| 655 | 2-CH₃-4-CH=NOCH₃ |

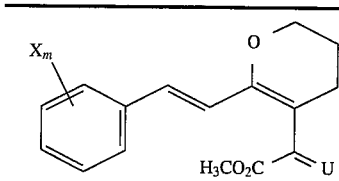

TABLE 1-continued

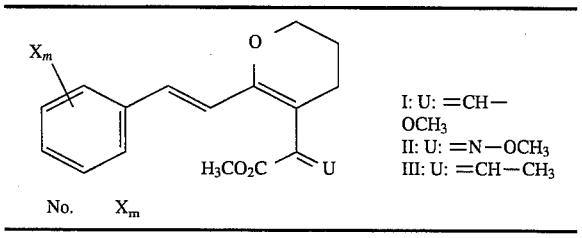

I: U: =CH—OCH$_3$
II: U: =N—OCH$_3$
III: U: =CH—CH$_3$

| No. | X$_m$ |
|---|---|
| 656 | 2-CH$_3$-4-CH=NOC$_2$H$_5$ |
| 657 | 2-CH$_3$-4-CH=NO-i-C$_3$H$_7$ |
| 658 | 2-CH$_3$-4-CH=NO-Allyl |
| 659 | 2-CH$_3$-4-CH=NO-(trans-chloroallyl) |
| 660 | 2-CH$_3$-4-CH=NO-Propargyl |
| 661 | 2-CH$_3$-4-CH=NO—CH$_2$—C$_6$H$_5$ |
| 662 | 2-CH$_3$-4-(CH$_3$—C=NOCH$_3$) |
| 663 | 2-CH$_3$-4-(CH$_3$—C=NOC$_2$H$_5$) |
| 664 | 2-CH$_3$-4-(CH$_3$—C=NO-i-C$_3$H$_7$) |
| 665 | 2-CH$_3$-4-(CH$_3$—C=NO-Allyl) |
| 666 | 2-CH$_3$-4-(CH$_3$—C=NO-trans-chloroallyl) |
| 667 | 2-CH$_3$-4-(CH$_3$—C=NO-Propargyl) |
| 668 | 2-CH$_3$-4-(CH$_3$—C=NO—CH$_2$—C$_6$H$_5$) |
| 669 | 2-CH$_3$-4-(C$_2$H$_5$—C=NO—CH$_3$) |
| 670 | 2-CH$_3$-4-(C$_2$H$_5$—C=NO—C$_2$H$_5$) |
| 671 | 2-CH$_3$-4-(C$_2$H$_5$—C=NO-i-C$_3$H$_7$) |
| 672 | 2-CH$_3$-4-(C$_2$H$_5$—C=NO-Allyl) |
| 673 | 2-CH$_3$-4-(C$_2$H$_5$—C=NO-trans-chloroallyl) |
| 674 | 2-CH$_3$-4-(C$_2$H$_5$—C=NO-Propargyl) |
| 675 | 2-CH$_3$-4-(C$_2$H$_5$—C=NO—CH$_2$—C$_6$H$_5$) |
| 676 | 2-CH$_3$-4-(n-C$_3$H$_7$—C=NOCH$_3$) |
| 677 | 2-CH$_3$-4-(n-C$_3$H$_7$—C=NOC$_2$H$_5$) |
| 678 | 2-CH$_3$-4-(n-C$_3$H$_7$—C=NO-i-C$_3$H$_7$) |
| 679 | 2-CH$_3$-4-(n-C$_3$H$_7$—C=NO-Allyl) |
| 680 | 2-CH$_3$-4-(n-C$_3$H$_7$—C=NO-trans-chloroallyl) |
| 681 | 2-CH$_3$-4-(n-C$_3$H$_7$—C=NO-Propargyl) |
| 682 | 2-CH$_3$-4-(n-C$_3$H$_7$—C=NO—CH$_2$—C$_6$H$_5$) |
| 683 | 2-CH$_3$-4-(i-C$_3$H$_7$—C=NOCH$_3$) |
| 684 | 2-CH$_3$-4-(i-C$_3$H$_7$—C=NOC$_2$H$_5$) |
| 685 | 2-CH$_3$-4-(i-C$_3$H$_7$—C=NO-i-C$_3$H$_7$) |
| 686 | 2-CH$_3$-4-(i-C$_3$H$_7$—C=NO-Allyl) |
| 687 | 2-CH$_3$-4-(i-C$_3$H$_7$—C=NO-trans-chloroallyl) |
| 688 | 2-CH$_3$-4-(i-C$_3$H$_7$—C=NO-Propargyl) |
| 689 | 2-CH$_3$-4-(i-C$_3$H$_7$—C=NO—CH$_2$—C$_6$H$_5$) |
| 690 | 2,5-(CH$_3$)$_2$-4-(CH=NOCH$_3$) |
| 691 | 2,5-(CH$_3$)$_2$-4-(CH=NOC$_2$H$_5$) |
| 692 | 2,5-(CH$_3$)$_2$-4-(CH=NO-i-C$_3$H$_7$) |
| 693 | 2,5-(CH$_3$)$_2$-4-(CH=NO-Allyl) |
| 694 | 2,5-(CH$_3$)$_2$-4-(CH=NO-trans-chloroallyl) |
| 695 | 2,5-(CH$_3$)$_2$-4-(CH=NO-Propargyl) |
| 696 | 2,5-(CH$_3$)$_2$-4-(CH=NO—CH$_2$—C$_6$H$_5$) |
| 697 | 2,5-(CH$_3$)$_2$-4-(CH$_3$—C=NOCH$_3$) |
| 698 | 2,5-(CH$_3$)$_2$-4-(CH$_3$—C=NOC$_2$H$_5$) |
| 699 | 2,5-(CH$_3$)$_2$-4-(CH$_3$—C=NO-i-C$_3$H$_7$) |
| 700 | 2,5-(CH$_3$)$_2$-4-(CH$_3$—C=NO-Allyl) |
| 701 | 2,5-(CH$_3$)$_2$-4-(CH$_3$—C=NO-trans-chloroallyl) |
| 702 | 2,5-(CH$_3$)$_2$-4-(CH$_3$—C=NO-Propargyl) |
| 703 | 2,5-(CH$_3$)$_2$-4-(CH$_3$—C=NO—CH$_2$—C$_6$H$_5$) |
| 704 | 2,5-(CH$_3$)$_2$-4-(C$_2$H$_5$—C=NOCH$_3$) |
| 705 | 2,5-(CH$_3$)$_2$-4-(C$_2$H$_5$—C=NOC$_2$H$_5$) |
| 706 | 2,5-(CH$_3$)$_2$-4-(C$_2$H$_5$—C=NO-i-C$_3$H$_7$) |
| 707 | 2,5-(CH$_3$)$_2$-4-(C$_2$H$_5$—C=NO-Allyl) |
| 708 | 2,5-(CH$_3$)$_2$-4-(C$_2$H$_5$—C=NO-trans-chloroallyl) |
| 709 | 2,5-(CH$_3$)$_2$-4-(C$_2$H$_5$—C=NO-Propargyl) |
| 710 | 2,5-(CH$_3$)$_2$-4-(C$_2$H$_5$—C=NO—CH$_2$—C$_6$H$_5$) |
| 711 | 2,5-(CH$_3$)$_2$-4-(n-C$_3$H$_7$—CH=NOCH$_3$) |
| 712 | 2,5-(CH$_3$)$_2$-4-(n-C$_3$H$_7$—CH=NOC$_2$H$_5$) |
| 713 | 2,5-(CH$_3$)$_2$-4-(n-C$_3$H$_7$—CH=NO-i-C$_3$H$_7$) |
| 714 | 2,5-(CH$_3$)$_2$-4-(n-C$_3$H$_7$—CH=NO-Allyl) |
| 715 | 2,5-(CH$_3$)$_2$-4-(n-C$_3$H$_7$—CH=NO-trans-chloroallyl) |
| 716 | 2,5-(CH$_3$)$_2$-4-(n-C$_3$H$_7$—CH=NO-Propargyl) |
| 717 | 2,5-(CH$_3$)$_2$-4-(n-C$_3$H$_7$—CH=NO—CH$_2$—C$_6$H$_5$) |
| 718 | 2,5-(CH$_3$)$_2$-4-(i-C$_3$H$_7$—CH=NOCH$_3$) |
| 719 | 2,5-(CH$_3$)$_2$-4-(i-C$_3$H$_7$—CH=NOC$_2$H$_5$) |
| 720 | 2,5-(CH$_3$)$_2$-4-(i-C$_3$H$_7$—CH=NO-i-C$_3$H$_7$) |
| 721 | 2,5-(CH$_3$)$_2$-4-(i-C$_3$H$_7$—CH=NO-Allyl) |
| 722 | 2,5-(CH$_3$)$_2$-4-(i-C$_3$H$_7$—CH=NO-trans-chloroallyl) |
| 723 | 2,5-(CH$_3$)$_2$-4-(i-C$_3$H$_7$—CH=NO-Propargyl) |
| 724 | 2,5-(CH$_3$)$_2$-4-(i-C$_3$H$_7$—CH=NO—CH$_2$—C$_6$H$_5$) |

TABLE 1-continued

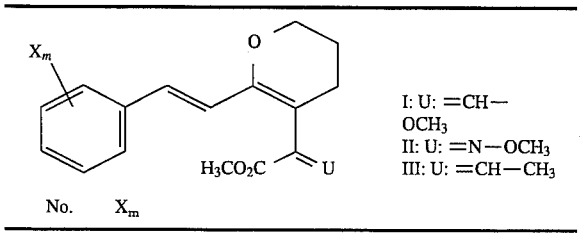

I: U: =CH—OCH$_3$
II: U: =N—OCH$_3$
III: U: =CH—CH$_3$

| No. | X$_m$ |
|---|---|
| 725 | 2-Cl-4-CH=NOCH$_3$ |
| 726 | 2-Cl-4-CH=NOC$_2$H$_5$ |
| 727 | 2-Cl-4-CH=NO-i-C$_3$H$_7$ |
| 728 | 2-Cl-4-CH=NO-Allyl |
| 729 | 2-Cl-4-CH=NO-trans-chloroallyl |
| 730 | 2-Cl-4-CH=NO-Propargyl |
| 731 | 2-Cl-4-CH=NO—CH$_2$—C$_6$H$_5$ |
| 732 | 2-Cl-4-(CH$_3$—C=NOCH$_3$) |
| 733 | 2-Cl-4-(CH$_3$—C=NOC$_2$H$_5$) |
| 734 | 2-Cl-4-(CH$_3$—C=NO-i-C$_3$H$_7$) |
| 735 | 2-Cl-4-(CH$_3$—C=NO-Allyl) |
| 736 | 2-Cl-4-(CH$_3$—C=NO-trans-chloroallyl) |
| 737 | 2-Cl-4-(CH$_3$—C=NO-Propargyl) |
| 738 | 2-Cl-4-(CH$_3$—C=NO—CH$_2$—C$_6$H$_5$) |
| 739 | 2-Cl-4-(C$_2$H$_5$—C=NOCH$_3$) |
| 740 | 2-Cl-4-(C$_2$H$_5$—C=NOC$_2$H$_5$) |
| 741 | 2-Cl-4-(C$_2$H$_5$—C=NO-i-C$_3$H$_7$) |
| 742 | 2-Cl-4-(C$_2$H$_5$—C=NO-Allyl) |
| 743 | 2-Cl-4-(C$_2$H$_5$—C=NO-trans-chloroallyl) |
| 744 | 2-Cl-4-(C$_2$H$_5$—C=NO-Propargyl) |
| 745 | 2-Cl-4-(C$_2$H$_5$—C=NO—CH$_2$—C$_6$H$_5$) |
| 746 | 2-Cl-4-(n-C$_3$H$_7$—C=NOCH$_3$) |
| 747 | 2-Cl-4-(n-C$_3$H$_7$—C=NOC$_2$H$_5$) |
| 748 | 2-Cl-4-(n-C$_3$H$_7$—C=NO-i-C$_3$H$_7$) |
| 749 | 2-Cl-4-(n-C$_3$H$_7$—C=NO-Allyl) |
| 750 | 2-Cl-4-(n-C$_3$H$_7$—C=NO-trans-chloroallyl) |
| 751 | 2-Cl-4-(n-C$_3$H$_7$—C=NO-Propargyl) |
| 752 | 2-Cl-4-(n-C$_3$H$_7$—C=NO—CH$_2$—C$_6$H$_5$) |
| 753 | 2-Cl-4-(i-C$_3$H$_7$—C=NOCH$_3$) |
| 754 | 2-Cl-4-(i-C$_3$H$_7$—C=NOC$_2$H$_5$) |
| 755 | 2-Cl-4-(i-C$_3$H$_7$—C=NO-i-C$_3$H$_7$) |
| 756 | 2-Cl-4-(i-C$_3$H$_7$—C=NO-Allyl) |
| 757 | 2-Cl-4-(i-C$_3$H$_7$—C=NO-trans-chloroallyl) |
| 758 | 2-Cl-4-(i-C$_3$H$_7$—C=NO-Propargyl) |
| 759 | 2-Cl-4-(i-C$_3$H$_7$—C=NO—CH$_2$—C$_6$H$_5$) |
| 760 | 2,5-Cl$_2$-4-CH=NOCH$_3$ |
| 761 | 2,5-Cl$_2$-4-CH=NOC$_2$H$_5$ |
| 762 | 2,5-Cl$_2$-4-CH=NO-i-C$_3$H$_7$ |
| 763 | 2,5-Cl$_2$-4-CH=NO-Allyl |
| 764 | 2,5-Cl$_2$-4-CH=NO-trans-chloroallyl |
| 765 | 2,5-Cl$_2$-4-CH=NO-Propargyl |
| 766 | 2,5-Cl$_2$-4-CH=NO—CH$_2$C$_6$H$_5$ |
| 767 | 2,5-Cl$_2$-4-(CH$_3$—C=NOCH$_3$) |
| 768 | 2,5-Cl$_2$-4-(CH$_3$—C=NOC$_2$H$_5$) |
| 769 | 2,5-Cl$_2$-4-(CH$_3$—C=NO-i-C$_3$H$_7$) |
| 770 | 2,5-Cl$_2$-4-(CH$_3$—C=NO-Allyl) |
| 771 | 2,5-Cl$_2$-4-(CH$_3$—C=NO-trans-chloroallyl) |
| 772 | 2,5-Cl$_2$-4-(CH$_3$—C=NO-Propargyl) |
| 773 | 2,5-Cl$_2$-4-(CH$_3$—C=NO—CH$_2$—C$_6$H$_5$) |
| 774 | 2,5-Cl$_2$-4-(C$_2$H$_5$—C=NO—CH$_3$) |
| 775 | 2,5-Cl$_2$-4-(C$_2$H$_5$—C=NO—C$_2$H$_5$) |
| 776 | 2,5-Cl$_2$-4-(C$_2$H$_5$—C=NO-i-C$_3$H$_7$) |
| 777 | 2,5-Cl$_2$-4-(C$_2$H$_5$—C=NO-Allyl) |
| 778 | 2,5-Cl$_2$-4-(C$_2$H$_5$—C=NO-trans-chloroallyl) |
| 779 | 2,5-Cl$_2$-4-(C$_2$H$_5$—C=NO-Propargyl) |
| 780 | 2,5-Cl$_2$-4-(C$_2$H$_5$—C=NO—CH$_2$—C$_6$H$_5$) |
| 781 | 2,5-Cl$_2$-4-(n-C$_3$H$_7$—C=NOCH$_3$) |
| 782 | 2,5-Cl$_2$-4-(n-C$_3$H$_7$—C=NOC$_2$H$_5$) |
| 783 | 2,5-Cl$_2$-4-(n-C$_3$H$_7$—C=NO-i-C$_3$H$_7$) |
| 784 | 2,5-Cl$_2$-4-(n-C$_3$H$_7$—C=NO-Allyl) |
| 785 | 2,5-Cl$_2$-4-(n-C$_3$H$_7$—C=NO-trans-chloroallyl) |
| 786 | 2,5-Cl$_2$-4-(n-C$_3$H$_7$—C=NO-Propargyl) |
| 787 | 2,5-Cl$_2$-4-(n-C$_3$H$_7$—C=NO—CH$_2$C$_6$H$_5$) |
| 788 | 2,5-Cl$_2$-4-(i-C$_3$H$_7$—C=NOCH$_3$) |
| 789 | 2,5-Cl$_2$-4-(i-C$_3$H$_7$—C=NOC$_2$H$_5$) |
| 790 | 2,5-Cl$_2$-4-(i-C$_3$H$_7$—C=NO-i-C$_3$H$_7$) |
| 791 | 2,5-Cl$_2$-4-(i-C$_3$H$_7$—C=NO-Allyl) |
| 792 | 2,5-Cl$_2$-4-(i-C$_3$H$_7$—C=NO-trans-chloroallyl) |
| 793 | 2,5-Cl$_2$-4-(i-C$_3$H$_7$—C=NO-Propargyl) |

TABLE 1-continued

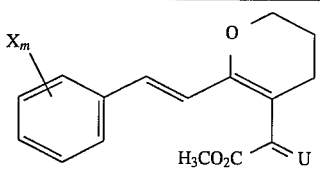

I: U: =CH—OCH$_3$
II: U: =N—OCH$_3$
III: U: =CH—CH$_3$

| No. | X$_m$ |
|---|---|
| 794 | 2,5-Cl$_2$-4-(i-C$_3$H$_7$—C=NO—CH$_2$—C$_6$H$_5$) |
| 795 | 2-Pyridinyl-2' |
| 796 | 2-Pyridinyl-3' |
| 797 | 2-Pyridinyl-4' |
| 798 | 3-Pyridinyl-2' |
| 799 | 3-Pyridinyl-3' |
| 800 | 3-Pyridinyl-4' |
| 801 | 4-Pyridinyl-2' |
| 802 | 4-Pyridinyl-3' |
| 803 | 4-Pyridinyl-4' |
| 804 | 2-Pyrimidinyl-2' |
| 805 | 2-Pyrimidinyl-3' |
| 806 | 2-Pyrimidinyl-4' |
| 807 | 3-Pyrimidinyl-2' |
| 808 | 3-Pyrimidinyl-3' |
| 809 | 3-Pyrimidinyl-4' |
| 810 | 4-Pyrimidinyl-2' |
| 811 | 4-Pyrimidinyl-3' |
| 812 | 4-Pyrimidinyl-4' |
| 813 | 2-Pyrazolyl-1' |
| 814 | 2-Pyrazolyl-3' |
| 815 | 2-Pyrazolyl-4' |
| 816 | 3-Pyrazolyl-1' |
| 817 | 3-Pyrazolyl-3' |
| 818 | 3-Pyrazolyl-4' |
| 819 | 4-Pyrazolyl-1' |
| 820 | 4-Pyrazolyl-3' |
| 821 | 4-Pyrazolyl-4' |
| 822 | 2-Isoxazolyl-3' |
| 823 | 2-Isoxazolyl-4' |
| 824 | 2-Isoxazolyl-5' |
| 825 | 3-Isoxazolyl-3' |
| 826 | 3-Isoxazolyl-4' |
| 827 | 3-Isoxazolyl-5' |
| 828 | 4-Isoxazolyl-3' |
| 829 | 4-Isoxazolyl-4' |
| 830 | 4-Isoxazolyl-5' |
| 831 | 2-Isothiazolyl-3' |
| 832 | 2-Isothiazolyl-4' |
| 833 | 2-Isothiazolyl-5' |
| 834 | 3-Isothiazolyl-3' |
| 835 | 3-Isothiazolyl-4' |
| 836 | 3-Isothiazolyl-5' |
| 837 | 4-Isothiazolyl-3' |
| 838 | 4-Isothiazolyl-4' |
| 839 | 4-Isothiazolyl-5' |
| 840 | 2-Imidazolyl-1' |
| 841 | 2-Imidazolyl-2' |
| 842 | 2-Imidazolyl-4' |
| 843 | 3-Imidazolyl-1' |
| 844 | 3-Imidazolyl-2' |
| 845 | 3-Imidazolyl-4' |
| 846 | 4-Imidazolyl-1' |
| 847 | 4-Imidazolyl-2' |
| 848 | 4-Imidazolyl-4' |
| 849 | 2-Oxazolyl-2' |
| 850 | 2-Oxazolyl-4' |
| 851 | 2-Oxazolyl-5' |
| 852 | 3-Oxazolyl-2' |
| 853 | 3-Oxazolyl-4' |
| 854 | 3-Oxazolyl-5' |
| 855 | 4-Oxazolyl-2' |
| 856 | 4-Oxazolyl-4' |
| 857 | 4-Oxazolyl-5' |
| 858 | 2-Thiazolyl-2' |
| 859 | 2-Thiazolyl-4' |
| 860 | 2-Thiazolyl-5' |
| 861 | 3-Thiazolyl-2' |
| 862 | 3-Thiazolyl-4' |
| 863 | 3-Thiazolyl-5' |
| 864 | 4-Thiazolyl-2' |
| 865 | 4-Thiazolyl-4' |
| 866 | 4-Thiazolyl-5' |
| 867 | 2-Cl-3-CH$_3$ |
| 868 | 2-Cl-4-CH$_3$ |
| 869 | 2-Cl-5-CH$_3$ |
| 870 | 2-Cl-6-CH$_3$ |
| 871 | 3-Cl-4-CH$_3$ |
| 872 | 3-Cl-5-CH$_3$ |
| 873 | 3-Cl-6-CH$_3$ |
| 874 | 4-Cl-5-CH$_3$ |
| 875 | 4-Cl-6-CH$_3$ |
| 876 | 5-Cl-6-CH$_3$ |
| 877 | 2-Cl-3-t-C$_4$H$_9$ |
| 878 | 2-Cl-4-t-C$_4$H$_9$ |
| 879 | 2-Cl-5-t-C$_4$H$_9$ |
| 880 | 2-Cl-6-t-C$_4$H$_9$ |
| 881 | 3-Cl-4-t-C$_4$H$_9$ |
| 882 | 3-Cl-5-t-C$_4$H$_9$ |
| 883 | 3-Cl-6-t-C$_4$H$_9$ |
| 884 | 4-Cl-5-t-C$_4$H$_9$ |
| 885 | 4-Cl-6-t-C$_4$H$_9$ |
| 886 | 5-Cl-6-t-C$_4$H$_9$ |
| 887 | 2-Cl-3-cyclo-C$_6$H$_{11}$ |
| 888 | 2-Cl-4-cyclo-C$_6$H$_{11}$ |
| 889 | 2-Cl-5-cyclo-C$_6$H$_{11}$ |
| 890 | 2-Cl-6-cyclo-C$_6$H$_{11}$ |
| 891 | 3-Cl-4-cyclo-C$_6$H$_{11}$ |
| 892 | 3-Cl-5-cyclo-C$_6$H$_{11}$ |
| 893 | 3-Cl-6-cyclo-C$_6$H$_{11}$ |
| 894 | 4-Cl-5-cyclo-C$_6$H$_{11}$ |
| 895 | 4-Cl-6-cyclo-C$_6$H$_{11}$ |
| 896 | 5-Cl-6-cyclo-C$_6$H$_{11}$ |
| 897 | 2-Cl-3-Benzyl |
| 898 | 2-Cl-4-Benzyl |
| 899 | 2-Cl-5-Benzyl |
| 900 | 2-Cl-6-Benzyl |
| 901 | 3-Cl-4-Benzyl |
| 902 | 3-Cl-5-Benzyl |
| 903 | 3-Cl-6-Benzyl |
| 904 | 4-Cl-5-Benzyl |
| 905 | 4-Cl-6-Benzyl |
| 906 | 5-Cl-6-Benzyl |
| 907 | 2-Cl-3-Phenyl |
| 908 | 2-Cl-4-Phenyl |
| 909 | 2-Cl-5-Phenyl |
| 910 | 2-Cl-6-Phenyl |
| 911 | 3-Cl-4-Phenyl |
| 912 | 3-Cl-5-Phenyl |
| 913 | 3-Cl-6-Phenyl |
| 914 | 4-Cl-5-Phenyl |
| 915 | 4-Cl-6-Phenyl |
| 916 | 5-Cl-6-Phenyl |
| 917 | 2-Cl-3-CH$_3$O |
| 918 | 2-Cl-4-CH$_3$O |
| 919 | 2-Cl-5-CH$_3$O |
| 920 | 2-Cl-6-CH$_3$O |
| 921 | 3-Cl-4-CH$_3$O |
| 922 | 3-Cl-5-CH$_3$O |
| 923 | 3-Cl-6-CH$_3$O |
| 924 | 4-Cl-5-CH$_3$O |
| 925 | 4-Cl-6-CH$_3$O |
| 926 | 5-Cl-6-CH$_3$O |
| 927 | 2-Br-3-CH$_3$ |
| 928 | 2-Br-4-CH$_3$ |
| 929 | 2-Br-5-CH$_3$ |
| 930 | 2-Br-6-CH$_3$ |
| 931 | 3-Br-4-CH$_3$ |

TABLE 1-continued

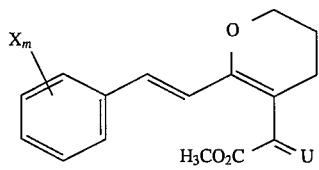

I: U: =CH—OCH$_3$
II: U: =N—OCH$_3$
III: U: =CH—CH$_3$

| No. | X$_m$ |
|---|---|
| 932 | 3-Br-5-CH$_3$ |
| 933 | 3-Br-6-CH$_3$ |
| 934 | 4-Br-5-CH$_3$ |
| 935 | 4-Br-6-CH$_3$ |
| 936 | 5-Br-6-CH$_3$ |
| 937 | 2-Br-3-t-C$_4$H$_9$ |
| 938 | 2-Br-4-t-C$_4$H$_9$ |
| 939 | 2-Br-5-t-C$_4$H$_9$ |
| 940 | 2-Br-6-t-C$_4$H$_9$ |
| 941 | 3-Br-4-t-C$_4$H$_9$ |
| 942 | 3-Br-5-t-C$_4$H$_9$ |
| 943 | 3-Br-6-t-C$_4$H$_9$ |
| 944 | 4-Br-5-t-C$_4$H$_9$ |
| 945 | 4-Br-6-t-C$_4$H$_9$ |
| 946 | 5-Br-6-t-C$_4$H$_9$ |
| 947 | 2-Br-3-cyclo-C$_6$H$_{11}$ |
| 948 | 2-Br-4-cyclo-C$_6$H$_{11}$ |
| 949 | 2-Br-5-cyclo-C$_6$H$_{11}$ |
| 950 | 2-Br-6-cyclo-C$_6$H$_{11}$ |
| 951 | 3-Br-4-cyclo-C$_6$H$_{11}$ |
| 952 | 3-Br-5-cyclo-C$_6$H$_{11}$ |
| 953 | 3-Br-6-cyclo-C$_6$H$_{11}$ |
| 954 | 4-Br-5-cyclo-C$_6$H$_{11}$ |
| 955 | 4-Br-6-cyclo-C$_6$H$_{11}$ |
| 956 | 5-Br-6-cyclo-C$_6$H$_{11}$ |
| 957 | 2-Br-3-Benzyl |
| 958 | 2-Br-4-Benzyl |
| 959 | 2-Br-5-Benzyl |
| 960 | 2-Br-6-Benzyl |
| 961 | 3-Br-4-Benzyl |
| 962 | 3-Br-5-Benzyl |
| 963 | 3-Br-6-Benzyl |
| 964 | 4-Br-5-Benzyl |
| 965 | 4-Br-6-Benzyl |
| 966 | 5-Br-6-Benzyl |
| 967 | 2-Br-3-Phenyl |
| 968 | 2-Br-4-Phenyl |
| 969 | 2-Br-5-Phenyl |
| 970 | 2-Br-6-Phenyl |
| 971 | 3-Br-4-Phenyl |
| 972 | 3-Br-5-Phenyl |
| 973 | 3-Br-6-Phenyl |
| 974 | 4-Br-5-Phenyl |
| 975 | 4-Br-6-Phenyl |
| 976 | 5-Br-6-Phenyl |
| 977 | 2-Br-3-CH$_3$O |
| 978 | 2-Br-4-CH$_3$O |
| 979 | 2-Br-5-CH$_3$O |
| 980 | 2-Br-6-CH$_3$O |
| 981 | 3-Br-4-CH$_3$O |
| 982 | 3-Br-5-CH$_3$O |
| 983 | 3-Br-6-CH$_3$O |
| 984 | 4-Br-5-CH$_3$O |
| 985 | 4-Br-6-CH$_3$O |
| 986 | 5-Br-6-CH$_3$O |
| 987 | 2-CH$_3$-3-CH$_3$O |
| 988 | 2-CH$_3$-4-CH$_3$O |
| 989 | 2-CH$_3$-5-CH$_3$O |
| 990 | 2-CH$_3$-6-CH$_3$O |
| 991 | 3-CH$_3$-4-CH$_3$O |
| 992 | 3-CH$_3$-5-CH$_3$O |
| 993 | 3-CH$_3$-6-CH$_3$O |
| 994 | 4-CH$_3$-5-CH$_3$O |
| 995 | 4-CH$_3$-6-CH$_3$O |
| 996 | 5-CH$_3$-6-CH$_3$O |
| 997 | 2-t-C$_4$H$_9$-3-CH$_3$O |
| 998 | 2-t-C$_4$H$_9$-4-CH$_3$O |
| 999 | 2-t-C$_4$H$_9$-5-CH$_3$O |
| 1000 | 2-t-C$_4$H$_9$-6-CH$_3$O |

TABLE 1-continued

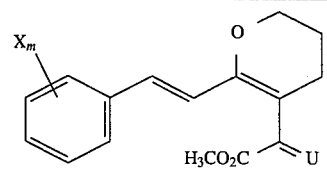

I: U: =CH—OCH$_3$
II: U: =N—OCH$_3$
III: U: =CH—CH$_3$

| No. | X$_m$ |
|---|---|
| 1001 | 3-t-C$_4$H$_9$-4-CH$_3$O |
| 1002 | 3-t-C$_4$H$_9$-5-CH$_3$O |
| 1003 | 3-t-C$_4$H$_9$-6-CH$_3$O |
| 1004 | 4-t-C$_4$H$_9$-5-CH$_3$O |
| 1005 | 4-t-C$_4$H$_9$-6-CH$_3$O |
| 1006 | 5-t-C$_4$H$_9$-6-CH$_3$O |
| 1007 | 2-cyclo-C$_6$H$_{11}$-3-CH$_3$O |
| 1008 | 2-cyclo-C$_6$H$_{11}$-4-CH$_3$O |
| 1009 | 2-cyclo-C$_6$H$_{11}$-5-CH$_3$O |
| 1010 | 2-cyclo-C$_6$H$_{11}$-6-CH$_3$O |
| 1011 | 3-cyclo-C$_6$H$_{11}$-4-CH$_3$O |
| 1012 | 3-cyclo-C$_6$H$_{11}$-5-CH$_3$O |
| 1013 | 3-cyclo-C$_6$H$_{11}$-6-CH$_3$O |
| 1014 | 4-cyclo-C$_6$H$_{11}$-5-CH$_3$O |
| 1015 | 4-cyclo-C$_6$H$_{11}$-6-CH$_3$O |
| 1016 | 5-cyclo-C$_6$H$_{11}$-6-CH$_3$O |
| 1017 | 2-Benzyl-3-CH$_3$O |
| 1018 | 2-Benzyl-4-CH$_3$O |
| 1019 | 2-Benzyl-5-CH$_3$O |
| 1020 | 2-Benzyl-6-CH$_3$O |
| 1021 | 3-Benzyl-4-CH$_3$O |
| 1022 | 3-Benzyl-5-CH$_3$O |
| 1023 | 3-Benzyl-6-CH$_3$O |
| 1024 | 4-Benzyl-5-CH$_3$O |
| 1025 | 4-Benzyl-6-CH$_3$O |
| 1026 | 5-Benzyl-6-CH$_3$O |
| 1027 | 2-Phenyl-3-CH$_3$O |
| 1028 | 2-Phenyl-4-CH$_3$O |
| 1029 | 2-Phenyl-5-CH$_3$O |
| 1030 | 2-Phenyl-6-CH$_3$O |
| 1031 | 3-Phenyl-4-CH$_3$O |
| 1032 | 3-Phenyl-5-CH$_3$O |
| 1033 | 3-Phenyl-6-CH$_3$O |
| 1034 | 4-Phenyl-5-CH$_3$O |
| 1035 | 4-Phenyl-6-CH$_3$O |
| 1036 | 5-Phenyl-6-CH$_3$O |
| 1037 | 2,4-(t-C$_4$H$_9$)$_2$-6-i-C$_3$H$_7$ |
| 1038 | 2,4-(cyclo-C$_6$H$_{11}$)$_2$-6-CH$_3$ |
| 1039 | 4-C$_6$H$_5$-2,5-(CH$_3$)$_2$ |
| 1040 | 2-Cl-4,5-(CH$_3$)$_2$ |
| 1041 | 2-Br-4,5-(CH$_3$)$_2$ |
| 1042 | 2-Cl-3,5-(CH$_3$)$_2$ |
| 1043 | 2-Br-3,5-(CH$_3$)$_2$ |
| 1044 | 2,6-Cl$_2$-4-CH$_3$ |
| 1045 | 2,6-F$_2$-4-CH$_3$ |
| 1046 | 2,6-Br$_2$-4-CH$_3$ |
| 1047 | 2,4-Cl$_2$-6-CH$_3$ |
| 1048 | 2,4-F$_2$-6-CH$_3$ |
| 1049 | 2,4-Br$_2$-6-CH$_3$ |
| 1050 | 2,6-(CH$_3$)$_2$-4-F |
| 1051 | 2,6-(CH$_3$)$_2$-4-Cl |
| 1052 | 2,6-(CH$_3$)$_2$-4-Br |
| 1053 | 3,5-(CH$_3$)$_2$-4-F |
| 1054 | 3,5-(CH$_3$)$_2$-4-Cl |
| 1055 | 3,5-(CH$_3$)$_2$-4-Br |
| 1056 | 2,3,6-(CH$_3$)$_3$-4-F |
| 1057 | 2,3,6-(CH$_3$)$_3$-4-Cl |
| 1058 | 2,3,6-(CH$_3$)$_3$-4-Br |
| 1059 | 2,4-(CH$_3$)$_2$-6-F |
| 1060 | 2,4-(CH$_3$)$_2$-6-Cl |
| 1061 | 2,4-(CH$_3$)$_2$-6-Br |
| 1062 | 2-i-C$_3$H$_7$-4-Cl-5-CH$_3$ |
| 1063 | 2-Cl-4-NO$_2$ |
| 1064 | 2-NO$_2$-4-Cl |
| 1065 | 2-OCH$_3$-5-NO$_2$ |
| 1066 | 2,4-Cl$_2$-5-NO$_2$ |
| 1067 | 2,4-Cl$_2$-6-NO$_2$ |
| 1068 | 2,6-Cl$_2$-4-NO$_2$ |
| 1069 | 2,6-Br$_2$-4-NO$_2$ |

TABLE 1-continued $X_m$—(phenyl)—CH=CH—(dihydropyran with $H_3CO_2C$—C(=U)— substituent)

I: U: =CH—OCH$_3$
II: U: =N—OCH$_3$
III: U: =CH—CH$_3$

| No. | $X_m$ |
|---|---|
| 1070 | 2,6-I$_2$-4-NO$_2$ |
| 1071 | 2-CH$_3$-5-i-C$_3$H$_7$ 4-Cl |
| 1072 | 2-SCH$_3$ |
| 1073 | 3-SCH$_3$ |
| 1074 | 4-SCH$_3$ |
| 1075 | 2-S—C$_6$H$_5$ |
| 1076 | 3-S—C$_6$H$_5$ |
| 1077 | 4-S—C$_6$H$_5$ |
| 1078 | 2-S(=O)—CH$_3$ |
| 1079 | 3-S(=O)—CH$_3$ |
| 1080 | 4-S(=O)—CH$_3$ |
| 1081 | 2-S(=O)—C$_6$H$_5$ |
| 1082 | 3-S(=O)—C$_6$H$_5$ |
| 1083 | 4-S(=O)—C$_6$H$_5$ |
| 1084 | 2-SO$_2$—CH$_3$ |
| 1085 | 3-SO$_2$—CH$_3$ |
| 1086 | 4-SO$_2$—CH$_3$ |
| 1087 | 2-SO$_2$—C$_6$H$_5$ |
| 1088 | 3-SO$_2$—C$_6$H$_5$ |
| 1089 | 4-SO$_2$—C$_6$H$_5$ |

TABLE 2

R—CH=CH—(dihydropyran with $H_3CO_2C$—C(=U)— substituent)

I: U: =CH—OCH$_3$
II: U: =N—OCH$_3$
III: U: =CH—CH$_3$

| No. | R |
|---|---|
| 1 | N—CH$_3$-Pyrryl-3 |
| 2 | N-i-C$_3$H$_7$-Pyrryl-2 |
| 3 | N-t-C$_4$H$_9$-Pyrryl-3 |
| 4 | N-cyclo-C$_3$H$_9$-Pyrryl-3 |
| 5 | N—C$_6$H$_5$-Pyrryl-3 |
| 6 | N-(4'-CH$_3$—C$_6$H$_4$)-Pyrryl-3 |
| 7 | N-(3'-CH$_3$—C$_6$H$_4$)-Pyrryl-3 |
| 8 | N-(2'-CH$_3$—C$_6$H$_4$)-Pyrryl-3 |
| 9 | N-(4'-CH$_3$O—C$_6$H$_4$)-Pyrryl-3 |
| 10 | N-(3'-CH$_3$O—C$_6$H$_4$)-Pyrryl-3 |
| 11 | N-(2'-CH$_3$O—C$_6$H$_4$)-Pyrryl-3 |
| 12 | N-(4'-NO$_2$—C$_6$H$_4$)-Pyrryl-3 |
| 13 | N-(3'-NO$_2$—C$_6$H$_4$)-Pyrryl-3 |
| 14 | N-(2'-NO$_2$—C$_6$H$_4$)-Pyrryl-3 |
| 15 | N-(4'-CN—C$_6$H$_4$)-Pyrryl-3 |
| 16 | N-(3'-CN—C$_6$H$_4$)-Pyrryl-3 |
| 17 | N-(2'-CN—C$_6$H$_4$)-Pyrryl-3 |
| 18 | N-(4'-CF$_3$—C$_6$H$_4$)-Pyrryl-3 |
| 19 | N-(3'-CF$_3$—C$_6$H$_4$)-Pyrryl-3 |
| 20 | N-(2'-CF$_3$—C$_6$H$_4$)-Pyrryl-3 |
| 21 | N-(4'-t-C$_4$H$_9$—C$_6$H$_4$)-Pyrryl-3 |
| 22 | N-(3'-t-C$_4$H$_9$—C$_6$H$_4$)-Pyrryl-3 |
| 23 | N-(2'-t-C$_4$H$_9$—C$_6$H$_4$)-Pyrryl-3 |
| 24 | N-(4'-C$_6$H$_5$—C$_6$H$_4$)-Pyrryl-3 |
| 25 | N-(3'-C$_6$H$_5$—C$_6$H$_4$)-Pyrryl-3 |
| 26 | N-(2'-C$_6$H$_5$—C$_6$H$_4$)-Pyrryl-3 |
| 27 | N-(4'-Cl—C$_6$H$_4$)-Pyrryl-3 |
| 28 | N-(3'-Cl—C$_6$H$_4$)-Pyrryl-3 |
| 29 | N-(2'-Cl—C$_6$H$_4$)-Pyrryl-3 |
| 30 | N-(4'-Br—C$_6$H$_4$)-Pyrryl-3 |
| 31 | N-(3'-Br—C$_6$H$_4$)-Pyrryl-3 |
| 32 | N-(2'-Br—C$_6$H$_4$)-Pyrryl-3 |
| 33 | N-(4'-F—C$_6$H$_4$)-Pyrryl-3 |
| 34 | N-(3'-F—C$_6$H$_4$)-Pyrryl-3 |

TABLE 2-continued

| No. | R |
|---|---|
| 35 | N-(2'-F—C$_6$H$_4$)-Pyrryl-3 |
| 36 | N-(3',4'-Cl$_2$—C$_6$H$_3$)-Pyrryl-3 |
| 37 | N-(2',4'-Cl$_2$—C$_6$H$_3$)-Pyrryl-3 |
| 38 | N-(3',4'-F$_2$—C$_6$H$_3$)-Pyrryl-3 |
| 39 | N-(2',4'-F$_2$—C$_6$H$_3$)-Pyrryl-3 |
| 40 | N-(2',6'-F$_2$—C$_6$H$_3$)-Pyrryl-3 |
| 41 | N-(5'-Cl-2'-CH$_3$O—C$_6$H$_3$)-Pyrryl-3 |
| 42 | N—CH$_3$-Pyrryl-2 |
| 43 | N-i-C$_3$H$_7$-Pyrryl-2 |
| 44 | N-t-C$_4$H$_9$-Pyrryl-2 |
| 45 | N-cyclo-C$_3$H$_5$-Pyrryl-2 |
| 46 | N—C$_6$H$_5$-Pyrryl-2 |
| 47 | N-(4'-CH$_3$—C$_6$H$_4$)-Pyrryl-2 |
| 48 | N-(3'-CH$_3$—C$_6$H$_4$)-Pyrryl-2 |
| 49 | N-(2'-CH$_3$—C$_6$H$_4$)-Pyrryl-2 |
| 50 | N-(4'-CH$_3$O—C$_6$H$_4$)-Pyrryl-2 |
| 51 | N-(3'-CH$_3$O—C$_6$H$_4$)-Pyrryl-2 |
| 52 | N-(2'-CH$_3$O—C$_6$H$_4$)-Pyrryl-2 |
| 53 | N-(4'-NO$_2$—C$_6$H$_4$)-Pyrryl-2 |
| 54 | N-(3'-NO$_2$—C$_6$H$_4$)-Pyrryl-2 |
| 55 | N-(2'-NO$_2$—C$_6$H$_4$)-Pyrryl-2 |
| 56 | N-(4'-CN—C$_6$H$_4$)-Pyrryl-2 |
| 57 | N-(3'-CN—C$_6$H$_4$)-Pyrryl-2 |
| 58 | N-(2'-CN—C$_6$H$_4$)-Pyrryl-2 |
| 59 | N-(4'-CF$_3$—C$_6$H$_4$)-Pyrryl-2 |
| 60 | N-(3'-CF$_3$—C$_6$H$_4$)-Pyrryl-2 |
| 61 | N-(2'-CF$_3$—C$_6$H$_4$)-Pyrryl-2 |
| 62 | N-(4'-t-C$_4$H$_9$—C$_6$H$_4$)-Pyrryl-2 |
| 63 | N-(3'-t-C$_4$H$_9$—C$_6$H$_4$)-Pyrryl-2 |
| 64 | N-(2'-t-C$_4$H$_9$—C$_6$H$_4$)-Pyrryl-2 |
| 65 | N-(4'-C$_6$H$_5$—C$_6$H$_4$)-Pyrryl-2 |
| 66 | N-(3'-C$_6$H$_5$—C$_6$H$_4$)-Pyrryl-2 |
| 67 | N-(2'-C$_6$H$_5$—C$_6$H$_4$)-Pyrryl-2 |
| 68 | N-(4'-Cl—C$_6$H$_4$)-Pyrryl-2 |
| 69 | N-(3'-Cl—C$_6$H$_4$)-Pyrryl-2 |
| 70 | N-(2'-Cl—C$_6$H$_4$)-Pyrryl-2 |
| 71 | N-(4'-Br—C$_6$H$_4$)-Pyrryl-2 |
| 72 | N-(3'-Br—C$_6$H$_4$)-Pyrryl-2 |
| 73 | N-(2'-Br—C$_6$H$_4$)-Pyrryl-2 |
| 74 | N-(4'-F—C$_6$H$_4$)-Pyrryl-2 |
| 75 | N-(3'-F—C$_6$H$_4$)-Pyrryl-2 |
| 76 | N-(2'-F—C$_6$H$_4$)-Pyrryl-2 |
| 77 | N-(3',4'-Cl$_2$—C$_6$H$_3$)-Pyrryl-2 |
| 78 | N-(2',4'-Cl$_2$—C$_6$H$_3$)-Pyrryl-2 |
| 79 | N-(3',4'-F$_2$—C$_6$H$_3$)-Pyrryl-2 |
| 80 | N-(2',4'-F$_2$—C$_6$H$_3$)-Pyrryl-2 |
| 81 | N-(2',6'-F$_2$—C$_6$H$_3$)-Pyrryl-2 |
| 82 | N-(5'-Cl-2'-CH$_3$O—C$_6$H$_5$)-Pyrryl-2 |
| 83 | 5-CH$_3$-Furyl-2 |
| 84 | 5-i-C$_3$H$_7$-Furyl-2 |
| 85 | 5-t-C$_4$H$_9$-Furyl-2 |
| 86 | 5-cyclo-C$_3$H$_5$-Furyl-2 |
| 87 | 5-C$_6$H$_5$-Furyl-2 |
| 88 | 5-(4'-CH$_3$—C$_6$H$_4$)-Furyl-2 |
| 89 | 5-(3'-CH$_3$—C$_6$H$_4$)-Furyl-2 |
| 90 | 5-(2'-CH$_3$—C$_6$H$_4$)-Furyl-2 |
| 91 | 5-(4'-CH$_3$O—C$_6$H$_4$)-Furyl-2 |
| 92 | 5-(3'-CH$_3$O—C$_6$H$_4$)-Furyl-2 |
| 93 | 5-(2'-CH$_3$O—C$_6$H$_4$)-Furyl-2 |
| 94 | 5-(4'-NO$_2$—C$_6$H$_4$)-Furyl-2 |
| 95 | 5-(3'-NO$_2$—C$_6$H$_4$)-Furyl-2 |
| 96 | 5-(2'-NO$_2$—C$_6$H$_4$)-Furyl-2 |
| 97 | 5-(4'-CN—C$_6$H$_4$)-Furyl-2 |
| 98 | 5-(3'-CN—C$_6$H$_4$)-Furyl-2 |
| 99 | 5-(2'-CN—C$_6$H$_4$)-Furyl-2 |
| 100 | 5-(4'-CF$_3$—C$_6$H$_4$)-Furyl-2 |
| 101 | 5-(3'-CF$_3$—C$_6$H$_4$)-Furyl-2 |
| 102 | 5-(2'-CF$_3$—C$_6$H$_4$)-Furyl-2 |
| 103 | 5-(4'-t-C$_4$H$_9$—C$_6$H$_4$)-Furyl-2 |

TABLE 2-continued

R—CH=CH—[pyran ring with OCH$_3$ substituent]—C(=U)—CO$_2$CH$_3$

I: U: =CH—OCH$_3$
II: U: =N—OCH$_3$
III: U: =CH—CH$_3$

| No. | R |
|---|---|
| 104 | 5-(3'-t-C$_4$H$_9$—C$_6$H$_4$)-Furyl-2 |
| 105 | 5-(2'-t-C$_4$H$_9$—C$_6$H$_4$)-Furyl-2 |
| 106 | 5-(4'-C$_6$H$_5$—C$_6$H$_4$)-Furyl-2 |
| 107 | 5-(3'-C$_6$H$_5$—C$_6$H$_4$)-Furyl-2 |
| 108 | 5-(2'-C$_6$H$_5$—C$_6$H$_4$)-Furyl-2 |
| 109 | 5-(4'-Cl—C$_6$H$_4$)-Furyl-2 |
| 110 | 5-(3'-Cl—C$_6$H$_4$)-Furyl-2 |
| 111 | 5-(2'-Cl—C$_6$H$_4$)-Furyl-2 |
| 112 | 5-(4'-Br—C$_6$H$_4$)-Furyl-2 |
| 113 | 5-(3'-Br—C$_6$H$_4$)-Furyl-2 |
| 114 | 5-(2'-Br—C$_6$H$_4$)-Furyl-2 |
| 115 | 5-(4'-F—C$_6$H$_4$)-Furyl-2 |
| 116 | 5-(3'-F—C$_6$H$_4$)-Furyl-2 |
| 117 | 5-(2'-F—C$_6$H$_4$)-Furyl-2 |
| 118 | 5-(3',4'-Cl$_2$—C$_6$H$_3$)-Furyl-2 |
| 119 | 5-(2',4'-Cl$_2$—C$_6$H$_3$)-Furyl-2 |
| 120 | 5-(3',4'-F$_2$—C$_6$H$_3$)-Furyl-2 |
| 121 | 5-(2',4'-F$_2$—C$_6$H$_3$)-Furyl-2 |
| 122 | 5-(2',6'-F$_2$—C$_6$H$_3$)-Furyl-2 |
| 123 | 5-(5'-Cl-2'-CH$_3$O—C$_6$H$_3$)-Furyl-2 |
| 124 | 4-CH$_3$-Furyl-2 |
| 125 | 4-i-C$_3$H$_7$-Furyl-2 |
| 126 | 4-t-C$_4$H$_9$-Furyl-2 |
| 127 | 4-cyclo-C$_3$H$_5$-Furyl-2 |
| 128 | 4-C$_6$H$_5$-Furyl-2 |
| 129 | 4-(4'-CH$_3$—C$_6$H$_4$)-Furyl-2 |
| 130 | 4-(3'-CH$_3$—C$_6$H$_4$)-Furyl-2 |
| 131 | 4-(2'-CH$_3$—C$_6$H$_4$)-Furyl-2 |
| 132 | 4-(4'-CH$_3$O—C$_6$H$_4$)-Furyl-2 |
| 133 | 4-(3'-CH$_3$O—C$_6$H$_4$)-Furyl-2 |
| 134 | 4-(2'-CH$_3$O—C$_6$H$_4$)-Furyl-2 |
| 135 | 4-(4'-NO$_2$—C$_6$H$_4$)-Furyl-2 |
| 136 | 4-(3'-NO$_2$—C$_6$H$_4$)-Furyl-2 |
| 137 | 4-(2'-NO$_2$—C$_6$H$_4$)-Furyl-2 |
| 138 | 4-(4'-CN—C$_6$H$_4$)-Furyl-2 |
| 139 | 4-(3'-CN—C$_6$H$_4$)-Furyl-2 |
| 140 | 4-(2'-CN—C$_6$H$_4$)-Furyl-2 |
| 141 | 4-(4'-CF$_3$—C$_6$H$_4$)-Furyl-2 |
| 142 | 4-(3'-CF$_3$—C$_6$H$_4$)-Furyl-2 |
| 143 | 4-(2'-CF$_3$—C$_6$H$_4$)-Furyl-2 |
| 144 | 4-(4'-t-C$_4$H$_9$—C$_6$H$_4$)-Furyl-2 |
| 145 | 4-(3'-t-C$_4$H$_9$—C$_6$H$_4$)-Furyl-2 |
| 146 | 4-(2'-t-C$_4$H$_9$—C$_6$H$_4$)-Furyl-2 |
| 147 | 4-(4'-C$_6$H$_5$—C$_6$H$_4$)-Furyl-2 |
| 148 | 4-(3'-C$_6$H$_5$—C$_6$H$_4$)-Furyl-2 |
| 149 | 4-(2'-C$_6$H$_5$—C$_6$H$_4$)-Furyl-2 |
| 150 | 4-(4'-Cl—C$_6$H$_4$)-Furyl-2 |
| 151 | 4-(3'-Cl—C$_6$H$_4$)-Furyl-2 |
| 152 | 4-(2'-Cl—C$_6$H$_4$)-Furyl-2 |
| 153 | 4-(4'-Br—C$_6$H$_4$)-Furyl-2 |
| 154 | 4-(3'-Br—C$_6$H$_4$)-Furyl-2 |
| 155 | 4-(2'-Br—C$_6$H$_4$)-Furyl-2 |
| 156 | 4-(4'-F—C$_6$H$_4$)-Furyl-2 |
| 157 | 4-(3'-F—C$_6$H$_4$)-Furyl-2 |
| 158 | 4-(2'-F—C$_6$H$_4$)-Furyl-2 |
| 159 | 4-(3',4'-Cl$_2$—C$_6$H$_3$)-Furyl-2 |
| 160 | 4-(2',4'-Cl$_2$—C$_6$H$_3$)-Furyl-2 |
| 161 | 4-(3',4'-F$_2$—C$_6$H$_3$)-Furyl-2 |
| 162 | 4-(2',4'-F$_2$—C$_6$H$_3$)-Furyl-2 |
| 163 | 4-(2',6'-F$_2$—C$_6$H$_3$)-Furyl-2 |
| 164 | 4-(5'-Cl-2'-CH$_3$O—C$_6$H$_3$)-Furyl-2 |
| 165 | 5-CH$_3$-Thienyl-2 |
| 166 | 5-i-C$_3$H$_7$-Thienyl-2 |
| 167 | 5-t-C$_4$H$_9$-Thienyl-2 |
| 168 | 5-cyclo-C$_3$H$_5$-Thienyl-2 |
| 169 | 5-C$_6$H$_5$-Thienyl-2 |
| 170 | 5-(4'-CH$_3$—C$_6$H$_4$)-Thienyl-2 |
| 171 | 5-(3'-CH$_3$—C$_6$H$_4$)-Thienyl-2 |
| 172 | 5-(2'-CH$_3$—C$_6$H$_4$)-Thienyl-2 |
| 173 | 5-(4'-CH$_3$O—C$_6$H$_4$)-Thienyl-2 |
| 174 | 5-(3'-CH$_3$O—C$_6$H$_4$)-Thienyl-2 |
| 175 | 5-(2'-CH$_3$O—C$_6$H$_4$)-Thienyl-2 |
| 176 | 5-(4'-NO$_2$—C$_6$H$_4$)-Thienyl-2 |
| 177 | 5-(3'-NO$_2$—C$_6$H$_4$)-Thienyl-2 |
| 178 | 5-(2'-NO$_2$—C$_6$H$_4$)-Thienyl-2 |
| 179 | 5-(4'-CN—C$_6$H$_4$)-Thienyl-2 |
| 180 | 5-(3'-CN—C$_6$H$_4$)-Thienyl-2 |
| 181 | 5-(2'-CN—C$_6$H$_4$)-Thienyl-2 |
| 182 | 5-(4'-CF$_3$—C$_6$H$_4$)-Thienyl-2 |
| 183 | 5-(3'-CF$_3$—C$_6$H$_4$)-Thienyl-2 |
| 184 | 5-(2'-CF$_3$—C$_6$H$_4$)-Thienyl-2 |
| 185 | 5-(4'-t-C$_4$H$_9$—C$_6$H$_4$)-Thienyl-2 |
| 186 | 5-(3'-t-C$_4$H$_9$—C$_6$H$_4$)-Thienyl-2 |
| 187 | 5-(2'-t-C$_4$H$_9$—C$_6$H$_4$)-Thienyl-2 |
| 188 | 5-(4'-C$_6$H$_5$—C$_6$H$_4$)-Thienyl-2 |
| 189 | 5-(3'-C$_6$H$_5$—C$_6$H$_4$)-Thienyl-2 |
| 190 | 5-(2'-C$_6$H$_5$—C$_6$H$_4$)-Thienyl-2 |
| 191 | 5-(4'-Cl—C$_6$H$_4$)-Thienyl-2 |
| 192 | 5-(3'-Cl—C$_6$H$_4$)-Thienyl-2 |
| 193 | 5-(2'-Cl—C$_6$H$_4$)-Thienyl-2 |
| 194 | 5-(4'-Br—C$_6$H$_4$)-Thienyl-2 |
| 195 | 5-(3'-Br—C$_6$H$_4$)-Thienyl-2 |
| 196 | 5-(2'-Br—C$_6$H$_4$)-Thienyl-2 |
| 197 | 5-(4'-F—C$_6$H$_4$)-Thienyl-2 |
| 198 | 5-(3'-F—C$_6$H$_4$)-Thienyl-2 |
| 199 | 5-(2'-F—C$_6$H$_4$)-Thienyl-2 |
| 200 | 5-(3',4'-Cl$_2$—C$_6$H$_3$)-Thienyl-2 |
| 201 | 5-(2',4'-Cl$_2$—C$_6$H$_3$)-Thienyl-2 |
| 202 | 5-(3',4'-F$_2$—C$_6$H$_3$)-Thienyl-2 |
| 203 | 5-(2',4'-F$_2$—C$_6$H$_3$)-Thienyl-2 |
| 204 | 5-(2',6'-F$_2$—C$_6$H$_3$)-Thienyl-2 |
| 205 | 5-(5'-Cl-2'-CH$_3$O—C$_6$H$_3$)-Thienyl-2 |
| 206 | 4-CH$_3$-Thienyl-2 |
| 207 | 4-i-C$_3$H$_7$-Thienyl-2 |
| 208 | 4-t-C$_4$H$_9$-Thienyl-2 |
| 209 | 4-cyclo-C$_3$H$_5$-Thienyl-2 |
| 210 | 4-C$_6$H$_5$-Thienyl-2 |
| 211 | 4-(4'-CH$_3$—C$_6$H$_4$)-Thienyl-2 |
| 212 | 4-(3'-CH$_3$—C$_6$H$_4$)-Thienyl-2 |
| 213 | 4-(2'-CH$_3$—C$_6$H$_4$)-Thienyl-2 |
| 214 | 4-(4'-CH$_3$O—C$_6$H$_4$)-Thienyl-2 |
| 215 | 4-(3'-CH$_3$O—C$_6$H$_4$)-Thienyl-2 |
| 216 | 4-(2'-CH$_3$O—C$_6$H$_4$)-Thienyl-2 |
| 217 | 4-(4'-NO$_2$—C$_6$H$_4$)-Thienyl-2 |
| 218 | 4-(3'-NO$_2$—C$_6$H$_4$)-Thienyl-2 |
| 219 | 4-(2'-NO$_2$—C$_6$H$_4$)-Thienyl-2 |
| 220 | 4-(4'-CN—C$_6$H$_4$)-Thienyl-2 |
| 221 | 4-(3'-CN—C$_6$H$_4$)-Thienyl-2 |
| 222 | 4-(2'-CN—C$_6$H$_4$)-Thienyl-2 |
| 223 | 4-(4'-CF$_3$—C$_6$H$_4$)-Thienyl-2 |
| 224 | 4-(3'-CF$_3$—C$_6$H$_4$)-Thienyl-2 |
| 225 | 4-(2'-CF$_3$—C$_6$H$_4$)-Thienyl-2 |
| 226 | 4-(4'-t-C$_4$H$_9$—C$_6$H$_4$)-Thienyl-2 |
| 227 | 4-(3'-t-C$_4$H$_9$—C$_6$H$_4$)-Thienyl-2 |
| 228 | 4-(2'-t-C$_4$H$_9$—C$_6$H$_4$)-Thienyl-2 |
| 229 | 4-(4'-C$_6$H$_5$—C$_6$H$_4$)-Thienyl-2 |
| 230 | 4-(3'-C$_6$H$_5$—C$_6$H$_4$)-Thienyl-2 |
| 231 | 4-(2'-C$_6$H$_5$—C$_6$H$_4$)-Thienyl-2 |
| 232 | 4-(4'-Cl—C$_6$H$_4$)-Thienyl-2 |
| 233 | 4-(3'-Cl—C$_6$H$_4$)-Thienyl-2 |
| 234 | 4-(2'-Cl—C$_6$H$_4$)-Thienyl-2 |
| 235 | 4-(4'-Br—C$_6$H$_4$)-Thienyl-2 |
| 236 | 4-(3'-Br—C$_6$H$_4$)-Thienyl-2 |
| 237 | 4-(2'-Br—C$_6$H$_4$)-Thienyl-2 |
| 238 | 4-(4'-F—C$_6$H$_4$)-Thienyl-2 |
| 239 | 4-(3'-F—C$_6$H$_4$)-Thienyl-2 |
| 240 | 4-(2'-F—C$_6$H$_4$)-Thienyl-2 |
| 241 | 4-(3',4'-Cl$_2$—C$_6$H$_3$)-Thienyl-2 |

TABLE 2-continued $$\text{R}\diagdown\text{(structure with O, H}_3\text{CO}_2\text{C, U)}$$

I: U: =CH—OCH$_3$
II: U: =N—OCH$_3$
III: U: =CH—CH$_3$

| No. | R |
|---|---|
| 242 | 4-(2',4'-Cl$_2$—C$_6$H$_3$)-Thienyl-2 |
| 243 | 4-(3',4'-F$_2$—C$_6$H$_3$)-Thienyl-2 |
| 244 | 4-(2',4'-F$_2$—C$_6$H$_3$)-Thienyl-2 |
| 245 | 4-(2',6'-F$_2$—C$_6$H$_3$)-Thienyl-2 |
| 246 | 4-(5'-Cl-2'-CH$_3$O—C$_6$H$_3$)-Thienyl-2 |
| 247 | 5-CH$_3$-Thienyl-3 |
| 248 | 5-i-C$_3$H$_7$-Thienyl-3 |
| 249 | 5-t-C$_4$H$_9$-Thienyl-3 |
| 250 | 5-cyclo-C$_3$H$_5$-Thienyl-3 |
| 251 | 5-C$_6$H$_5$-Thienyl-3 |
| 252 | 5-(4'-CH$_3$—C$_6$H$_4$)-Thienyl-3 |
| 253 | 5-(3'-CH$_3$—C$_6$H$_4$)-Thienyl-3 |
| 254 | 5-(2'-CH$_3$—C$_6$H$_4$)-Thienyl-3 |
| 255 | 5-(4'-CH$_3$O—C$_6$H$_4$)-Thienyl-3 |
| 256 | 5-(3'-CH$_3$O—C$_6$H$_4$)-Thienyl-3 |
| 257 | 5-(2'-CH$_3$O—C$_6$H$_4$)-Thienyl-3 |
| 258 | 5-(4'-NO$_2$—C$_6$H$_4$)-Thienyl-3 |
| 259 | 5-(3'-NO$_2$—C$_6$H$_4$)-Thienyl-3 |
| 260 | 5-(2'-NO$_2$—C$_6$H$_4$)-Thienyl-3 |
| 261 | 5-(4'-CN—C$_6$H$_4$)-Thienyl-3 |
| 262 | 5-(3'-CN—C$_6$H$_4$)-Thienyl-3 |
| 263 | 5-(2'-CN—C$_6$H$_4$)-Thienyl-3 |
| 264 | 5-(4'-CF$_3$—C$_6$H$_4$)-Thienyl-3 |
| 265 | 5-(3'-CF$_3$—C$_6$H$_4$)-Thienyl-3 |
| 266 | 5-(2'-CF$_3$—C$_6$H$_4$)-Thienyl-3 |
| 267 | 5-(4'-t-C$_4$H$_9$—C$_6$H$_4$)-Thienyl-3 |
| 268 | 5-(3'-t-C$_4$H$_9$—C$_6$H$_4$)-Thienyl-3 |
| 269 | 5-(2'-t-C$_4$H$_9$—C$_6$H$_4$)-Thienyl-3 |
| 270 | 5-(4'-C$_6$H$_5$—C$_6$H$_4$)-Thienyl-3 |
| 271 | 5-(3'-C$_6$H$_5$—C$_6$H$_4$)-Thienyl-3 |
| 272 | 5-(2'-C$_6$H$_5$—C$_6$H$_4$)-Thienyl-3 |
| 273 | 5-(4'-Cl—C$_6$H$_4$)-Thienyl-3 |
| 274 | 5-(3'-Cl—C$_6$H$_4$)-Thienyl-3 |
| 275 | 5-(2'-Cl—C$_6$H$_4$)-Thienyl-3 |
| 276 | 5-(4'-Br—C$_6$H$_4$)-Thienyl-3 |
| 277 | 5-(3'-Br—C$_6$H$_4$)-Thienyl-3 |
| 278 | 5-(2'-Br—C$_6$H$_4$)-Thienyl-3 |
| 279 | 5-(4'-F—C$_6$H$_4$)-Thienyl-3 |
| 280 | 5-(3'-F—C$_6$H$_4$)-Thienyl-3 |
| 281 | 5-(2'-F—C$_6$H$_4$)-Thienyl-3 |
| 282 | 5-(3',4'-Cl$_2$—C$_6$H$_3$)-Thienyl-3 |
| 283 | 5-(2',4'-Cl$_2$—C$_6$H$_3$)-Thienyl-3 |
| 284 | 5-(3',4'-F$_2$—C$_6$H$_3$)-Thienyl-3 |
| 285 | 5-(2',4'-F$_2$—C$_6$H$_3$)-Thienyl-3 |
| 286 | 5-(2',6'-F$_2$—C$_6$H$_3$)-Thienyl-3 |
| 287 | 5-(5'-Cl-2'-CH$_3$O—C$_6$H$_3$)-Thienyl-3 |
| 288 | N—CH$_3$-Pyrazolyl-4 |
| 289 | N-i-C$_3$H$_7$-Pyrazolyl-4 |
| 290 | N-t-C$_4$H$_9$-Pyrazolyl-4 |
| 291 | N-cyclo-C$_3$H$_5$-Pyrazolyl-4 |
| 292 | N—C$_6$H$_5$-Pyrazolyl-4 |
| 293 | N-(4'-CH$_3$—C$_6$H$_4$)-Pyrazolyl-4 |
| 294 | N-(3'-CH$_3$—C$_6$H$_4$)-Pyrazolyl-4 |
| 295 | N-(2'-CH$_3$—C$_6$H$_4$)-Pyrazolyl-4 |
| 296 | N-(4'-CH$_3$O—C$_6$H$_4$)-Pyrazolyl-4 |
| 297 | N-(3'-CH$_3$O—C$_6$H$_4$)-Pyrazolyl-4 |
| 298 | N-(2'-CH$_3$O—C$_6$H$_4$)-Pyrazolyl-4 |
| 299 | N-(4'-NO$_2$—C$_6$H$_4$)-Pyrazolyl-4 |
| 300 | N-(3'-NO$_2$—C$_6$H$_4$)-Pyrazolyl-4 |
| 301 | N-(2'-NO$_2$—C$_6$H$_4$)-Pyrazolyl-4 |
| 302 | N-(4'-CN—C$_6$H$_4$)-Pyrazolyl-4 |
| 303 | N-(3'-CN—C$_6$H$_4$)-Pyrazolyl-4 |
| 304 | N-(2'-CN—C$_6$H$_4$)-Pyrazolyl-4 |
| 305 | N-(4'-CF$_3$—C$_6$H$_4$)-Pyrazolyl-4 |
| 306 | N-(3'-CF$_3$—C$_6$H$_4$)-Pyrazolyl-4 |
| 307 | N-(2'-CF$_3$—C$_6$H$_4$)-Pyrazolyl-4 |
| 308 | N-(4'-t-C$_4$H$_9$—C$_6$H$_4$)-Pyrazolyl-4 |
| 309 | N-(3'-t-C$_4$H$_9$—C$_6$H$_4$)-Pyrazolyl-4 |
| 310 | N-(2'-t-C$_4$H$_9$—C$_6$H$_4$)-Pyrazolyl-4 |
| 311 | N-(4'-C$_6$H$_5$—C$_6$H$_4$)-Pyrazolyl-4 |
| 312 | N-(3'-C$_6$H$_5$—C$_6$H$_4$)-Pyrazolyl-4 |
| 313 | N-(2'-C$_6$H$_5$—C$_6$H$_4$)-Pyrazolyl-4 |
| 314 | N-(4'-Cl—C$_6$H$_4$)-Pyrazolyl-4 |
| 315 | N-(3'-Cl—C$_6$H$_4$)-Pyrazolyl-4 |
| 316 | N-(2'-Cl—C$_6$H$_4$)-Pyrazolyl-4 |
| 317 | N-(4'-Br—C$_6$H$_4$)-Pyrazolyl-4 |
| 318 | N-(3'-Br—C$_6$H$_4$)-Pyrazolyl-4 |
| 319 | N-(2'-Br—C$_6$H$_4$)-Pyrazolyl-4 |
| 320 | N-(4'-F—C$_6$H$_4$)-Pyrazolyl-4 |
| 321 | N-(3'-F—C$_6$H$_4$)-Pyrazolyl-4 |
| 322 | N-(2'-F—C$_6$H$_4$)-Pyrazolyl-4 |
| 323 | N-(3',4'-Cl$_2$—C$_6$H$_3$)-Pyrazolyl-4 |
| 324 | N-(2',4'-Cl$_2$—C$_6$H$_3$)-Pyrazolyl-4 |
| 325 | N-(3',4'-F$_2$—C$_6$H$_3$)-Pyrazolyl-4 |
| 326 | N-(2',4'-F$_2$—C$_6$H$_3$)-Pyrazolyl-4 |
| 327 | N-(2',6'-F$_2$—C$_6$H$_3$)-Pyrazolyl-4 |
| 328 | N-(5'-Cl-2'-CH$_3$O—C$_6$H$_3$)-Pyrazolyl-4 |
| 329 | 3-CH$_3$—N-Methylpyrazolyl-4 |
| 330 | 3-i-C$_3$H$_7$—N-Methylpyrazolyl-4 |
| 331 | 3-t-C$_4$H$_9$—N-Methylpyrazolyl-4 |
| 332 | 3-cyclo-C$_3$H$_9$—N-Methylpyrazolyl-4 |
| 333 | 3-C$_6$H$_5$—N-Methylpyrazolyl-4 |
| 334 | 3-(4'-CH$_3$—C$_6$H$_4$)-N-Methylpyrazolyl-4 |
| 335 | 3-(3'-CH$_3$—C$_6$H$_4$)-N-Methylpyrazolyl-4 |
| 336 | 3-(2'-CH$_3$—C$_6$H$_4$)-N-Methylpyrazolyl-4 |
| 337 | 3-(4'-CH$_3$O—C$_6$H$_4$)-N-Methylpyrazolyl-4 |
| 338 | 3-(3'-CH$_3$O—C$_6$H$_4$)-N-Methylpyrazolyl-4 |
| 339 | 3-(2'-CH$_3$O—C$_6$H$_4$)-N-Methylpyrazolyl-4 |
| 340 | 3-(4'-NO$_2$—C$_6$H$_4$)-N-Methylpyrazolyl-4 |
| 341 | 3-(3'-NO$_2$—C$_6$H$_4$)-N-Methylpyrazolyl-4 |
| 342 | 3-(2'-NO$_2$—C$_6$H$_4$)-N-Methylpyrazolyl-4 |
| 343 | 3-(4'-CN—C$_6$H$_4$)-N-Methylpyrazolyl-4 |
| 344 | 3-(3'-CN—C$_6$H$_4$)-N-Methylpyrazolyl-4 |
| 345 | 3-(2'-CN—C$_6$H$_4$)-N-Methylpyrazolyl-4 |
| 346 | 3-(4'-CF$_3$—C$_6$H$_4$)-N-Methylpyrazolyl-4 |
| 347 | 3-(3'-CF$_3$—C$_6$H$_4$)-N-Methylpyrazolyl-4 |
| 348 | 3-(2'-CF$_3$—C$_6$H$_4$)-N-Methylpyrazolyl-4 |
| 349 | 3-(4'-t-C$_4$H$_9$—C$_6$H$_4$)-N-Methylpyrazolyl-4 |
| 350 | 3-(3'-t-C$_4$H$_9$—C$_6$H$_4$)-N-Methylpyrazolyl-4 |
| 351 | 3-(2'-t-C$_4$H$_9$—C$_6$H$_4$)-N-Methylpyrazolyl-4 |
| 352 | 3-(4'-C$_6$H$_5$—C$_6$H$_4$)-N-Methylpyrazolyl-4 |
| 353 | 3-(3'-C$_6$H$_5$—C$_6$H$_4$)-N-Methylpyrazolyl-4 |
| 354 | 3-(2'-C$_6$H$_5$—C$_6$H$_4$)-N-Methylpyrazolyl-4 |
| 355 | 3-(4'-Cl—C$_6$H$_4$)-N-Methylpyrazolyl-4 |
| 356 | 3-(3'-Cl—C$_6$H$_4$)-N-Methylpyrazolyl-4 |
| 357 | 3-(2'-Cl—C$_6$H$_4$)-N-Methylpyrazolyl-4 |
| 358 | 3-(4'-Br—C$_6$H$_4$)-N-Methylpyrazolyl-4 |
| 359 | 3-(3'-Br—C$_6$H$_4$)-N-Methylpyrazolyl-4 |
| 360 | 3-(2'-Br—C$_6$H$_4$)-N-Methylpyrazolyl-4 |
| 361 | 3-(4'-F—C$_6$H$_4$)-N-Methylpyrazolyl-4 |
| 362 | 3-(3'-F—C$_6$H$_4$)-N-Methylpyrazolyl-4 |
| 363 | 3-(2'-F—C$_6$H$_4$)-N-Methylpyrazolyl-4 |
| 364 | 3-(3',4'-Cl$_2$—C$_6$H$_3$)-N-Methylpyrazolyl-4 |
| 365 | 3-(2',4'-Cl$_2$—C$_6$H$_3$)-N-Methylpyrazolyl-4 |
| 366 | 3-(3',4'-F$_2$—C$_6$H$_3$)-N-Methylpyrazolyl-4 |
| 367 | 3-(2',4'-F$_2$—C$_6$H$_3$)-N-Methylpyrazolyl-4 |
| 368 | 3-(2',6'-F$_2$—C$_6$H$_3$)-N-Methylpyrazolyl-4 |
| 369 | 3-(5'-Cl-2'-CH$_3$O—C$_6$H$_3$)-N-Methylpyrazolyl-4 |
| 370 | 3-CH$_3$-Isoxazolyl-5 |
| 371 | 3-i-C$_3$H$_7$-Isoxazolyl-5 |
| 372 | 3-t-C$_4$H$_9$-Isoxazolyl-5 |
| 373 | 3-cyclo-C$_3$H$_9$-Isoxazolyl-5 |
| 374 | 3-C$_6$H$_5$-Isoxazolyl-5 |
| 375 | 3-(4'-CH$_3$—C$_6$H$_4$)-Isoxazolyl-5 |
| 376 | 3-(3'-CH$_3$—C$_6$H$_4$)-Isoxazolyl-5 |
| 377 | 3-(2'-CH$_3$—C$_6$H$_4$)-Isoxazolyl-5 |
| 378 | 3-(4'-CH$_3$O—C$_6$H$_4$)-Isoxazolyl-5 |
| 379 | 3-(3'-CH$_3$O—C$_6$H$_4$)-Isoxazolyl-5 |

TABLE 2-continued $$\text{R}-\text{CH}=\text{C}(\text{O})-\text{C}(\text{CO}_2\text{CH}_3)=\text{U}$$ (ring with O)

I: U: =CH—OCH$_3$
II: U: =N—OCH$_3$
III: U: =CH—CH$_3$

| No. | R |
|---|---|
| 380 | 3-(2'-CH$_3$O—C$_6$H$_4$)-Isoxazolyl-5 |
| 381 | 3-(4'-NO$_2$—C$_6$H$_4$)-Isoxazolyl-5 |
| 382 | 3-(3'-NO$_2$—C$_6$H$_4$)-Isoxazolyl-5 |
| 383 | 3-(2'-NO$_2$—C$_6$H$_4$)-Isoxazolyl-5 |
| 384 | 3-(4'-CN—C$_6$H$_4$)-Isoxazolyl-5 |
| 385 | 3-(3'-CN—C$_6$H$_4$)-Isoxazolyl-5 |
| 386 | 3-(2'-CN—C$_6$H$_4$)-Isoxazolyl-5 |
| 387 | 3-(4'-CF$_3$—C$_6$H$_4$)-Isoxazolyl-5 |
| 388 | 3-(3'-CF$_3$—C$_6$H$_4$)-Isoxazolyl-5 |
| 389 | 3-(2'-CF$_3$—C$_6$H$_4$)-Isoxazolyl-5 |
| 390 | 3-(4'-t-C$_4$H$_9$—C$_6$H$_4$)-Isoxazolyl-5 |
| 391 | 3-(3'-t-C$_4$H$_9$—C$_6$H$_4$)-Isoxazolyl-5 |
| 392 | 3-(2'-t-C$_4$H$_9$—C$_6$H$_4$)-Isoxazolyl-5 |
| 393 | 3-(4'-C$_6$H$_5$—C$_6$H$_4$)-Isoxazolyl-5 |
| 394 | 3-(3'-C$_6$H$_5$—C$_6$H$_4$)-Isoxazolyl-5 |
| 395 | 3-(2'-C$_6$H$_5$—C$_6$H$_4$)-Isoxazolyl-5 |
| 396 | 3-(4'-Cl—C$_6$H$_4$)-Isoxazolyl-5 |
| 397 | 3-(3'-Cl—C$_6$H$_4$)-Isoxazolyl-5 |
| 398 | 3-(2'-Cl—C$_6$H$_4$)-Isoxazolyl-5 |
| 399 | 3-(4'-Br—C$_6$H$_4$)-Isoxazolyl-5 |
| 400 | 3-(3'-Br—C$_6$H$_4$)-Isoxazolyl-5 |
| 401 | 3-(2'-Br—C$_6$H$_4$)-Isoxazolyl-5 |
| 402 | 3-(4'-F—C$_6$H$_4$)-Isoxazolyl-5 |
| 403 | 3-(3'-F—C$_6$H$_4$)-Isoxazolyl-5 |
| 404 | 3-(2'-F—C$_6$H$_4$)-Isoxazolyl-5 |
| 405 | 3-(3',4'-Cl$_2$—C$_6$H$_3$)-Isoxazolyl-5 |
| 406 | 3-(2',4'-Cl$_2$—C$_6$H$_3$)-Isoxazolyl-5 |
| 407 | 3-(3',4'-F$_2$—C$_6$H$_3$)-Isoxazolyl-5 |
| 408 | 3-(2',4'-F$_2$—C$_6$H$_3$)-Isoxazolyl-5 |
| 409 | 3-(2',6'-F$_2$—C$_6$H$_3$)-Isoxazolyl-5 |
| 410 | 3-(5'-Cl-2'-CH$_3$O—C$_6$H$_3$)-Isoxazolyl-5 |
| 411 | 3-CH$_3$-chloroisoxazolyl-5 |
| 412 | 3-i-C$_3$H$_7$-chloroisoxazolyl-5 |
| 413 | 3-t-C$_4$H$_9$-chloroisoxazolyl-5 |
| 414 | 3-cyclo-C$_3$H$_9$-chloroisoxazolyl-5 |
| 415 | 3-C$_6$H$_5$-chloroisoxazolyl-5 |
| 416 | 3-(4'-CH$_3$—C$_6$H$_4$)-chloroisoxazolyl-5 |
| 417 | 3-(3'-CH$_3$—C$_6$H$_4$)-chloroisoxazolyl-5 |
| 418 | 3-(2'-CH$_3$—C$_6$H$_4$)-chloroisoxazolyl-5 |
| 419 | 3-(4'-CH$_3$O—C$_6$H$_4$)-chloroisoxazolyl-5 |
| 420 | 3-(3'-CH$_3$O—C$_6$H$_4$)-chloroisoxazolyl-5 |
| 421 | 3-(2'-CH$_3$O—C$_6$H$_4$)-chloroisoxazolyl-5 |
| 422 | 3-(4'-NO$_2$—C$_6$H$_4$)-chloroisoxazolyl-5 |
| 423 | 3-(3'-NO$_2$—C$_6$H$_4$)-chloroisoxazolyl-5 |
| 424 | 3-(2'-NO$_2$—C$_6$H$_4$)-chloroisoxazolyl-5 |
| 425 | 3-(4'-CN—C$_6$H$_4$)-chloroisoxazolyl-5 |
| 426 | 3-(3'-CN—C$_6$H$_4$)-chloroisoxazolyl-5 |
| 427 | 3-(2'-CN—C$_6$H$_4$)-chloroisoxazolyl-5 |
| 428 | 3-(4'-CF$_3$—C$_6$H$_4$)-chloroisoxazolyl-5 |
| 429 | 3-(3'-CF$_3$—C$_6$H$_4$)-chloroisoxazolyl-5 |
| 430 | 3-(2'-CF$_3$—C$_6$H$_4$)-chloroisoxazolyl-5 |
| 431 | 3-(4'-t-C$_4$H$_9$—C$_6$H$_4$)-chloroisoxazolyl-5 |
| 432 | 3-(3'-t-C$_4$H$_9$—C$_6$H$_4$)-chloroisoxazolyl-5 |
| 433 | 3-(2'-t-C$_4$H$_9$—C$_6$H$_4$)-chloroisoxazolyl-5 |
| 434 | 3-(4'-C$_6$H$_5$—C$_6$H$_4$)-chloroisoxazolyl-5 |
| 435 | 3-(3'-C$_6$H$_5$—C$_6$H$_4$)-chloroisoxazolyl-5 |
| 436 | 3-(2'-C$_6$H$_5$—C$_6$H$_4$)-chloroisoxazolyl-5 |
| 437 | 3-(4'-Cl—C$_6$H$_4$)-chloroisoxazolyl-5 |
| 438 | 3-(3'-Cl—C$_6$H$_4$)-chloroisoxazolyl-5 |
| 439 | 3-(2'-Cl—C$_6$H$_4$)-chloroisoxazolyl-5 |
| 440 | 3-(4'-Br—C$_6$H$_4$)-chloroisoxazolyl-5 |
| 441 | 3-(3'-Br—C$_6$H$_4$)-chloroisoxazolyl-5 |
| 442 | 3-(2'-Br—C$_6$H$_4$)-chloroisoxazolyl-5 |
| 443 | 3-(4'-F—C$_6$H$_4$)-chloroisoxazolyl-5 |
| 444 | 3-(3'-F—C$_6$H$_4$)-chloroisoxazolyl-5 |
| 445 | 3-(2'-F—C$_6$H$_4$)-chloroisoxazolyl-5 |
| 446 | 3-(3',4'-Cl$_2$—C$_6$H$_3$)-chloroisoxazolyl-5 |
| 447 | 3-(2',4'-Cl$_2$—C$_6$H$_3$)-chloroisoxazolyl-5 |
| 448 | 3-(3',4'-F$_2$—C$_6$H$_3$)-chloroisoxazolyl-5 |
| 449 | 3-(2',4'-F$_2$—C$_6$H$_3$)-chloroisoxazolyl-5 |
| 450 | 3-(2',6'-F$_2$—C$_6$H$_3$)-chloroisoxazolyl-5 |
| 451 | 3-(5'-Cl-2'-CH$_3$O—C$_6$H$_3$)-chloroisoxazolyl-5 |
| 452 | 5-CH$_3$-Isoxazolyl-3 |
| 453 | 5-i-C$_3$H$_7$-Isoxazolyl-3 |
| 454 | 5-t-C$_4$H$_9$-Isoxazolyl-3 |
| 455 | 5-cyclo-C$_3$H$_5$-Isoxazolyl-3 |
| 456 | 5-C$_6$H$_5$-Isoxazolyl-3 |
| 457 | 5-(4'-CH$_3$—C$_6$H$_4$)-Isoxazolyl-3 |
| 458 | 5-(3'-CH$_3$—C$_6$H$_4$)-Isoxazolyl-3 |
| 459 | 5-(2'-CH$_3$—C$_6$H$_4$)-Isoxazolyl-3 |
| 460 | 5-(4'-CH$_3$O—C$_6$H$_4$)-Isoxazolyl-3 |
| 461 | 5-(3'-CH$_3$O—C$_6$H$_4$)-Isoxazolyl-3 |
| 462 | 5-(2'-CH$_3$O—C$_6$H$_4$)-Isoxazolyl-3 |
| 463 | 5-(4'-NO$_2$—C$_6$H$_4$)-Isoxazolyl-3 |
| 464 | 5-(3'-NO$_2$—C$_6$H$_4$)-Isoxazolyl-3 |
| 465 | 5-(2'-NO$_2$—C$_6$H$_4$)-Isoxazolyl-3 |
| 466 | 5-(4'-CN—C$_6$H$_4$)-Isoxazolyl-3 |
| 467 | 5-(3'-CN—C$_6$H$_4$)-Isoxazolyl-3 |
| 468 | 5-(2'-CN—C$_6$H$_4$)-Isoxazolyl-3 |
| 469 | 5-(4'-CF$_3$—C$_6$H$_4$)-Isoxazolyl-3 |
| 470 | 5-(3'-CF$_3$—C$_6$H$_4$)-Isoxazolyl-3 |
| 471 | 5-(2'-CF$_3$—C$_6$H$_4$)-Isoxazolyl-3 |
| 472 | 5-(4'-t-C$_4$H$_9$—C$_6$H$_4$)-Isoxazolyl-3 |
| 473 | 5-(3'-t-C$_4$H$_9$—C$_6$H$_4$)-Isoxazolyl-3 |
| 474 | 5-(2'-t-C$_4$H$_9$—C$_6$H$_4$)-Isoxazolyl-3 |
| 475 | 5-(4'-C$_6$H$_5$—C$_6$H$_4$)-Isoxazolyl-3 |
| 476 | 5-(3'-C$_6$H$_5$—C$_6$H$_4$)-Isoxazolyl-3 |
| 477 | 5-(2'-C$_6$H$_5$—C$_6$H$_4$)-Isoxazolyl-3 |
| 478 | 5-(4'-Cl—C$_6$H$_4$)-Isoxazolyl-3 |
| 479 | 5-(3'-Cl—C$_6$H$_4$)-Isoxazolyl-3 |
| 480 | 5-(2'-Cl—C$_6$H$_4$)-Isoxazolyl-3 |
| 481 | 5-(4'-Br—C$_6$H$_4$)-Isoxazolyl-3 |
| 482 | 5-(3'-Br—C$_6$H$_4$)-Isoxazolyl-3 |
| 483 | 5-(2'-Br—C$_6$H$_4$)-Isoxazolyl-3 |
| 484 | 5-(4'-F—C$_6$H$_4$)-Isoxazolyl-3 |
| 485 | 5-(3'-F—C$_6$H$_4$)-Isoxazolyl-3 |
| 486 | 5-(2'-F—C$_6$H$_4$)-Isoxazolyl-3 |
| 487 | 5-(3',4'-Cl$_2$—C$_6$H$_3$)-Isoxazolyl-3 |
| 488 | 5-(2',4'-Cl$_2$—C$_6$H$_3$)-Isoxazolyl-3 |
| 489 | 5-(3',4'-F$_2$—C$_6$H$_3$)-Isoxazolyl-3 |
| 490 | 5-(2',4'-F$_2$—C$_6$H$_3$)-Isoxazolyl-3 |
| 491 | 5-(2',6'-F$_2$—C$_6$H$_3$)-Isoxazolyl-3 |
| 492 | 5-(5'-Cl-2'-CH$_3$O—C$_6$H$_3$)-Isoxazolyl-3 |
| 493 | 3-CH$_3$-Isothiazolyl-5 |
| 494 | 3-i-C$_3$H$_7$-Isothiazolyl-5 |
| 495 | 3-t-C$_4$H$_9$-Isothiazolyl-5 |
| 496 | 3-cyclo-C$_3$H$_9$-Isothiazolyl-5 |
| 497 | 3-C$_6$H$_5$-Isothiazolyl-5 |
| 498 | 3-(4'-CH$_3$—C$_6$H$_4$)-Isothiazolyl-5 |
| 499 | 3-(3'-CH$_3$—C$_6$H$_4$)-Isothiazolyl-5 |
| 500 | 3-(2'-CH$_3$—C$_6$H$_4$)-Isothiazolyl-5 |
| 501 | 3-(4'-CH$_3$O—C$_6$H$_4$)-Isothiazolyl-5 |
| 502 | 3-(3'-CH$_3$O—C$_6$H$_4$)-Isothiazolyl-5 |
| 503 | 3-(2'-CH$_3$O—C$_6$H$_4$)-Isothiazolyl-5 |
| 504 | 3-(4'-NO$_2$—C$_6$H$_4$)-Isothiazolyl-5 |
| 505 | 3-(3'-NO$_2$—C$_6$H$_4$)-Isothiazolyl-5 |
| 506 | 3-(2'-NO$_2$—C$_6$H$_4$)-Isothiazolyl-5 |
| 507 | 3-(4'-CN—C$_6$H$_4$)-Isothiazolyl-5 |
| 508 | 3-(3'-CN—C$_6$H$_4$)-Isothiazolyl-5 |
| 509 | 3-(2'-CN—C$_6$H$_4$)-Isothiazolyl-5 |
| 510 | 3-(4'-CF$_3$—C$_6$H$_4$)-Isothiazolyl-5 |
| 511 | 3-(3'-CF$_3$—C$_6$H$_4$)-Isothiazolyl-5 |
| 512 | 3-(2'-CF$_3$—C$_6$H$_4$)-Isothiazolyl-5 |
| 513 | 3-(4'-t-C$_4$H$_9$—C$_6$H$_4$)-Isothiazolyl-5 |
| 514 | 3-(3'-t-C$_4$H$_9$—C$_6$H$_4$)-Isothiazolyl-5 |
| 515 | 3-(2'-t-C$_4$H$_9$—C$_6$H$_4$)-Isothiazolyl-5 |
| 516 | 3-(4'-C$_6$H$_5$—C$_6$H$_4$)-Isothiazolyl-5 |
| 517 | 3-(3'-C$_6$H$_5$—C$_6$H$_4$)-Isothiazolyl-5 |

TABLE 2-continued $$\text{R} - \text{CH=C(CO}_2\text{CH}_3)\text{-U with dihydropyran ring}$$

I: U: =CH—OCH$_3$
II: U: =N—OCH$_3$
III: U: =CH—CH$_3$

| No. | R |
|---|---|
| 518 | 3-(2'-C$_6$H$_5$—C$_6$H$_4$)-Isothiazolyl-5 |
| 519 | 3-(4'-Cl—C$_6$H$_4$)-Isothiazolyl-5 |
| 520 | 3-(3'-Cl—C$_6$H$_4$)-Isothiazolyl-5 |
| 521 | 3-(2'-Cl—C$_6$H$_4$)-Isothiazolyl-5 |
| 522 | 3-(4'-Br—C$_6$H$_4$)-Isothiazolyl-5 |
| 523 | 3-(3'-Br—C$_6$H$_4$)-Isothiazolyl-5 |
| 524 | 3-(2'-Br—C$_6$H$_4$)-Isothiazolyl-5 |
| 525 | 3-(4'-F—C$_6$H$_4$)-Isothiazolyl-5 |
| 526 | 3-(3'-F—C$_6$H$_4$)-Isothiazolyl-5 |
| 527 | 3-(2'-F—C$_6$H$_4$)-Isothiazolyl-5 |
| 528 | 3-(3',4'-Cl$_2$—C$_6$H$_3$)-Isothiazolyl-5 |
| 529 | 3-(2',4'-Cl$_2$—C$_6$H$_3$)-Isothiazolyl-5 |
| 530 | 3-(3',4'-F$_2$—C$_6$H$_3$)-Isothiazolyl-5 |
| 531 | 3-(2',4'-F$_2$—C$_6$H$_3$)-Isothiazolyl-5 |
| 532 | 3-(2',6'-F$_2$—C$_6$H$_3$)-Isothiazolyl-5 |
| 533 | 3-(5'-Cl-2'-CH$_3$O—C$_6$H$_3$)-Isothiazolyl-5 |
| 534 | 2-CH$_3$-Oxazolyl-4 |
| 535 | 2-i-C$_3$H$_7$-Oxazolyl-4 |
| 536 | 2-t-C$_4$H$_9$-Oxazolyl-4 |
| 537 | 2-cyclo-C$_3$H$_9$-Oxazolyl-4 |
| 538 | 2-C$_6$H$_5$-Oxazolyl-4 |
| 539 | 2-(4'-CH$_3$—C$_6$H$_4$)-Oxazolyl-4 |
| 540 | 2-(3'-CH$_3$—C$_6$H$_4$)-Oxazolyl-4 |
| 541 | 2-(2'-CH$_3$—C$_6$H$_4$)-Oxazolyl-4 |
| 542 | 2-(4'-CH$_3$O—C$_6$H$_4$)-Oxazolyl-4 |
| 543 | 2-(3'-CH$_3$O—C$_6$H$_4$)-Oxazolyl-4 |
| 544 | 2-(2'-CH$_3$O—C$_6$H$_4$)-Oxazolyl-4 |
| 545 | 2-(4'-NO$_2$—C$_6$H$_4$)-Oxazolyl-4 |
| 546 | 2-(3'-NO$_2$—C$_6$H$_4$)-Oxazolyl-4 |
| 547 | 2-(2'-NO$_2$—C$_6$H$_4$)-Oxazolyl-4 |
| 548 | 2-(4'-CN—C$_6$H$_4$)-Oxazolyl-4 |
| 549 | 2-(3'-CN—C$_6$H$_4$)-Oxazolyl-4 |
| 550 | 2-(2'-CN—C$_6$H$_4$)-Oxazolyl-4 |
| 551 | 2-(4'-CF$_3$—C$_6$H$_4$)-Oxazolyl-4 |
| 552 | 2-(3'-CF$_3$—C$_6$H$_4$)-Oxazolyl-4 |
| 553 | 2-(2'-CF$_3$—C$_6$H$_4$)-Oxazolyl-4 |
| 554 | 2-(4'-t-C$_4$H$_9$—C$_6$H$_4$)-Oxazolyl-4 |
| 555 | 2-(3'-t-C$_4$H$_9$—C$_6$H$_4$)-Oxazolyl-4 |
| 556 | 2-(2'-t-C$_4$H$_9$—C$_6$H$_4$)-Oxazolyl-4 |
| 557 | 2-(4'-C$_6$H$_5$—C$_6$H$_4$)-Oxazolyl-4 |
| 558 | 2-(3'-C$_6$H$_5$—C$_6$H$_4$)-Oxazolyl-4 |
| 559 | 2-(2'-C$_6$H$_5$—C$_6$H$_4$)-Oxazolyl-4 |
| 560 | 2-(4'-Cl—C$_6$H$_4$)-Oxazolyl-4 |
| 561 | 2-(3'-Cl—C$_6$H$_4$)-Oxazolyl-4 |
| 562 | 2-(2'-Cl—C$_6$H$_4$)-Oxazolyl-4 |
| 563 | 2-(4'-Br—C$_6$H$_4$)-Oxazolyl-4 |
| 564 | 2-(3'-Br—C$_6$H$_4$)-Oxazolyl-4 |
| 565 | 2-(2'-Br—C$_6$H$_4$)-Oxazolyl-4 |
| 566 | 2-(4'-F—C$_6$H$_4$)-Oxazolyl-4 |
| 567 | 2-(3'-F—C$_6$H$_4$)-Oxazolyl-4 |
| 568 | 2-(2'-F—C$_6$H$_4$)-Oxazolyl-4 |
| 569 | 2-(3',4'-Cl$_2$—C$_6$H$_3$)-Oxazolyl-4 |
| 570 | 2-(2',4'-Cl$_2$—C$_6$H$_3$)-Oxazolyl-4 |
| 571 | 2-(3',4'-F$_2$—C$_6$H$_3$)-Oxazolyl-4 |
| 572 | 2-(2',4'-F$_2$—C$_6$H$_3$)-Oxazolyl-4 |
| 573 | 2-(2',6'-F$_2$—C$_6$H$_3$)-Oxazolyl-4 |
| 574 | 2-(5'-Cl-2'-CH$_3$O—C$_6$H$_3$)-Oxazolyl-4 |
| 575 | 2-CH$_3$-Thiazolyl-4 |
| 576 | 2-i-C$_3$H$_7$-Thiazolyl-4 |
| 577 | 2-t-C$_4$H$_9$-Thiazolyl-4 |
| 578 | 2-cyclo-C$_3$H$_9$-Thiazolyl-4 |
| 579 | 2-C$_6$H$_5$-Thiazolyl-4 |
| 580 | 2-(4'-CH$_3$—C$_6$H$_4$)-Thiazolyl-4 |
| 581 | 2-(3'-CH$_3$—C$_6$H$_4$)-Thiazolyl-4 |
| 582 | 2-(2'-CH$_3$—C$_6$H$_4$)-Thiazolyl-4 |
| 583 | 2-(4'-CH$_3$O—C$_6$H$_4$)-Thiazolyl-4 |
| 584 | 2-(3'-CH$_3$O—C$_6$H$_4$)-Thiazolyl-4 |
| 585 | 2-(2'-CH$_3$O—C$_6$H$_4$)-Thiazolyl-4 |
| 586 | 2-(4'-NO$_2$—C$_6$H$_4$)-Thiazolyl-4 |
| 587 | 2-(3'-NO$_2$—C$_6$H$_4$)-Thiazolyl-4 |
| 588 | 2-(2'-NO$_2$—C$_6$H$_4$)-Thiazolyl-4 |
| 589 | 2-(4'-CN—C$_6$H$_4$)-Thiazolyl-4 |
| 590 | 2-(3'-CN—C$_6$H$_4$)-Thiazolyl-4 |
| 591 | 2-(2'-CN—C$_6$H$_4$)-Thiazolyl-4 |
| 592 | 2-(4'-CF$_3$—C$_6$H$_4$)-Thiazolyl-4 |
| 593 | 2-(3'-CF$_3$—C$_6$H$_4$)-Thiazolyl-4 |
| 594 | 2-(2'-CF$_3$—C$_6$H$_4$)-Thiazolyl-4 |
| 595 | 2-(4'-t-C$_4$H$_9$—C$_6$H$_4$)-Thiazolyl-4 |
| 596 | 2-(3'-t-C$_4$H$_9$—C$_6$H$_4$)-Thiazolyl-4 |
| 597 | 2-(2'-t-C$_4$H$_9$—C$_6$H$_4$)-Thiazolyl-4 |
| 598 | 2-(4'-C$_6$H$_5$—C$_6$H$_4$)-Thiazolyl-4 |
| 599 | 2-(3'-C$_6$H$_5$—C$_6$H$_4$)-Thiazolyl-4 |
| 600 | 2-(2'-C$_6$H$_5$—C$_6$H$_4$)-Thiazolyl-4 |
| 601 | 2-(4'-Cl—C$_6$H$_4$)-Thiazolyl-4 |
| 602 | 2-(3'-Cl—C$_6$H$_4$)-Thiazolyl-4 |
| 603 | 2-(2'-Cl—C$_6$H$_4$)-Thiazolyl-4 |
| 604 | 2-(4'-Br—C$_6$H$_4$)-Thiazolyl-4 |
| 605 | 2-(3'-Br—C$_6$H$_4$)-Thiazolyl-4 |
| 606 | 2-(2'-Br—C$_6$H$_4$)-Thiazolyl-4 |
| 607 | 2-(4'-F—C$_6$H$_4$)-Thiazolyl-4 |
| 608 | 2-(3'-F—C$_6$H$_4$)-Thiazolyl-4 |
| 609 | 2-(2'-F—C$_6$H$_4$)-Thiazolyl-4 |
| 610 | 2-(3',4'-Cl$_2$—C$_6$H$_3$)-Thiazolyl-4 |
| 611 | 2-(2',4'-Cl$_2$—C$_6$H$_3$)-Thiazolyl-4 |
| 612 | 2-(3',4'-F$_2$—C$_6$H$_3$)-Thiazolyl-4 |
| 613 | 2-(2',4'-F$_2$—C$_6$H$_3$)-Thiazolyl-4 |
| 614 | 2-(2',6'-F$_2$—C$_6$H$_3$)-Thiazolyl-4 |
| 615 | 2-(5'-Cl-2'-CH$_3$O—C$_6$H$_3$)-Thiazolyl-4 |
| 616 | 3-CH$_3$—N—CH$_3$-1,2,4-Triazolyl-5 |
| 617 | 3-i-C$_3$H$_7$—N—CH$_3$-1,2,4-Triazolyl-5 |
| 618 | 3-t-C$_4$H$_9$—N—CH$_3$-1,2,4-Triazolyl-5 |
| 619 | 3-cyclo-C$_3$H$_9$—N—CH$_3$-1,2,4-Triazolyl-5 |
| 620 | 3-C$_6$H$_5$—N—CH$_3$-1,2,4-Triazolyl-5 |
| 621 | 3-(4'-CH$_3$—C$_6$H$_4$)—N—CH$_3$-1,2,4-Triazolyl-5 |
| 622 | 3-(3'-CH$_3$—C$_6$H$_4$)—N—CH$_3$-1,2,4-Triazolyl-5 |
| 623 | 3-(2'-CH$_3$—C$_6$H$_4$)—N—CH$_3$-1,2,4-Triazolyl-5 |
| 624 | 3-(4'-CH$_3$O—C$_6$H$_4$)—N—CH$_3$-1,2,4-Triazolyl-5 |
| 625 | 3-(3'-CH$_3$O—C$_6$H$_4$)—N—CH$_3$-1,2,4-Triazolyl-5 |
| 626 | 3-(2'-CH$_3$O—C$_6$H$_4$)—N—CH$_3$-1,2,4-Triazolyl-5 |
| 627 | 3-(4'-NO$_2$—C$_6$H$_4$)—N—CH$_3$-1,2,4-Triazolyl-5 |
| 628 | 3-(3'-NO$_2$—C$_6$H$_4$)—N—CH$_3$-1,2,4-Triazolyl-5 |
| 629 | 3-(2'-NO$_2$—C$_6$H$_4$)—N—CH$_3$-1,2,4-Triazolyl-5 |
| 630 | 3-(4'-CN—C$_6$H$_4$)—N—CH$_3$-1,2,4-Triazolyl-5 |
| 631 | 3-(3'-CN—C$_6$H$_4$)—N—CH$_3$-1,2,4-Triazolyl-5 |
| 632 | 3-(2'-CN—C$_6$H$_4$)—N—CH$_3$-1,2,4-Triazolyl-5 |
| 633 | 3-(4'-CF$_3$—C$_6$H$_4$)—N—CH$_3$-1,2,4-Triazolyl-5 |
| 634 | 3-(3'-CF$_3$—C$_6$H$_4$)—N—CH$_3$-1,2,4-Triazolyl-5 |
| 635 | 3-(2'-CF$_3$—C$_6$H$_4$)—N—CH$_3$-1,2,4-Triazolyl-5 |
| 636 | 3-(4'-t-C$_4$H$_9$—C$_6$H$_4$)—N—t-CH$_3$-1,2,4-Triazolyl-5 |
| 637 | 3-(3'-t-C$_4$H$_9$—C$_6$H$_4$)—N—t-CH$_3$-1,2,4-Triazolyl-5 |
| 638 | 3-(2'-t-C$_4$H$_9$—C$_6$H$_4$)—N—t-CH$_3$-1,2,4-Triazolyl-5 |
| 639 | 3-(4'-C$_6$H$_5$—C$_6$H$_4$)—N—CH$_3$-1,2,4-Triazolyl-5 |
| 640 | 3-(3'-C$_6$H$_5$—C$_6$H$_4$)—N—CH$_3$-1,2,4-Triazolyl-5 |
| 641 | 3-(2'-C$_6$H$_5$—C$_6$H$_4$)—N—CH$_3$-1,2,4-Triazolyl-5 |
| 642 | 3-(4'-Cl—C$_6$H$_4$)—N—CH$_3$-1,2,4-Triazolyl-5 |
| 643 | 3-(3'-Cl—C$_6$H$_4$)—N—CH$_3$-1,2,4-Triazolyl-5 |
| 644 | 3-(2'-Cl—C$_6$H$_4$)—N—CH$_3$-1,2,4-Triazolyl-5 |
| 645 | 3-(4'-Br—C$_6$H$_4$)—N—CH$_3$-1,2,4-Triazolyl-5 |
| 646 | 3-(3'-Br—C$_6$H$_4$)—N—CH$_3$-1,2,4-Triazolyl-5 |
| 647 | 3-(2'-Br—C$_6$H$_4$)—N—CH$_3$-1,2,4-Triazolyl-5 |
| 648 | 3-(4'-F—C$_6$H$_4$)—N—CH$_3$-1,2,4-Triazolyl-5 |
| 649 | 3-(3'-F—C$_6$H$_4$)—N—CH$_3$-1,2,4-Triazolyl-5 |
| 650 | 3-(2'-F—C$_6$H$_4$)—N—CH$_3$-1,2,4-Triazolyl-5 |
| 651 | 3-(3',4'-Cl$_2$—C$_6$H$_3$)—N—CH$_3$-1,2,4-Triazolyl-5 |
| 652 | 3-(2',4'-Cl$_2$—C$_6$H$_3$)—N—CH$_3$-1,2,4-Triazolyl-5 |
| 653 | 3-(3',4'-F$_2$—C$_6$H$_3$)—N—CH$_3$-1,2,4-Triazolyl-5 |
| 654 | 3-(2',4'-F$_2$—C$_6$H$_3$)—N—CH$_3$-1,2,4-Triazolyl-5 |
| 655 | 3-(2',6'-F$_2$—C$_6$H$_3$)—N—CH$_3$-1,2,4-Triazolyl-5 |

TABLE 2-continued

R—CH=C(—)—C(=U)—CO2CH3 structure with O ring

I: U: =CH—OCH3
II: U: =N—OCH3
III: U: =CH—CH3

| No. | R |
|---|---|
| 656 | 3-(5'-Cl-2'-CH3O—C6H3)—N—CH3-1,2,4-Triazolyl-5 |
| 657 | 5-CH3-1,3,4-Oxadiazolyl-2 |
| 658 | 5-i-C3H7-1,3,4-Oxadiazolyl-2 |
| 659 | 5-t-C4H9-1,3,4-Oxadiazolyl-2 |
| 660 | 5-cyclo-C3H5-1,3,4-Oxadiazolyl-2 |
| 661 | 5-C6H5-1,3,4-Oxadiazolyl-2 |
| 662 | 5-(4'-CH3—C6H4)-1,3,4-Oxadiazolyl-2 |
| 663 | 5-(3'-CH3—C6H4)-1,3,4-Oxadiazolyl-2 |
| 664 | 5-(2'-CH3—C6H4)-1,3,4-Oxadiazolyl-2 |
| 665 | 5-(4'-CH3O—C6H4)-1,3,4-Oxadiazolyl-2 |
| 666 | 5-(3'-CH3O—C6H4)-1,3,4-Oxadiazolyl-2 |
| 667 | 5-(2'-CH3O—C6H4)-1,3,4-Oxadiazolyl-2 |
| 668 | 5-(4'-NO2—C6H4)-1,3,4-Oxadiazolyl-2 |
| 669 | 5-(3'-NO2—C6H4)-1,3,4-Oxadiazolyl-2 |
| 670 | 5-(2'-NO2—C6H4)-1,3,4-Oxadiazolyl-2 |
| 671 | 5-(4'-CN—C6H4)-1,3,4-Oxadiazolyl-2 |
| 672 | 5-(3'-CN—C6H4)-1,3,4-Oxadiazolyl-2 |
| 673 | 5-(2'-CN—C6H4)-1,3,4-Oxadiazolyl-2 |
| 674 | 5-(4'-CF3—C6H4)-1,3,4-Oxadiazolyl-2 |
| 675 | 5-(3'-CF3—C6H4)-1,3,4-Oxadiazolyl-2 |
| 676 | 5-(2'-CF3—C6H4)-1,3,4-Oxadiazolyl-2 |
| 678 | 5-(4'-t-C4H9—C6H4)-1,3,4-Oxadiazolyl-2 |
| 679 | 5-(3'-t-C4H9—C6H4)-1,3,4-Oxadiazolyl-2 |
| 680 | 5-(2'-t-C4H9—C6H4)-1,3,4-Oxadiazolyl-2 |
| 681 | 5-(4'-C6H5—C6H4)-1,3,4-Oxadiazolyl-2 |
| 682 | 5-(3'-C6H5—C6H4)-1,3,4-Oxadiazolyl-2 |
| 683 | 5-(2'-C6H5—C6H4)-1,3,4-Oxadiazolyl-2 |
| 684 | 5-(4'-Cl—C6H4)-1,3,4-Oxadiazolyl-2 |
| 685 | 5-(3'-Cl—C6H4)-1,3,4-Oxadiazolyl-2 |
| 686 | 5-(2'-Cl—C6H4)-1,3,4-Oxadiazolyl-2 |
| 687 | 5-(4'-Br—C6H4)-1,3,4-Oxadiazolyl-2 |
| 688 | 5-(3'-Br—C6H4)-1,3,4-Oxadiazolyl-2 |
| 689 | 5-(2'-Br—C6H4)-1,3,4-Oxadiazolyl-2 |
| 690 | 5-(4'-F—C6H4)-1,3,4-Oxadiazolyl-2 |
| 691 | 5-(3'-F—C6H4)-1,3,4-Oxadiazolyl-2 |
| 692 | 5-(2'-F—C6H4)-1,3,4-Oxadiazolyl-2 |
| 693 | 5-(3',4'-Cl2—C6H3)-1,3,4-Oxadiazolyl-2 |
| 694 | 5-(2',4'-Cl2—C6H3)-1,3,4-Oxadiazolyl-2 |
| 695 | 5-(3',4'-F2—C6H3)-1,3,4-Oxadiazolyl-2 |
| 696 | 5-(2',4'-F2—C6H3)-1,3,4-Oxadiazolyl-2 |
| 697 | 5-(2',6'-F2—C6H3)-1,3,4-Oxadiazolyl-2 |
| 698 | 5-(5'-Cl-2'-CH3O—C6H3)-1,3,4-Oxadiazolyl-2 |
| 699 | 5-CH3-1,2,4-Oxadiazolyl-3 |
| 700 | 5-i-C3H7-1,2,4-Oxadiazolyl-3 |
| 701 | 5-t-C4H9-1,2,4-Oxadiazolyl-3 |
| 702 | 5-cyclo-C3H5-1,2,4-Oxadiazolyl-3 |
| 703 | 5-C6H5-1,2,4-Oxadiazolyl-3 |
| 704 | 5-(4'-CH3—C6H4)-1,2,4-Oxadiazolyl-3 |
| 705 | 5-(3'-CH3—C6H4)-1,2,4-Oxadiazolyl-3 |
| 706 | 5-(2'-CH3—C6H4)-1,2,4-Oxadiazolyl-3 |
| 707 | 5-(4'-CH3O—C6H4)-1,2,4-Oxadiazolyl-3 |
| 708 | 5-(3'-CH3O—C6H4)-1,2,4-Oxadiazolyl-3 |
| 709 | 5-(2'-CH3O—C6H4)-1,2,4-Oxadiazolyl-3 |
| 710 | 5-(4'-NO2—C6H4)-1,2,4-Oxadiazolyl-3 |
| 711 | 5-(3'-NO2—C6H4)-1,2,4-Oxadiazolyl-3 |
| 712 | 5-(2'-NO2—C6H4)-1,2,4-Oxadiazolyl-3 |
| 713 | 5-(4'-CN—C6H4)-1,2,4-Oxadiazolyl-3 |
| 714 | 5-(3'-CN—C6H4)-1,2,4-Oxadiazolyl-3 |
| 715 | 5-(2'-CN—C6H4)-1,2,4-Oxadiazolyl-3 |
| 716 | 5-(4'-CF3—C6H4)-1,2,4-Oxadiazolyl-3 |
| 717 | 5-(3'-CF3—C6H4)-1,2,4-Oxadiazolyl-3 |
| 718 | 5-(2'-CF3—C6H4)-1,2,4-Oxadiazolyl-3 |
| 719 | 5-(4'-t-C4H9—C6H4)-1,2,4-Oxadiazolyl-3 |
| 720 | 5-(3'-t-C4H9—C6H4)-1,2,4-Oxadiazolyl-3 |
| 721 | 5-(2'-t-C4H9—C6H4)-1,2,4-Oxadiazolyl-3 |
| 722 | 5-(4'-C6H5—C6H4)-1,2,4-Oxadiazolyl-3 |
| 723 | 5-(3'-C6H5—C6H4)-1,2,4-Oxadiazolyl-3 |
| 724 | 5-(2'-C6H5—C6H4)-1,2,4-Oxadiazolyl-3 |
| 725 | 5-(4'-Cl—C6H4)-1,2,4-Oxadiazolyl-3 |
| 726 | 5-(3'-Cl—C6H4)-1,2,4-Oxadiazolyl-3 |
| 727 | 5-(2'-Cl—C6H4)-1,2,4-Oxadiazolyl-3 |
| 728 | 5-(4'-Br—C6H4)-1,2,4-Oxadiazolyl-3 |
| 729 | 5-(3'-Br—C6H4)-1,2,4-Oxadiazolyl-3 |
| 730 | 5-(2'-Br—C6H4)-1,2,4-Oxadiazolyl-3 |
| 731 | 5-(4'-F—C6H4)-1,2,4-Oxadiazolyl-3 |
| 732 | 5-(3'-F—C6H4)-1,2,4-Oxadiazolyl-3 |
| 733 | 5-(2'-F—C6H4)-1,2,4-Oxadiazolyl-3 |
| 734 | 5-(3',4'-Cl2—C6H3)-1,2,4-Oxadiazolyl-3 |
| 735 | 5-(2',4'-Cl2—C6H3)-1,2,4-Oxadiazolyl-3 |
| 736 | 5-(3',4'-F2—C6H3)-1,2,4-Oxadiazolyl-3 |
| 737 | 5-(2',4'-F2—C6H3)-1,2,4-Oxadiazolyl-3 |
| 738 | 5-(2',6'-F2—C6H3)-1,2,4-Oxadiazolyl-3 |
| 739 | 5-(5'-Cl-2'-CH3O—C6H3)-1,2,4-Oxadiazolyl-3 |
| 740 | 3-CH3-1,2,4-Oxadiazolyl-5 |
| 741 | 3-i-C3H7-1,2,4-Oxadiazolyl-5 |
| 742 | 3-t-C4H9-1,2,4-Oxadiazolyl-5 |
| 743 | 3-cyclo-C3H5-1,2,4-Oxadiazolyl-5 |
| 744 | 3-C6H5-1,2,4-Oxadiazolyl-5 |
| 745 | 3-(4'-CH3—C6H4)-1,2,4-Oxadiazolyl-5 |
| 746 | 3-(3'-CH3—C6H4)-1,2,4-Oxadiazolyl-5 |
| 747 | 3-(2'-CH3—C6H4)-1,2,4-Oxadiazolyl-5 |
| 748 | 3-(4'-CH3O—C6H4)-1,2,4-Oxadiazolyl-5 |
| 749 | 3-(3'-CH3O—C6H4)-1,2,4-Oxadiazolyl-5 |
| 750 | 3-(2'-CH3O—C6H4)-1,2,4-Oxadiazolyl-5 |
| 751 | 3-(4'-NO2—C6H4)-1,2,4-Oxadiazolyl-5 |
| 752 | 3-(3'-NO2—C6H4)-1,2,4-Oxadiazolyl-5 |
| 753 | 3-(2'-NO2—C6H4)-1,2,4-Oxadiazolyl-5 |
| 754 | 3-(4'-CN—C6H4)-1,2,4-Oxadiazolyl-5 |
| 755 | 3-(3'-CN—C6H4)-1,2,4-Oxadiazolyl-5 |
| 756 | 3-(2'-CN—C6H4)-1,2,4-Oxadiazolyl-5 |
| 757 | 3-(4'-CF3—C6H4)-1,2,4-Oxadiazolyl-5 |
| 758 | 3-(3'-CF3—C6H4)-1,2,4-Oxadiazolyl-5 |
| 759 | 3-(2'-CF3—C6H4)-1,2,4-Oxadiazolyl-5 |
| 760 | 3-(4'-t-C4H9—C6H4)-1,2,4-Oxadiazolyl-5 |
| 761 | 3-(3'-t-C4H9—C6H4)-1,2,4-Oxadiazolyl-5 |
| 762 | 3-(2'-t-C4H9—C6H4)-1,2,4-Oxadiazolyl-5 |
| 763 | 3-(4'-C6H5—C6H4)-1,2,4-Oxadiazolyl-5 |
| 764 | 3-(3'-C6H5—C6H4)-1,2,4-Oxadiazolyl-5 |
| 765 | 3-(2'-C6H5—C6H4)-1,2,4-Oxadiazolyl-5 |
| 766 | 3-(4'-Cl—C6H4)-1,2,4-Oxadiazolyl-5 |
| 767 | 3-(3'-Cl—C6H4)-1,2,4-Oxadiazolyl-5 |
| 768 | 3-(2'-Cl—C6H4)-1,2,4-Oxadiazolyl-5 |
| 769 | 3-(4'-Br—C6H4)-1,2,4-Oxadiazolyl-5 |
| 770 | 3-(3'-Br—C6H4)-1,2,4-Oxadiazolyl-5 |
| 771 | 3-(2'-Br—C6H4)-1,2,4-Oxadiazolyl-5 |
| 772 | 3-(4'-F—C6H4)-1,2,4-Oxadiazolyl-5 |
| 773 | 3-(3'-F—C6H4)-1,2,4-Oxadiazolyl-5 |
| 774 | 3-(2'-F—C6H4)-1,2,4-Oxadiazolyl-5 |
| 775 | 3-(3',4'-Cl2—C6H3)-1,2,4-Oxadiazolyl-5 |
| 776 | 3-(2',4'-Cl2—C6H3)-1,2,4-Oxadiazolyl-5 |
| 777 | 3-(3',4'-F2—C6H3)-1,2,4-Oxadiazolyl-5 |
| 778 | 3-(2',4'-F2—C6H3)-1,2,4-Oxadiazolyl-5 |
| 779 | 3-(2',6'-F2—C6H3)-1,2,4-Oxadiazolyl-5 |
| 780 | 3-(5'-Cl-2'-CH3O—C6H3)-1,2,4-Oxadiazolyl-5 |
| 781 | 5-CH3-1,2,4-Thiadiazolyl-3 |
| 782 | 5-i-C3H7-1,2,4-Thiadiazolyl-3 |
| 783 | 5-t-C4H9-1,2,4-Thiadiazolyl-3 |
| 784 | 5-cyclo-C3H5-1,2,4-Thiadiazolyl-3 |
| 785 | 5-C6H5-1,2,4-Thiadiazolyl-3 |
| 786 | 5-(4'-CH3—C6H4)-1,2,4-Thiadiazolyl-3 |
| 787 | 5-(3'-CH3—C6H4)-1,2,4-Thiadiazolyl-3 |
| 788 | 5-(2'-CH3—C6H4)-1,2,4-Thiadiazolyl-3 |
| 789 | 5-(4'-CH3O—C6H4)-1,2,4-Thiadiazolyl-3 |
| 790 | 5-(3'-CH3O—C6H4)-1,2,4-Thiadiazolyl-3 |
| 791 | 5-(2'-CH3O—C6H4)-1,2,4-Thiadiazolyl-3 |
| 792 | 5-(4'-NO2—C6H4)-1,2,4-Thiadiazolyl-3 |
| 793 | 5-(3'-NO2—C6H4)-1,2,4-Thiadiazolyl-3 |
| 794 | 5-(2'-NO2—C6H4)-1,2,4-Thiadiazolyl-3 |

TABLE 2-continued

R—[structure: pyran ring with vinyl linkage, H₃CO₂C, U substituent]

I: U: =CH—OCH₃
II: U: =N—OCH₃
III: U: =CH—CH₃

| No. | R |
|---|---|
| 795 | 5-(4'-CN—C₆H₄)-1,2,4-Thiadiazolyl-3 |
| 796 | 5-(3'-CN—C₆H₄)-1,2,4-Thiadiazolyl-3 |
| 797 | 5-(2'-CN—C₆H₄)-1,2,4-Thiadiazolyl-3 |
| 798 | 5-(4'-CF₃—C₆H₄)-1,2,4-Thiadiazolyl-3 |
| 799 | 5-(3'-CF₃—C₆H₄)-1,2,4-Thiadiazolyl-3 |
| 800 | 5-(2'-CF₃—C₆H₄)-1,2,4-Thiadiazolyl-3 |
| 801 | 5-(4'-t-C₄H₉—C₆H₄)-1,2,4-Thiadiazolyl-3 |
| 802 | 5-(3'-t-C₄H₉—C₆H₄)-1,2,4-Thiadiazolyl-3 |
| 803 | 5-(2'-t-C₄H₉—C₆H₄)-1,2,4-Thiadiazolyl-3 |
| 804 | 5-(4'-C₆H₅—C₆H₄)-1,2,4-Thiadiazolyl-3 |
| 805 | 5-(3'-C₆H₅—C₆H₄)-1,2,4-Thiadiazolyl-3 |
| 806 | 5-(2'-C₆H₅—C₆H₄)-1,2,4-Thiadiazolyl-3 |
| 807 | 5-(4'-Cl—C₆H₄)-1,2,4-Thiadiazolyl-3 |
| 808 | 5-(3'-Cl—C₆H₄)-1,2,4-Thiadiazolyl-3 |
| 809 | 5-(2'-Cl—C₆H₄)-1,2,4-Thiadiazolyl-3 |
| 810 | 5-(4'-Br—C₆H₄)-1,2,4-Thiadiazolyl-3 |
| 811 | 5-(3'-Br—C₆H₄)-1,2,4-Thiadiazolyl-3 |
| 812 | 5-(2'-Br—C₆H₄)-1,2,4-Thiadiazolyl-3 |
| 813 | 5-(4'-F—C₆H₄)-1,2,4-Thiadiazolyl-3 |
| 814 | 5-(3'-F—C₆H₄)-1,2,4-Thiadiazolyl-3 |
| 815 | 5-(2'-F—C₆H₄)-1,2,4-Thiadiazolyl-3 |
| 816 | 5-(3',4'-Cl₂—C₆H₃)-1,2,4-Thiadiazolyl-3 |
| 817 | 5-(2',4'-Cl₂—C₆H₃)-1,2,4-Thiadiazolyl-3 |
| 818 | 5-(3',4'-F₂—C₆H₃)-1,2,4-Thiadiazolyl-3 |
| 819 | 5-(2',4'-F₂—C₆H₃)-1,2,4-Thiadiazolyl-3 |
| 820 | 5-(2',6'-F₂—C₆H₃)-1,2,4-Thiadiazolyl-3 |
| 821 | 5-(5'-Cl-2'-CH₃O—C₆H₃)-1,2,4-Thiadiazolyl-3 |
| 822 | 5-CH₃-1,3,4-Thiadiazolyl-2 |
| 823 | 5-i-C₃H₇-1,3,4-Thiadiazolyl-2 |
| 824 | 5-t-C₄H₉-1,3,4-Thiadiazolyl-2 |
| 825 | 5-cyclo-C₃H₅-1,3,4-Thiadiazolyl-2 |
| 826 | 5-C₆H₅-1,3,4-Thiadiazolyl-2 |
| 827 | 5-(4'-CH₃—C₆H₄)-1,3,4-Thiadiazolyl-2 |
| 828 | 5-(3'-CH₃—C₆H₄)-1,3,4-Thiadiazolyl-2 |
| 829 | 5-(2'-CH₃—C₆H₄)-1,3,4-Thiadiazolyl-2 |
| 830 | 5-(4'-CH₃O—C₆H₄)-1,3,4-Thiadiazolyl-2 |
| 831 | 5-(3'-CH₃O—C₆H₄)-1,3,4-Thiadiazolyl-2 |
| 832 | 5-(2'-CH₃O—C₆H₄)-1,3,4-Thiadiazolyl-2 |
| 833 | 5-(4'-NO₂—C₆H₄)-1,3,4-Thiadiazolyl-2 |
| 834 | 5-(3'-NO₂—C₆H₄)-1,3,4-Thiadiazolyl-2 |
| 835 | 5-(2'-NO₂—C₆H₄)-1,3,4-Thiadiazolyl-2 |
| 836 | 5-(4'-CN—C₆H₄)-1,3,4-Thiadiazolyl-2 |
| 837 | 5-(3'-CN—C₆H₄)-1,3,4-Thiadiazolyl-2 |
| 838 | 5-(2'-CN—C₆H₄)-1,3,4-Thiadiazolyl-2 |
| 839 | 5-(4'-CF₃—C₆H₄)-1,3,4-Thiadiazolyl-2 |
| 840 | 5-(3'-CF₃—C₆H₄)-1,3,4-Thiadiazolyl-2 |
| 841 | 5-(2'-CF₃—C₆H₄)-1,3,4-Thiadiazolyl-2 |
| 842 | 5-(4'-t-C₄H₉—C₆H₄)-1,3,4-Thiadiazolyl-2 |
| 843 | 5-(3'-t-C₄H₉—C₆H₄)-1,3,4-Thiadiazolyl-2 |
| 844 | 5-(2'-t-C₄H₉—C₆H₄)-1,3,4-Thiadiazolyl-2 |
| 845 | 5-(4'-C₆H₅—C₆H₄)-1,3,4-Thiadiazolyl-2 |
| 846 | 5-(3'-C₆H₅—C₆H₄)-1,3,4-Thiadiazolyl-2 |
| 847 | 5-(2'-C₆H₅—C₆H₄)-1,3,4-Thiadiazolyl-2 |
| 848 | 5-(4'-Cl—C₆H₄)-1,3,4-Thiadiazolyl-2 |
| 849 | 5-(3'-Cl—C₆H₄)-1,3,4-Thiadiazolyl-2 |
| 850 | 5-(2'-Cl—C₆H₄)-1,3,4-Thiadiazolyl-2 |
| 851 | 5-(4'-Br—C₆H₄)-1,3,4-Thiadiazolyl-2 |
| 852 | 5-(3'-Br—C₆H₄)-1,3,4-Thiadiazolyl-2 |
| 853 | 5-(2'-Br—C₆H₄)-1,3,4-Thiadiazolyl-2 |
| 854 | 5-(4'-F—C₆H₄)-1,3,4-Thiadiazolyl-2 |
| 855 | 5-(3'-F—C₆H₄)-1,3,4-Thiadiazolyl-2 |
| 856 | 5-(2'-F—C₆H₄)-1,3,4-Thiadiazolyl-2 |
| 857 | 5-(3',4'-Cl₂—C₆H₃)-1,3,4-Thiadiazolyl-2 |
| 858 | 5-(2',4'-Cl₂—C₆H₃)-1,3,4-Thiadiazolyl-2 |
| 859 | 5-(3',4'-F₂—C₆H₃)-1,3,4-Thiadiazolyl-2 |
| 860 | 5-(2',4'-F₂—C₆H₃)-1,3,4-Thiadiazolyl-2 |
| 861 | 5-(2',6'-F₂—C₆H₃)-1,3,4-Thiadiazolyl-2 |
| 862 | 5-(5'-Cl-2'-CH₃O—C₆H₃)-1,3,4-Thiadiazolyl-2 |
| 863 | Pyrryl-3 |
| 864 | Pyrryl-2 |
| 865 | Furyl-2 |
| 866 | Thienyl-2 |
| 867 | Thienyl-3 |
| 868 | Pyrazolyl-4 |
| 869 | Isoxazolyl-5 |
| 870 | 4-chloroisoxazolyl-5 |
| 871 | Isoxazolyl-3 |
| 872 | Isothiazolyl-5 |
| 873 | Oxazolyl-4 |
| 874 | Thiazolyl-4 |
| 875 | 1,2,4-Triazolyl-5 |
| 876 | 1,3,4-Oxadiazolyl-2 |
| 877 | 1,2,4-Oxadiazolyl-3 |
| 878 | 1,2,4-Oxadiazolyl-5 |
| 879 | 1,2,4-Thiadiazolyl-3 |
| 880 | 1,3,4-Thiadiazolyl-2 |

TABLE 3

Xₘ—[structure: phenoxymethyl-linked pyran with H₃CO₂C, U substituent]

I: U: =CH—OCH₃
II: U: =N—OCH₃
III: U: =CH—CH₃

| No. | Xₘ |
|---|---|
| 1 | 2-F |
| 2 | 3-F |
| 3 | 4-F |
| 4 | 2,4-F₂ |
| 5 | 2,4,6-F₃ |
| 6 | 2,3,4,5,6-F₃ |
| 7 | 2,3-F₂ |
| 8 | 2-Cl |
| 9 | 3-Cl |
| 10 | 4-Cl |
| 11 | 2,3-Cl₂ |
| 12 | 2,4-Cl₂ |
| 13 | 2,5-Cl₂ |
| 14 | 2,6-Cl₂ |
| 15 | 3,4-Cl₂ |
| 16 | 3,5-Cl₂ |
| 17 | 2,3,4-Cl₃ |
| 18 | 2,3,5-Cl₃ |
| 19 | 2,3,6-Cl₃ |
| 20 | 2,4,5-Cl₃ |
| 21 | 2,4,6-Cl₃ |
| 22 | 3,4,5-Cl₃ |
| 23 | 2,3,4,6-Cl₄ |
| 24 | 2,3,5,6-Cl₄ |
| 25 | 2,3,4,5,6-Cl₅ |
| 26 | 2-Br |
| 27 | 3-Br |
| 28 | 4-Br |
| 29 | 2,4-Br₂ |
| 30 | 2,5-Br₅ |
| 31 | 2,6-Br₂ |
| 32 | 2,4,6-Br₃ |
| 33 | 2,3,4,5,6-Br₅ |
| 34 | 2-I |
| 35 | 3-I |
| 36 | 4-I |
| 37 | 2,4-I₂ |

TABLE 3-continued

Structure: Phenyl ring with $X_m$ substituent, connected via $-O-CH_2-$ to a dihydropyran ring bearing $H_3CO_2C-C(=U)-$ group.

I: U: =CH—OCH$_3$
II: U: =N—OCH$_3$
III: U: =CH—CH$_3$

| No. | $X_m$ |
|---|---|
| 38 | 2-Cl, 3-F |
| 39 | 2-Cl, 4-F |
| 40 | 2-Cl, 5-F |
| 41 | 2-Cl, 6-F |
| 42 | 2-Cl, 3-Br |
| 43 | 2-Cl, 4-Br |
| 44 | 2-Cl, 5-Br |
| 45 | 2-Cl, 6-Br |
| 46 | 2-Br, 3-Cl |
| 47 | 2-Br, 4-Cl |
| 48 | 2-Br, 5-Cl |
| 49 | 2-Br, 3-F |
| 50 | 2-Br, 4-F |
| 51 | 2-Br, 5-F |
| 52 | 2-Br, 6-F |
| 53 | 2-F, 3-Cl |
| 54 | 2-F, 4-Cl |
| 55 | 2-F, 5-Cl |
| 56 | 3-Cl, 4-F |
| 57 | 3-Cl, 5-F |
| 58 | 3-Cl, 4-Br |
| 59 | 3-Cl, 5-Br |
| 60 | 3-F, 4-Cl |
| 61 | 3-F, 4-Br |
| 62 | 3-Br, 4-Cl |
| 63 | 3-Br, 4-F |
| 64 | 2,6-Cl$_2$, 4-Br |
| 65 | 2-CH$_3$ |
| 66 | 3-CH$_3$ |
| 67 | 4-CH$_3$ |
| 68 | 2,3-(CH$_3$)$_2$ |
| 69 | 2,4-(CH$_3$)$_2$ |
| 70 | 2,5-(CH$_3$)$_2$ |
| 71 | 2,6-(CH$_3$)$_2$ |
| 72 | 3,4-(CH$_3$)$_2$ |
| 73 | 3,5-(CH$_3$)$_2$ |
| 74 | 2,3,5-(CH$_3$)$_3$ |
| 75 | 2,3,4-(CH$_3$)$_3$ |
| 76 | 2,3,6-(CH$_3$)$_3$ |
| 77 | 2,4,5-(CH$_3$)$_3$ |
| 78 | 2,4,6-(CH$_3$)$_3$ |
| 79 | 3,4,5-(CH$_3$)$_3$ |
| 80 | 2,3,4,6-(CH$_3$)$_4$ |
| 81 | 2,3,5,6-(CH$_3$)$_4$ |
| 82 | 2,3,4,5,6-(CH$_3$)$_5$ |
| 83 | 2-C$_2$H$_5$ |
| 84 | 3-C$_2$H$_5$ |
| 85 | 4-C$_2$H$_5$ |
| 86 | 2,4-(C$_2$H$_5$)$_2$ |
| 87 | 2,6-(C$_2$H$_5$)$_2$ |
| 88 | 3,5-(C$_2$H$_5$)$_2$ |
| 89 | 2,4,6-(C$_2$H$_5$)$_3$ |
| 90 | 2-n-C$_3$H$_7$ |
| 91 | 3-n-C$_3$H$_7$ |
| 92 | 4-n-C$_3$H$_7$ |
| 93 | 2-i-C$_3$H$_7$ |
| 94 | 3-i-C$_3$H$_7$ |
| 95 | 4-i-C$_3$H$_7$ |
| 96 | 2,4-(i-C$_3$H$_7$)$_2$ |
| 97 | 2,6-(i-C$_3$H$_7$)$_2$ |
| 98 | 3,5-(i-C$_3$H$_7$)$_2$ |
| 99 | 2,4,6-(i-C$_3$H$_7$)$_3$ |
| 100 | 2-s-C$_4$H$_9$ |
| 101 | 3-s-C$_4$H$_9$ |
| 102 | 4-s-C$_4$H$_9$ |
| 103 | 2-t-C$_4$H$_9$ |
| 104 | 3-t-C$_4$H$_9$ |
| 105 | 4-t-C$_4$H$_9$ |
| 106 | 2,3-(t-C$_4$H$_9$)$_2$ |
| 107 | 2,4-(t-C$_4$H$_9$)$_2$ |
| 108 | 2,5-(t-C$_4$H$_9$)$_2$ |
| 109 | 2,6-(t-C$_4$H$_9$)$_2$ |
| 110 | 3,4-(t-C$_4$H$_9$)$_2$ |
| 111 | 2,4,6-(t-C$_4$H$_9$)$_3$ |
| 112 | 4-n-C$_9$H$_{19}$ |
| 113 | 4-n-C$_{12}$H$_{25}$ |
| 114 | 4-n-C$_{15}$H$_{31}$ |
| 115 | 4-(1,1,3,3-Tetramethylbutyl) |
| 116 | 4-(2,4,4-Trimethylpropyl) |
| 117 | 2-t-C$_4$H$_9$, 4-CH$_3$ |
| 118 | 2-t-C$_4$H$_9$, 5-CH$_3$ |
| 119 | 2,6-(t-C$_4$H$_9$)$_2$, 4-CH$_3$ |
| 120 | 2-CH$_3$, 4-t-C$_4$H$_9$ |
| 121 | 2-CH$_3$, 6-t-C$_4$H$_9$ |
| 122 | 2-CH$_3$, 4-i-C$_3$H$_7$ |
| 123 | 2-CH$_3$, 5-i-C$_3$H$_7$ |
| 124 | 3-CH$_3$, 4-i-C$_3$H$_7$ |
| 125 | 2-i-C$_3$H$_7$, 5-CH$_3$ |
| 126 | 2,4-(t-C$_4$H$_9$)$_2$, 6-i-C$_3$H$_7$ |
| 127 | 2-Allyl |
| 128 | 3-Allyl |
| 129 | 4-Allyl |
| 130 | 2-Allyl, 6-CH$_3$ |
| 131 | 2-cyclo-C$_6$H$_{11}$ |
| 132 | 3-cyclo-C$_6$H$_{11}$ |
| 133 | 4-cyclo-C$_6$H$_{11}$ |
| 134 | 2,4-(cyclo-C$_6$H$_{11}$)$_2$, 6-CH$_3$ |
| 135 | 2-CH$_3$, 4-cyclo-C$_6$H$_{11}$ |
| 136 | 2-CH$_2$—C$_6$H$_5$ |
| 137 | 3-CH$_2$—C$_6$H$_5$ |
| 138 | 4-CH$_2$—C$_6$H$_5$ |
| 139 | 2-CH$_2$—C$_6$H$_5$, 4-CH$_3$ |
| 140 | 2-CH$_3$, 4-CH$_2$—C$_6$H$_5$ |
| 141 | 2-C$_6$H$_5$ |
| 142 | 3-C$_6$H$_5$ |
| 143 | 4-C$_6$H$_5$ |
| 144 | 4-(2-i-C$_3$H$_7$—C$_6$H$_4$) |
| 145 | 4-C$_6$H$_5$, 2,6-(CH$_3$)$_2$ |
| 146 | 2-Cl, 4-C$_6$H$_5$ |
| 147 | 2-Br, 4-C$_6$H$_5$ |
| 148 | 2-C$_6$H$_5$, 4-Cl |
| 149 | 2-C$_6$H$_5$, 4-Br |
| 150 | 2-CH$_2$C$_6$H$_5$, 4-Cl |
| 151 | 2-CH$_2$C$_6$H$_5$, 4-Br |
| 152 | 2-Cl, 4-CH$_2$C$_6$H$_5$ |
| 153 | 2-Br, 4-CH$_2$C$_6$H$_5$ |
| 154 | 2-cyclo-C$_6$H$_{11}$, 4-Cl |
| 155 | 2-cyclo-C$_6$H$_{11}$, 4-Br |
| 156 | 2-Cl, 4-cyclo-C$_6$H$_{11}$ |
| 157 | 2-Br, 4-cyclo-C$_6$H$_{11}$ |
| 158 | 2-OCH$_3$ |
| 159 | 3-OCH$_3$ |
| 160 | 4-OCH$_3$ |
| 161 | 2-OC$_2$H$_5$ |
| 162 | 3-O—C$_2$H$_5$ |
| 163 | 4-O—C$_2$H$_5$ |
| 164 | 2-O-n-C$_3$H$_7$ |
| 165 | 3-O-n-C$_3$H$_7$ |
| 166 | 4-O-n-C$_3$H$_7$ |
| 167 | 2-O-i-C$_3$H$_7$ |
| 168 | 3-O-i-C$_3$H$_7$ |
| 169 | 4-O-i-C$_3$H$_7$ |
| 170 | 2-O-n-C$_6$H$_{13}$ |
| 171 | 3-O-n-C$_6$H$_{13}$ |
| 172 | 4-O-n-C$_6$H$_{13}$ |
| 173 | 2-O-n-C$_8$H$_{17}$ |
| 174 | 3-O-n-C$_8$H$_{17}$ |
| 175 | 4-O-n-C$_8$H$_{17}$ |

TABLE 3-continued

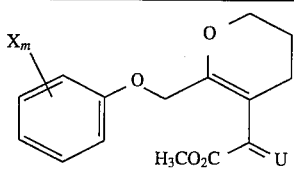

I: U: =CH—OCH$_3$
II: U: =N—OCH$_3$
III: U: =CH—CH$_3$

| No. | X$_m$ |
|---|---|
| 176 | 2-O—CH$_2$C$_6$H$_5$ |
| 177 | 3-O—CH$_2$C$_6$H$_5$ |
| 178 | 4-O—CH$_2$C$_6$H$_5$ |
| 179 | 2-O—(CH$_2$)$_3$C$_6$H$_5$ |
| 180 | 3-O—(CH$_2$)$_3$C$_6$H$_5$ |
| 181 | 4-O—(CH$_2$)$_3$C$_6$H$_5$ |
| 182 | 2,4-(OCH$_3$)$_2$ |
| 183 | 2-CF$_3$ |
| 184 | 3-CF$_3$ |
| 185 | 4-CF$_3$ |
| 186 | 2-OCF$_3$ |
| 187 | 3-OCF$_3$ |
| 188 | 4-OCF$_3$ |
| 189 | 3-OCH$_2$CHF$_2$ |
| 190 | 2-NO$_2$ |
| 191 | 3-NO$_2$ |
| 192 | 4-NO$_2$ |
| 193 | 2-CN |
| 194 | 3-CN |
| 195 | 4-CN |
| 196 | 2-CH$_3$, 3-Cl |
| 197 | 2-CH$_3$, 4-Cl |
| 198 | 2-CH$_3$, 5-Cl |
| 199 | 2-CH$_3$, 6-Cl |
| 200 | 2-CH$_3$, 3-F |
| 201 | 2-CH$_3$, 4-F |
| 202 | 2-CH$_3$, 5-F |
| 203 | 2-CH$_3$, 6-F |
| 204 | 2-CH$_3$, 3-Br |
| 205 | 2-CH$_3$, 4-Br |
| 206 | 2-CH$_3$, 5-Br |
| 207 | 2-CH$_3$, 6-Br |
| 208 | 2-Cl, 3-CH$_3$ |
| 209 | 2-Cl, 4-CH$_3$ |
| 210 | 2-Cl, 5-CH$_3$ |
| 211 | 2-F, 3-CH$_3$ |
| 212 | 2-F, 4-CH$_3$ |
| 213 | 2-F, 5-CH$_3$ |
| 214 | 2-Br, 3-CH$_3$ |
| 215 | 2-Br, 4-CH$_3$ |
| 216 | 2-Br, 5-CH$_3$ |
| 217 | 3-CH$_3$, 4-Cl |
| 218 | 3-CH$_3$, 5-Cl |
| 219 | 3-CH$_3$, 4-F |
| 220 | 3-CH$_3$, 5-F |
| 221 | 3-CH$_3$, 4-Br |
| 222 | 3-CH$_3$, 5-Br |
| 223 | 3-F, 4-CH$_3$ |
| 224 | 3-Cl, 4-CH$_3$ |
| 225 | 3-Br, 4-CH$_3$ |
| 226 | 2-Cl, 4,5-(CH$_3$)$_2$ |
| 227 | 2-Br, 4,5-(CH$_3$)$_2$ |
| 228 | 2-Cl, 3,5-(CH$_3$)$_2$ |
| 229 | 2-Br, 3,5-(CH$_3$)$_2$ |
| 230 | 2,6-Cl$_2$, 4-CH$_3$ |
| 231 | 2,6-F$_2$, 4-CH$_3$ |
| 232 | 2,6-Br$_2$, 4-CH$_3$ |
| 233 | 2,4-Br$_2$, 6-CH$_3$ |
| 234 | 2,4-F$_2$, 6-CH$_3$ |
| 235 | 2,4-Br$_2$, 6-CH$_3$ |
| 236 | 2,6-(CH$_3$)$_2$, 4-F |
| 237 | 2,6-(CH$_3$)$_2$, 4-Cl |
| 238 | 2,6-(CH$_3$)$_2$, 4-Br |
| 239 | 3,5-(CH$_3$)$_2$, 4-F |
| 240 | 3,5-(CH$_3$)$_2$, 4-Cl |
| 241 | 3,5-(CH$_3$)$_2$, 4-Br |
| 242 | 2,3,6-(CH$_3$)$_3$, 4-F |
| 243 | 2,3,6-(CH$_3$)$_3$, 4-Cl |
| 244 | 2,3,6-(CH$_3$)$_3$, 4-Br |

TABLE 3-continued

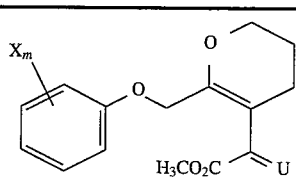

I: U: =CH—OCH$_3$
II: U: =N—OCH$_3$
III: U: =CH—CH$_3$

| No. | X$_m$ |
|---|---|
| 245 | 2,4-(CH$_3$)$_2$, 6-F |
| 246 | 2,4-(CH$_3$)$_2$, 6-Cl |
| 247 | 2,4-(CH$_3$)$_2$, 6-Br |
| 248 | 2-i-C$_3$H$_7$, 4-Cl, 5-CH$_3$ |
| 249 | 2-Cl, 4-NO$_2$ |
| 250 | 2-NO$_2$, 4-Cl |
| 251 | 2-OCH$_3$, 5-NO$_2$ |
| 252 | 2,4-Cl$_2$, 5-NO$_2$ |
| 253 | 2,4-Cl$_2$, 6-NO$_2$ |
| 254 | 2,4-Cl$_2$, 4-NO$_2$ |
| 255 | 2,6-Br$_2$, 4-NO$_2$ |
| 256 | 2,6-I$_2$, 4-NO$_2$ |
| 257 | 2-CH$_3$, 5-i-C$_3$H$_7$, 4-Cl |
| 258 | 2-Pyridyl-2 |
| 259 | 3-Pyridyl-2 |
| 260 | 4-Pyridyl-2 |
| 261 | 2-CO$_2$CH$_3$ |
| 262 | 3-CO$_2$CH$_3$ |
| 263 | 4-CO$_2$CH$_3$ |
| 264 | 2-CO$_2$(C$_2$H$_5$) |
| 265 | 3-CO$_2$(C$_2$H$_5$) |
| 266 | 4-CO$_2$(C$_2$H$_5$) |
| 267 | 2-CO$_2$(n-C$_3$H$_7$) |
| 268 | 3-CO$_2$(n-C$_3$H$_7$) |
| 269 | 4-CO$_2$(n-C$_3$H$_7$) |
| 270 | 2-CO$_2$(i-C$_3$H$_7$) |
| 271 | 3-CO$_2$(i-C$_3$H$_7$) |
| 272 | 4-CO$_2$(i-C$_3$H$_7$) |
| 273 | 2-CO$_2$(n-C$_6$H$_{13}$) |
| 274 | 3-CO$_2$(n-C$_6$H$_{13}$) |
| 275 | 4-CO$_2$(n-C$_6$H$_{13}$) |
| 276 | 2-CO$_2$(n-C$_8$H$_{17}$) |
| 277 | 3-CO$_2$(n-C$_8$H$_{17}$) |
| 278 | 4-CO$_2$(n-C$_8$H$_{17}$) |
| 279 | 2-CH$_2$OCH$_3$ |
| 280 | 3-CH$_2$OCH$_3$ |
| 281 | 4-CH$_2$OCH$_3$ |
| 282 | 2-CH$_2$O(C$_2$H$_5$) |
| 283 | 3-CH$_2$O(C$_2$H$_5$) |
| 284 | 4-CH$_2$O(C$_2$H$_5$) |
| 285 | 2-CH$_2$O(n-C$_3$H$_7$) |
| 286 | 3-CH$_2$O(n-C$_3$H$_7$) |
| 287 | 4-CH$_2$O(n-C$_3$H$_7$) |
| 288 | 2-CH$_2$O(i-C$_3$H$_7$) |
| 289 | 3-CH$_2$O(i-C$_3$H$_7$) |
| 290 | 4-CH$_2$O(i-C$_3$H$_7$) |
| 291 | 2-CH$_2$O(n-C$_6$H$_{13}$) |
| 292 | 3-CH$_2$O(n-C$_6$H$_{13}$) |
| 293 | 4-CH$_2$O(n-C$_6$H$_{13}$) |
| 294 | 2-CH$_2$O(n-C$_8$H$_{17}$) |
| 295 | 3-CH$_2$O(n-C$_8$H$_{17}$) |
| 296 | 4-CH$_2$O(n-C$_8$H$_{17}$) |
| 297 | 2-CH$_2$OCH$_2$(C$_6$H$_5$) |
| 298 | 3-CH$_2$OCH$_2$(C$_6$H$_5$) |
| 299 | 4-CH$_2$OCH$_2$(C$_6$H$_5$) |
| 300 | 2-CH$_2$O(CH$_2$)$_3$(C$_6$H$_5$) |
| 301 | 3-CH$_2$O(CH$_2$)$_3$(C$_6$H$_5$) |
| 302 | 4-CH$_2$O(CH$_2$)$_3$(C$_6$H$_5$) |
| 303 | 2-CHO |
| 304 | 3-CHO |
| 305 | 4-CHO |
| 306 | 2-CO—CH$_3$ |
| 307 | 3-CO—CH$_3$ |
| 308 | 4-CO—CH$_3$ |
| 309 | 2-CO—CH$_2$—CH$_3$ |
| 310 | 3-CO—CH$_2$—CH$_3$ |
| 311 | 4-CO—CH$_2$—CH$_3$ |
| 312 | 2-CO—CH$_2$—CH$_2$—CH$_3$ |
| 313 | 3-CO—CH$_2$—CH$_2$—CH$_3$ |

TABLE 3-continued

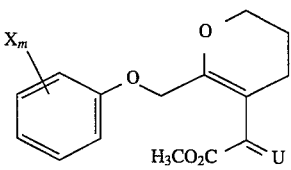

I: U: =CH—OCH₃
II: U: =N—OCH₃
III: U: =CH—CH₃

| No. | Xₘ |
|---|---|
| 314 | 4-CO—CH₂—CH₂—CH₃ |
| 315 | 2-CO—CH(CH₃)—CH₃ |
| 316 | 3-CO—CH(CH₃)—CH₃ |
| 317 | 4-CO—CH(CH₃)—CH₃ |
| 318 | 2-Me-4-CHO |
| 319 | 2-Me-4-CH₃—CO |
| 320 | 2-Me-4-CH₃—CH₂—CO |
| 321 | 2-Me-4-CH₃—CH₂—CH₂—CO |
| 322 | 2-Me-4-CH₃—CH(CH₃)—CO |
| 323 | 2,5-Me₂-4-CHO |
| 324 | 2,5-Me₂-4-CH₃—CO |
| 325 | 2,5-Me₂-4-CH₃—CH₂—CO |
| 326 | 2,5-Me₂-4-CH₃—CH₂—CH₂—CO |
| 327 | 2,5-Me₂-4-CH₃—CH(CH₃)—CO |
| 328 | 2-Cl-4-CHO |
| 329 | 2-Cl-4-CH₃—CO |
| 330 | 2-Cl-4-CH₃—CH₂—CO |
| 331 | 2-Cl-4-CH₃—CH₂—CH₂—CO |
| 332 | 2-Cl-4-CH₃—CH(CH₃)—CO |
| 333 | 2,5-Cl₂-4-CHO |
| 334 | 2,5-Cl₂-4-CH₃—CO |
| 335 | 2,5-Cl₂-4-CH₃—CH₂—CO |
| 336 | 2,5-Cl₂-4-CH₃—CH₂—CH₂—CO |
| 337 | 2,5-Cl₂-4-CH₃—CH(CH₃)—CO |
| 338 | 2-C(=NOCH₃)—CH₃ |
| 339 | 3-C(=NOCH₃)—CH₃ |
| 340 | 4-C(=NOCH₃)—CH₃ |
| 341 | 2-C(=NOC₂H₅)—CH₃ |
| 342 | 3-C(=NOC₂H₅)—CH₃ |
| 343 | 4-C(=NOC₂H₅)—CH₃ |
| 344 | 2-C(=NO-i-C₃H₇)—CH₃ |
| 345 | 3-C(=NO-i-C₃H₇)—CH₃ |
| 346 | 4-C(=NO-i-C₃H₇)—CH₃ |
| 347 | 2-C(=NO-Allyl)—CH₃ |
| 348 | 3-C(=NO-Allyl)—CH₃ |
| 349 | 4-C(=NO-Allyl)—CH₃ |
| 350 | 2-C(=NO-trans-chloroallyl)—CH₃ |
| 351 | 3-C(=NO-trans-chloroallyl)—CH₃ |
| 352 | 4-C(=NO-trans-chloroallyl)—CH₃ |
| 353 | 2-C(=NO-Propargyl)—CH₃ |
| 354 | 3-C(=NO-Propargyl)—CH₃ |
| 355 | 4-C(=NO-Propargyl)—CH₃ |
| 356 | 2-C(=NO—CH₂—C₆H₅)—CH₃ |
| 357 | 3-C(=NO—CH₂—C₆H₅)—CH₃ |
| 358 | 4-C(=NO—CH₂—C₆H₅)—CH₃ |
| 359 | 2-C(=NOCH₃)—C₂H₅ |
| 360 | 3-C(=NOCH₃)—C₂H₅ |
| 361 | 4-C(=NOCH₃)—C₂H₅ |
| 362 | 2-C(=NOC₂H₅)—C₂H₅ |
| 363 | 3-C(=NOC₂H₅)—C₂H₅ |
| 364 | 4-C(=NOC₂H₅)—C₂H₅ |
| 365 | 2-C(=NO-i-C₃H₇)—C₂H₅ |
| 366 | 3-C(=NO-i-C₃H₇)—C₂H₅ |
| 367 | 4-C(=NO-i-C₃H₇)—C₂H₅ |
| 368 | 2-C(=NO-Allyl)—C₂H₅ |
| 369 | 3-C(=NO-Allyl)—C₂H₅ |
| 370 | 4-C(=NO-Allyl)—C₂H₅ |
| 371 | 2-C(=NO-trans-chloroallyl)—C₂H₅ |
| 372 | 3-C(=NO-trans-chloroallyl)—C₂H₅ |
| 373 | 4-C(=NO-trans-chloroallyl)—C₂H₅ |
| 374 | 2-C(=NO-Propargyl)—C₂H₅ |
| 375 | 3-C(=NO-Propargyl)—C₂H₅ |
| 376 | 4-C(=NO-Propargyl)—C₂H₅ |
| 377 | 2-C(=NO—CH₂—C₆H₅)—C₂H₅ |
| 378 | 3-C(=NO—CH₂—C₆H₅)—C₂H₅ |
| 379 | 4-C(=NO—CH₂—C₆H₅)—C₂H₅ |
| 380 | 2-CH₃-4-CH=NOCH₃ |
| 381 | 2-CH₃-4-CH=NOC₂H₅ |
| 382 | 2-CH₃-4-CH=NO-i-C₃H₇ |

TABLE 3-continued

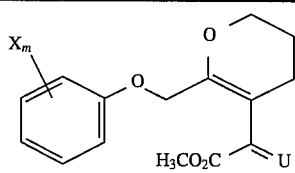

I: U: =CH—OCH₃
II: U: =N—OCH₃
III: U: =CH—CH₃

| No. | Xₘ |
|---|---|
| 383 | 2-CH₃-4-CH=NO-Allyl |
| 384 | 2-CH₃-4-CH=NO-(trans-chloroallyl) |
| 385 | 2-CH₃-4-CH=NO-Propargyl |
| 386 | 2-CH₃-4-CH=NO—CH₂—C₆H₅ |
| 387 | 2-CH₃-4-(CH₃—C=NOCH₃) |
| 388 | 2-CH₃-4-(CH₃—C=NOC₂H₅) |
| 389 | 2-CH₃-4-(CH₃—C=NO-i-C₃H₇) |
| 390 | 2-CH₃-4-(CH₃—C=NO-Allyl) |
| 391 | 2-CH₃-4-(CH₃—C=NO-trans-chloroallyl) |
| 392 | 2-CH₃-4-(CH₃—C=NO-Propargyl) |
| 393 | 2-CH₃-4-(CH₃—C=NO—CH₂—C₆H₅) |
| 394 | 2-CH₃-4-(C₂H₅—C=NO—CH₃) |
| 395 | 2-CH₃-4-(C₂H₅—C=NO—C₂H₅) |
| 396 | 2-CH₃-4-(C₂H₅—C=NO-i-C₃H₇) |
| 397 | 2-CH₃-4-(C₂H₅—C=NO-Allyl) |
| 398 | 2-CH₃-4-(C₂H₅—C=NO-trans-chloroallyl) |
| 399 | 2-CH₃-4-(C₂H₅—C=NO-Propargyl) |
| 400 | 2-CH₃-4-(C₂H₅—C=NO—CH₂C₆H₅) |
| 401 | 2,5-(CH₃)₂-4-(CH=NOCH₃) |
| 402 | 2,5-(CH₃)₂-4-(CH=NOC₂H₅) |
| 403 | 2,5-(CH₃)₂-4-(CH=NO-i-C₃H₇) |
| 404 | 2,5-(CH₃)₂-4-(CH=NO-Allyl) |
| 405 | 2,5-(CH₃)₂-4-(CH=NO-trans-chloroallyl) |
| 406 | 2,5-(CH₃)₂-4-(CH=NO-Propargyl) |
| 407 | 2,5-(CH₃)₂-4-(CH=NO—CH₂—C₆H₅) |
| 408 | 2,5-(CH₃)₂-4-(CH₃—C=NOCH₃) |
| 409 | 2,5-(CH₃)₂-4-(CH₃—C=NOC₂H₅) |
| 410 | 2,5-(CH₃)₂-4-(CH₃—C=NO-i-C₃H₇) |
| 411 | 2,5-(CH₃)₂-4-(CH₃—C=NO-Allyl) |
| 412 | 2,5-(CH₃)₂-4-(CH₃—C=NO-trans-chloroallyl) |
| 413 | 2,5-(CH₃)₂-4-(CH₃—C=NO-Propargyl) |
| 414 | 2,5-(CH₃)₂-4-(CH₃—C=NO—CH₂—C₆H₅) |
| 415 | 2,5-(CH₃)₂-4-(C₂H₅—C=NOCH₃) |
| 416 | 2,5-(CH₃)₂-4-(C₂H₅—C=NOC₂H₅) |
| 417 | 2,5-(CH₃)₂-4-(C₂H₅—C=NO-i-C₃H₇) |
| 418 | 2,5-(CH₃)₂-4-(C₂H₅—C=NO-Allyl) |
| 419 | 2,5-(CH₃)₂-4-(C₂H₅—C=NO-trans-chloroallyl) |
| 420 | 2,5-(CH₃)₂-4-(C₂H₅—C=NO-Propargyl) |
| 421 | 2,5-(CH₃)₂-4-(C₂H₅—C=NO—CH₂—C₆H₅) |
| 422 | H |

TABLE 4

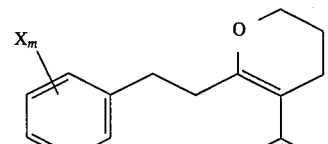

I: U: =CH—OCH₃
II: U: =N—OCH₃
III: U: =CH—CH₃

| No. | Xₘ |
|---|---|
| 1 | 2-F |
| 2 | 3-F |
| 3 | 4-F |
| 4 | 2,4-F₂ |
| 5 | 2,4,6-F₃ |
| 6 | 2,3,4,5,6-F₅ |
| 7 | 2,3-F₂ |
| 8 | 2-Cl |
| 9 | 3-Cl |
| 10 | 4-Cl |
| 11 | 2,3-Cl₂ |
| 12 | 2,4-Cl₂ |
| 13 | 2,5-Cl₂ |
| 14 | 2,6-Cl₂ |

TABLE 4-continued

Structure: phenyl with $X_m$ substituents, connected via $-CH_2CH_2-$ to a dihydropyran ring bearing $H_3CO_2C-C(=U)-$ group.

I: U: =CH—OCH$_3$
II: U: =N—OCH$_3$
III: U: =CH—CH$_3$

| No. | $X_m$ |
|---|---|
| 15 | 3,4-Cl$_2$ |
| 16 | 3,5-Cl$_2$ |
| 17 | 2,3,4-Cl$_3$ |
| 18 | 2,3,5-Cl$_3$ |
| 19 | 2,3,6-Cl$_3$ |
| 20 | 2,4,5-Cl$_3$ |
| 21 | 2,4,6-Cl$_3$ |
| 22 | 3,4,5-Cl$_3$ |
| 23 | 2,3,4,6-Cl$_4$ |
| 24 | 2,3,5,6-Cl$_4$ |
| 25 | 2,3,4,5,6-Cl$_5$ |
| 26 | 2-Br |
| 27 | 3-Br |
| 28 | 4-Br |
| 29 | 2,4-Br$_2$ |
| 30 | 2,5-Br$_5$ |
| 31 | 2,6-Br$_2$ |
| 32 | 2,4,6-Br$_3$ |
| 33 | 2,3,4,5,6-Br$_5$ |
| 34 | 2-I |
| 35 | 3-I |
| 36 | 4-I |
| 37 | 2,4-I$_2$ |
| 38 | 2-Cl, 3-F |
| 39 | 2-Cl, 4-F |
| 40 | 2-Cl, 5-F |
| 41 | 2-Cl, 6-F |
| 42 | 2-Cl, 3-Br |
| 43 | 2-Cl, 4-Br |
| 44 | 2-Cl, 5-Br |
| 45 | 2-Cl, 6-Br |
| 46 | 2-Br, 3-Cl |
| 47 | 2-Br, 4-Cl |
| 48 | 2-Br, 5-Cl |
| 49 | 2-Br, 3-F |
| 50 | 2-Br, 4-F |
| 51 | 2-Br, 5-F |
| 52 | 2-Br, 6-F |
| 53 | 2-F, 3-Cl |
| 54 | 2-F, 4-Cl |
| 55 | 2-F, 5-Cl |
| 56 | 3-Cl, 4-F |
| 57 | 3-Cl, 5-F |
| 58 | 3-Cl, 4-Br |
| 59 | 3-Cl, 5-Br |
| 60 | 3-F, 4-Cl |
| 61 | 3-F, 4-Br |
| 62 | 3-Br, 4-Cl |
| 63 | 3-Br, 4-F |
| 64 | 2,6-Cl$_2$, 4-Br |
| 65 | 2-CH$_3$ |
| 66 | 3-CH$_3$ |
| 67 | 4-CH$_3$ |
| 68 | 2,3-(CH$_3$)$_2$ |
| 69 | 2,4-(CH$_3$)$_2$ |
| 70 | 2,5-(CH$_3$)$_2$ |
| 71 | 2,6-(CH$_3$)$_2$ |
| 72 | 3,4-(CH$_3$)$_2$ |
| 73 | 3,5-(CH$_3$)$_2$ |
| 74 | 2,3,5-(CH$_3$)$_3$ |
| 75 | 2,3,4-(CH$_3$)$_3$ |
| 76 | 2,3,6-(CH$_3$)$_3$ |
| 77 | 2,4,5-(CH$_3$)$_3$ |
| 78 | 2,4,6-(CH$_3$)$_3$ |
| 79 | 3,4,5-(CH$_3$)$_3$ |
| 80 | 2,3,4,6-(CH$_3$)$_4$ |
| 81 | 2,3,5,6-(CH$_3$)$_4$ |
| 82 | 2,3,4,5,6-(CH$_3$)$_5$ |
| 83 | 2-C$_2$H$_5$ |
| 84 | 3-C$_2$H$_5$ |
| 85 | 4-C$_2$H$_5$ |
| 86 | 2,4-(C$_2$H$_5$)$_2$ |
| 87 | 2,6-(C$_2$H$_5$)$_2$ |
| 88 | 3,5-(C$_2$H$_5$)$_2$ |
| 89 | 2,4,6-(C$_2$H$_5$)$_3$ |
| 90 | 2-n-C$_3$H$_7$ |
| 91 | 3-n-C$_3$H$_7$ |
| 92 | 4-n-C$_3$H$_7$ |
| 93 | 2-i-C$_3$H$_7$ |
| 94 | 3-i-C$_3$H$_7$ |
| 95 | 4-i-C$_3$H$_7$ |
| 96 | 2,4-(i-C$_3$H$_7$)$_2$ |
| 97 | 2,6-(i-C$_3$H$_7$)$_2$ |
| 98 | 3,5-(i-C$_3$H$_7$)$_2$ |
| 99 | 2,4,6-(i-C$_3$H$_7$)$_3$ |
| 100 | 2-s-C$_4$H$_9$ |
| 101 | 3-s-C$_4$H$_9$ |
| 102 | 4-s-C$_4$H$_9$ |
| 103 | 2-t-C$_4$H$_9$ |
| 104 | 3-t-C$_4$H$_9$ |
| 105 | 4-t-C$_4$H$_9$ |
| 106 | 2,3-(t-C$_4$H$_9$)$_2$ |
| 107 | 2,4-(t-C$_4$H$_9$)$_2$ |
| 108 | 2,5-(t-C$_4$H$_9$)$_2$ |
| 109 | 2,6-(t-C$_4$H$_9$)$_2$ |
| 110 | 3,4-(t-C$_4$H$_9$)$_2$ |
| 111 | 2,4,6-(t-C$_4$H$_9$)$_3$ |
| 112 | 4-n-C$_9$H$_{19}$ |
| 113 | 4-n-C$_{12}$H$_{25}$ |
| 114 | 4-n-C$_{15}$H$_{31}$ |
| 115 | 4-(1,1,3,3-Tetramethylbutyl) |
| 116 | 4-(2,4,4-Trimethylpropyl) |
| 117 | 2-t-C$_4$H$_9$, 4-CH$_3$ |
| 118 | 2-t-C$_4$H$_9$, 5-CH$_3$ |
| 119 | 2,6-(t-C$_4$H$_9$)$_2$, 4-CH$_3$ |
| 120 | 2-CH$_3$, 4-t-C$_4$H$_9$ |
| 121 | 2-CH$_3$, 6-t-C$_4$H$_9$ |
| 122 | 2-CH$_3$, 4-i-C$_3$H$_7$ |
| 123 | 2-CH$_3$, 5-i-C$_3$H$_7$ |
| 124 | 2-CH$_3$, 4-i-C$_3$H$_7$ |
| 125 | 2-i-C$_3$H$_7$, 5-CH$_3$ |
| 126 | 2,4-(t-C$_4$H$_9$)$_2$, 6-i-C$_3$H$_7$ |
| 127 | 2-Allyl |
| 128 | 3-Allyl |
| 129 | 4-Allyl |
| 130 | 2-Allyl, 6-CH$_3$ |
| 131 | 2-cyclo-C$_6$H$_{11}$ |
| 132 | 3-cyclo-C$_6$H$_{11}$ |
| 133 | 4-cyclo-C$_6$H$_{11}$ |
| 134 | 2,4-(cyclo-C$_6$H$_{11}$)$_2$, 6-CH$_3$ |
| 135 | 2-CH$_3$, 4-cyclo-C$_6$H$_{11}$ |
| 136 | 2-CH$_2$—C$_6$H$_5$ |
| 137 | 3-CH$_2$—C$_6$H$_5$ |
| 138 | 4-CH$_2$—C$_6$H$_5$ |
| 139 | 2-CH$_2$—C$_6$H$_5$, 4-CH$_3$ |
| 140 | 2-CH$_3$, 4-CH$_2$—C$_6$H$_5$ |
| 141 | 2-C$_6$H$_5$ |
| 142 | 3-C$_6$H$_5$ |
| 143 | 4-C$_6$H$_5$ |
| 144 | 4-(2-i-C$_3$H$_7$—C$_6$H$_4$) |
| 145 | 4-C$_6$H$_5$, 2,6-(CH$_3$)$_2$ |
| 146 | 2-Cl, 4-C$_6$H$_5$ |
| 147 | 2-Br, 4-C$_6$H$_5$ |
| 148 | 2-C$_6$H$_5$, 4-Cl |
| 149 | 2-C$_6$H$_5$, 4-Br |
| 150 | 2-CH$_2$C$_6$H$_5$, 4-Cl |
| 151 | 2-CH$_2$C$_6$H$_5$, 4-Br |
| 152 | 2-Cl, 4-CH$_2$C$_6$H$_5$ |

TABLE 4-continued

I: U: =CH—OCH$_3$
II: U: =N—OCH$_3$
III: U: =CH—CH$_3$

| No. | X$_m$ |
|---|---|
| 153 | 2-Br, 4-CH$_2$C$_6$H$_5$ |
| 154 | 2-cyclo-C$_6$H$_{11}$, 4-Cl |
| 155 | 2-cyclo-C$_6$H$_{11}$, 4-Br |
| 156 | 2-Cl, 4-cyclo-C$_6$H$_{11}$ |
| 157 | 2-Br, 4-cyclo-C$_6$H$_{11}$ |
| 158 | 2-OCH$_3$ |
| 159 | 3-OCH$_3$ |
| 160 | 4-OCH$_3$ |
| 161 | 2-OC$_2$H$_5$ |
| 162 | 3-O—C$_2$H$_5$ |
| 163 | 4-O—C$_2$H$_5$ |
| 164 | 2-O-n-C$_3$H$_7$ |
| 165 | 3-O-n-C$_3$H$_7$ |
| 166 | 4-O-n-C$_3$H$_7$ |
| 167 | 2-O-i-C$_3$H$_7$ |
| 168 | 3-O-i-C$_3$H$_7$ |
| 169 | 4-O-i-C$_3$H$_7$ |
| 170 | 2-O-n-C$_6$H$_{13}$ |
| 171 | 3-O-n-C$_6$H$_{13}$ |
| 172 | 4-O-n-C$_6$H$_{13}$ |
| 173 | 2-O-n-C$_8$H$_{17}$ |
| 174 | 3-O-n-C$_8$H$_{17}$ |
| 175 | 4-O-n-C$_8$H$_{17}$ |
| 176 | 2-O—CH$_2$C$_6$H$_5$ |
| 177 | 3-O—CH$_2$C$_6$H$_5$ |
| 178 | 4-O—CH$_2$C$_6$H$_5$ |
| 179 | 2-O—(CH$_2$)$_3$C$_6$H$_5$ |
| 180 | 3-O—(CH$_2$)$_3$C$_6$H$_5$ |
| 181 | 4-O—(CH$_2$)$_3$C$_6$H$_5$ |
| 182 | 2,4-(OCH$_3$)$_2$ |
| 183 | 2-CF$_3$ |
| 184 | 3-CF$_3$ |
| 185 | 4-CF$_3$ |
| 186 | 2-OCF$_3$ |
| 187 | 3-OCF$_3$ |
| 188 | 4-OCF$_3$ |
| 189 | 3-OCH$_2$CHF$_2$ |
| 190 | 2-NO$_2$ |
| 191 | 3-NO$_2$ |
| 192 | 4-NO$_2$ |
| 193 | 2-CN |
| 194 | 3-CN |
| 195 | 4-CN |
| 196 | 2-CH$_3$, 3-Cl |
| 197 | 2-CH$_3$, 4-Cl |
| 198 | 2-CH$_3$, 5-Cl |
| 199 | 2-CH$_3$, 6-Cl |
| 200 | 2-CH$_3$, 3-F |
| 201 | 2-CH$_3$, 4-F |
| 202 | 2-CH$_3$, 5-F |
| 203 | 2-CH$_3$, 6-F |
| 204 | 2-CH$_3$, 3-Br |
| 205 | 2-CH$_3$, 4-Br |
| 206 | 2-CH$_3$, 5-Br |
| 207 | 2-CH$_3$, 6-Br |
| 208 | 2-Cl, 3-CH$_3$ |
| 209 | 2-Cl, 4-CH$_3$ |
| 210 | 2-Cl, 5-CH$_3$ |
| 211 | 2-F, 3-CH$_3$ |
| 212 | 2-F, 4-CH$_3$ |
| 213 | 2-F, 5-CH$_3$ |
| 214 | 2-Br, 3-CH$_3$ |
| 215 | 2-Br, 4-CH$_3$ |
| 216 | 2-Br, 5-CH$_3$ |
| 217 | 3-CH$_3$, 4-Cl |
| 218 | 3-CH$_3$, 5-Cl |
| 219 | 3-CH$_3$, 4-F |
| 220 | 3-CH$_3$, 5-F |
| 221 | 3-CH$_3$, 4-Br |
| 222 | 3-CH$_3$, 5-Br |
| 223 | 3-F, 4-CH$_3$ |
| 224 | 3-Cl, 4-CH$_3$ |
| 225 | 3-Br, 4-CH$_3$ |
| 226 | 2-Cl, 4,5-(CH$_3$)$_2$ |
| 227 | 2-Br, 4,5-(CH$_3$)$_2$ |
| 228 | 2-Cl, 3,5-(CH$_3$)$_2$ |
| 229 | 2-Br, 3,5-(CH$_3$)$_2$ |
| 230 | 2,6-Cl$_2$, 4-CH$_3$ |
| 231 | 2,6-F$_2$, 4-CH$_3$ |
| 232 | 2,6-Br$_2$, 4-CH$_3$ |
| 233 | 2,4-Br$_2$, 6-CH$_3$ |
| 234 | 2,4-F$_2$, 6-CH$_3$ |
| 235 | 2,4-Br$_2$, 6-CH$_3$ |
| 236 | 2,6-(CH$_3$)$_2$, 4-F |
| 237 | 2,6-(CH$_3$)$_2$, 4-Cl |
| 238 | 2,6-(CH$_3$)$_2$, 4-Br |
| 239 | 3,5-(CH$_3$)$_2$, 4-F |
| 240 | 3,5-(CH$_3$)$_2$, 4-Cl |
| 241 | 3,5-(CH$_3$)$_2$, 4-Br |
| 242 | 2,3,6-(CH$_3$)$_3$, 4-F |
| 243 | 2,3,6-(CH$_3$)$_3$, 4-Cl |
| 244 | 2,3,6-(CH$_3$)$_3$, 4-Br |
| 245 | 2,4-(CH$_3$)$_2$, 6-F |
| 246 | 2,4-(CH$_3$)$_2$, 6-Cl |
| 247 | 2,4-(CH$_3$)$_2$, 6-Br |
| 248 | 2-i-C$_3$H$_7$, 4-Cl, 5-CH$_3$ |
| 249 | 2-Cl, 4-NO$_2$ |
| 250 | 2-NO$_2$, 4-Cl |
| 251 | 2-OCH$_3$, 5-NO$_2$ |
| 252 | 2,4-Cl$_2$, 5-NO$_2$ |
| 253 | 2,4-Cl$_2$, 6-NO$_2$ |
| 254 | 2,6-Cl$_2$, 4-NO$_2$ |
| 255 | 2,6-Br$_2$, 4-NO$_2$ |
| 256 | 2,6-I$_2$, 4-NO$_2$ |
| 257 | 2-CH$_3$, 5-i-C$_3$H$_7$, 4-Cl |
| 258 | 2-Pyridyl-2 |
| 259 | 3-Pyridyl-2 |
| 260 | 4-Pyridyl-2 |
| 261 | 2-CO$_2$CH$_3$ |
| 262 | 3-CO$_2$CH$_3$ |
| 263 | 4-CO$_2$CH$_3$ |
| 264 | 2-CO$_2$(C$_2$H$_5$) |
| 265 | 3-CO$_2$(C$_2$H$_5$) |
| 266 | 4-CO$_2$(C$_2$H$_5$) |
| 267 | 2-CO$_2$(n-C$_3$H$_7$) |
| 268 | 3-CO$_2$(n-C$_3$H$_7$) |
| 269 | 4-CO$_2$(n-C$_3$H$_7$) |
| 270 | 2-CO$_2$(i-C$_3$H$_7$) |
| 271 | 3-CO$_2$(i-C$_3$H$_7$) |
| 272 | 4-CO$_2$(i-C$_3$H$_7$) |
| 273 | 2-CO$_2$(n-C$_6$H$_{13}$) |
| 274 | 3-CO$_2$(n-C$_6$H$_{13}$) |
| 275 | 4-CO$_2$(n-C$_6$H$_{13}$) |
| 276 | 2-CO$_2$(n-C$_8$H$_{17}$) |
| 277 | 3-CO$_2$(n-C$_8$H$_{17}$) |
| 278 | 4-CO$_2$(n-C$_8$H$_{17}$) |
| 279 | 2-CH$_2$OCH$_3$ |
| 280 | 3-CH$_2$OCH$_3$ |
| 281 | 4-CH$_2$OCH$_3$ |
| 282 | 2-CH$_2$O(C$_2$H$_5$) |
| 283 | 3-CH$_2$O(C$_2$H$_5$) |
| 284 | 4-CH$_2$O(C$_2$H$_5$) |
| 285 | 2-CH$_2$O(n-C$_3$H$_7$) |
| 286 | 3-CH$_2$O(n-C$_3$H$_7$) |
| 287 | 4-CH$_2$O(n-C$_3$H$_7$) |
| 288 | 2-CH$_2$O(i-C$_3$H$_7$) |
| 289 | 3-CH$_2$O(i-C$_3$H$_7$) |
| 290 | 4-CH$_2$O(i-C$_3$H$_7$) |

TABLE 4-continued

I: U: =CH—OCH₃
II: U: =N—OCH₃
III: U: =CH—CH₃

| No. | $X_m$ |
|---|---|
| 291 | 2-CH₂O(n-C₆H₁₃) |
| 292 | 3-CH₂O(n-C₆H₁₃) |
| 293 | 4-CH₂O(n-C₆H₁₃) |
| 294 | 2-CH₂O(n-C₈H₁₇) |
| 295 | 3-CH₂O(n-C₈H₁₇) |
| 296 | 4-CH₂O(n-C₈H₁₇) |
| 297 | 2-CH₂OCH₂(C₆H₅) |
| 298 | 3-CH₂OCH₂(C₆H₅) |
| 299 | 4-CH₂OCH₂(C₆H₅) |
| 300 | 2-CH₂O(CH₂)₃(C₆H₅) |
| 301 | 3-CH₂O(CH₂)₃(C₆H₅) |
| 302 | 4-CH₂O(CH₂)₃(C₆H₅) |
| 303 | 2-CHO |
| 304 | 3-CHO |
| 305 | 4-CHO |
| 306 | 2-CO—CH₃ |
| 307 | 3-CO—CH₃ |
| 308 | 4-CO—CH₃ |
| 309 | 2-CO—CH₂—CH₃ |
| 310 | 3-CO—CH₂—CH₃ |
| 311 | 4-CO—CH₂—CH₃ |
| 312 | 2-CO—CH₂—CH₂—CH₃ |
| 313 | 3-CO—CH₂—CH₂—CH₃ |
| 314 | 4-CO—CH₂—CH₂—CH₃ |
| 315 | 2-CO—CH(CH₃)—CH₃ |
| 316 | 3-CO—CH(CH₃)—CH₃ |
| 317 | 4-CO—CH(CH₃)—CH₃ |
| 318 | 2-Me-4-CHO |
| 319 | 2-Me-4-CH₃—CO |
| 320 | 2-Me-4-CH₃—CH₂—CO |
| 321 | 2-Me-4-CH₃—CH₂—CH₂—CO |
| 322 | 2-Me-4-CH₃—CH(CH₃)—CO |
| 323 | 2,5-Me₂-4-CHO |
| 324 | 2,5-Me₂-4-CH₃—CO |
| 325 | 2,5-Me₂-4-CH₃—CH₂—CO |
| 326 | 2,5-Me₂-4-CH₃—CH₂—CH₂—CO |
| 327 | 2,5-Me₂-4-CH₃—CH(CH₃)—CO |
| 328 | 2-Cl-4-CHO |
| 329 | 2-Cl-4-CH₃—CO |
| 330 | 2-Cl-4-CH₃—CH₂—CO |
| 331 | 2-Cl-4-CH₃—CH₂—CH₂—CO |
| 332 | 2-Cl-4-CH₃—CH(CH₃)—CO |
| 333 | 2,5-Cl₂-4-CHO |
| 334 | 2,5-Cl₂-4-CH₃—CO |
| 335 | 2,5-Cl₂-4-CH₃—CH₂—CO |
| 336 | 2,5-Cl₂-4-CH₃—CH₂—CH₂—CO |
| 337 | 2,5-Cl₂-4-CH₃—CH(CH₃)—CO |
| 338 | 2-C(=NOCH₃)—CH₃ |
| 339 | 3-C(=NOCH₃)—CH₃ |
| 340 | 4-C(=NOCH₃)—CH₃ |
| 341 | 2-C(=NOC₂H₅)—CH₃ |
| 342 | 3-C(=NOC₂H₅)—CH₃ |
| 343 | 4-C(=NOC₂H₅)—CH₃ |
| 344 | 2-C(=NO-i-C₃H₇)—CH₃ |
| 345 | 3-C(=NO-i-C₃H₇)—CH₃ |
| 346 | 4-C(=NO-i-C₃H₇)—CH₃ |
| 347 | 2-C(=NO-Allyl)—CH₃ |
| 348 | 3-C(=NO-Allyl)—CH₃ |
| 349 | 4-C(=NO-Allyl)—CH₃ |
| 350 | 2-C(=NO-trans-chloroallyl)—CH₃ |
| 351 | 3-C(=NO-trans-chloroallyl)—CH₃ |
| 352 | 4-C(=NO-trans-chloroallyl)—CH₃ |
| 353 | 2-C(=NO-Propargyl)—CH₃ |
| 354 | 3-C(=NO-Propargyl)—CH₃ |
| 355 | 4-C(=NO-Propargyl)—CH₃ |
| 356 | 2-C(=NO—CH₂—C₆H₅)—CH₃ |
| 357 | 3-C(=NO—CH₂—C₆H₅)—CH₃ |
| 358 | 4-C(=NO—CH₂—C₆H₅)—CH₃ |
| 359 | 2-C(=NOCH₃)—C₂H₅ |
| 360 | 3-C(=NOCH₃)—C₂H₅ |
| 361 | 4-C(=NOCH₃)—C₂H₅ |
| 362 | 2-C(=NOC₂H₅)—C₂H₅ |
| 363 | 3-C(=NOC₂H₅)—C₂H₅ |
| 364 | 4-C(=NOC₂H₅)—C₂H₅ |
| 365 | 2-C(=NO-i-C₃H₇)—C₂H₅ |
| 366 | 3-C(=NO-i-C₃H₇)—C₂H₅ |
| 367 | 4-C(=NO-i-C₃H₇)—C₂H₅ |
| 368 | 2-C(=NO-Allyl)—C₂H₅ |
| 369 | 3-C(=NO-Allyl)—C₂H₅ |
| 370 | 4-C(=NO-Allyl)—C₂H₅ |
| 371 | 2-C(=NO-trans-chloroallyl)—C₂H₅ |
| 372 | 3-C(=NO-trans-chloroallyl)—C₂H₅ |
| 373 | 4-C(=NO-trans-chloroallyl)—C₂H₅ |
| 374 | 2-C(=NO-Propargyl)—C₂H₅ |
| 375 | 3-C(=NO-Propargyl)—C₂H₅ |
| 376 | 4-C(=NO-Propargyl)—C₂H₅ |
| 377 | 2-C(=NO—CH₂—C₆H₅)—C₂H₅ |
| 378 | 3-C(=NO—CH₂—C₆H₅)—C₂H₅ |
| 379 | 4-C(=NO—CH₂—C₆H₅)—C₂H₅ |
| 380 | 2-CH₃-4-CH=NOCH₃ |
| 381 | 2-CH₃-4-CH=NOC₂H₅ |
| 382 | 2-CH₃-4-CH=NO-i-C₃H₇ |
| 383 | 2-CH₃-4-CH=NO-Allyl |
| 384 | 2-CH₃-4-CH=NO-(trans-chloroallyl) |
| 385 | 2-CH₃-4-CH=NO-Propargyl |
| 386 | 2-CH₃-4-CH=NO—CH₂—C₆H₅ |
| 387 | 2-CH₃-4-(CH₃—C=NOCH₃) |
| 388 | 2-CH₃-4-(CH₃—C=NOC₂H₅) |
| 389 | 2-CH₃-4-(CH₃—C=NO-i-C₃H₇) |
| 390 | 2-CH₃-4-(CH₃—C=NO-Allyl) |
| 391 | 2-CH₃-4-(CH₃—C=NO-trans-chloroallyl) |
| 392 | 2-CH₃-4-(CH₃—C=NO-Propargyl) |
| 393 | 2-CH₃-4-(CH₃—C=NO—CH₂—C₆H₅) |
| 394 | 2-CH₃-4-(C₂H₅—C=NO—CH₃) |
| 395 | 2-CH₃-4-(C₂H₅—C=NO—C₂H₅) |
| 396 | 2-CH₃-4-(C₂H₅—C=NO-i-C₃H₇) |
| 397 | 2-CH₃-4-(C₂H₅—C=NO-Allyl) |
| 398 | 2-CH₃-4-(C₂H₅—C=NO-trans-chloroallyl) |
| 399 | 2-CH₃-4-(C₂H₅—C=NO-Propargyl) |
| 400 | 2-CH₃-4-(C₂H₅—C=NO—CH₂—C₆H₅) |
| 401 | 2,5-(CH₃)₂-4-(CH=NOCH₃) |
| 402 | 2,5-(CH₃)₂-4-(CH=NOC₂H₅) |
| 403 | 2,5-(CH₃)₂-4-(CH=NO-i-C₃H₇) |
| 404 | 2,5-(CH₃)₂-4-(CH=NO-Allyl) |
| 405 | 2,5-(CH₃)₂-4-(CH=NO-trans-chloroallyl) |
| 406 | 2,5-(CH₃)₂-4-(CH=NO-Propargyl) |
| 407 | 2,5-(CH₃)₂-4-(CH=NO—CH₂—C₆H₅) |
| 408 | 2,5-(CH₃)₂-4-(CH₃—C=NOCH₃) |
| 409 | 2,5-(CH₃)₂-4-(CH₃—C=NOC₂H₅) |
| 410 | 2,5-(CH₃)₂-4-(CH₃—C=NO-i-C₃H₇) |
| 411 | 2,5-(CH₃)₂-4-(CH₃—C=NO-Allyl) |
| 412 | 2,5-(CH₃)₂-4-(CH₃—C=NO-trans-chloroallyl) |
| 413 | 2,5-(CH₃)₂-4-(CH₃—C=NO-Propargyl) |
| 414 | 2,5-(CH₃)₂-4-(CH₃—C=NO—CH₂—C₆H₅) |
| 415 | 2,5-(CH₃)₂-4-(C₂H₅—C=NOCH₃) |
| 416 | 2,5-(CH₃)₂-4-(C₂H₅—C=NOC₂H₅) |
| 417 | 2,5-(CH₃)₂-4-(C₂H₅—C=NO-i-C₃H₇) |
| 418 | 2,5-(CH₃)₂-4-(C₂H₅—C=NO-Allyl) |
| 419 | 2,5-(CH₃)₂-4-(C₂H₅—C=NO-trans-chloroallyl) |
| 420 | 2,5-(CH₃)₂-4-(C₂H₅—C=NO-Propargyl) |
| 421 | 2,5-(CH₃)₂-4-(C₂H₅—C=NO—CH₂—C₆H₅) |
| 422 | H |

TABLE 5

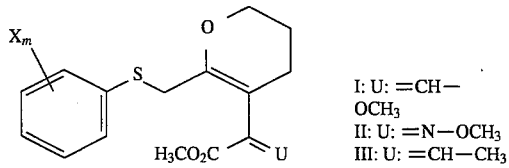

I: U: =CH—OCH$_3$
II: U: =N—OCH$_3$
III: U: =CH—CH$_3$

| No. | X$_m$ |
|---|---|
| 1 | 2-F |
| 2 | 3-F |
| 3 | 4-F |
| 4 | 2,4-F$_2$ |
| 5 | 2,4,6-F$_3$ |
| 6 | 2,3,4,5,6-F$_5$ |
| 7 | 2,3-F$_2$ |
| 8 | 2-Cl |
| 9 | 3-Cl |
| 10 | 4-Cl |
| 11 | 2,3-Cl$_2$ |
| 12 | 2,4-Cl$_2$ |
| 13 | 2,5-Cl$_2$ |
| 14 | 2,6-Cl$_2$ |
| 15 | 3,4-Cl$_2$ |
| 16 | 3,5-Cl$_2$ |
| 17 | 2,3,4-Cl$_3$ |
| 18 | 2,3,5-Cl$_3$ |
| 19 | 2,3,6-Cl$_3$ |
| 20 | 2,4,5-Cl$_3$ |
| 21 | 2,4,6-Cl$_3$ |
| 22 | 3,4,5-Cl |
| 23 | 2,3,4,6-Cl$_4$ |
| 24 | 2,3,4,6-Cl$_4$ |
| 25 | 2,3,4,5,6-Cl$_5$ |
| 26 | 2-Br |
| 27 | 3-Br |
| 28 | 4-Br |
| 29 | 2,4-Br$_2$ |
| 30 | 2,5-Br$_2$ |
| 31 | 2,6-Br$_2$ |
| 32 | 2,4,6-Br$_3$ |
| 33 | 2,3,4,5,6-Br$_5$ |
| 34 | 2-I |
| 35 | 3-I |
| 36 | 4-I |
| 37 | 2,4-I$_2$ |
| 38 | 2-Cl, 3-F |
| 39 | 2-Cl, 4-F |
| 40 | 2-Cl, 5-F |
| 41 | 2-Cl, 6-F |
| 42 | 2-Cl, 3-Br |
| 43 | 2-Cl, 4-Br |
| 44 | 2-Cl, 5-Br |
| 45 | 2-Cl, 6-Br |
| 46 | 2-Br, 3-Cl |
| 47 | 2-Br, 4-Cl |
| 48 | 2-Br, 5-Cl |
| 49 | 2-Br, 3-F |
| 50 | 2-Br, 4-F |
| 51 | 2-Br, 5-F |
| 52 | 2-Br, 6-F |
| 53 | 2-F, 3-Cl |
| 54 | 2-F, 4-Cl |
| 55 | 2-F, 5-Cl |
| 56 | 3-Cl, 4-F |
| 57 | 3-Cl, 5-F |
| 58 | 3-Cl, 4-Br |
| 59 | 3-Cl, 5-Br |
| 60 | 3-F, 4-Cl |
| 61 | 3-F, 4-Br |
| 62 | 3-Br, 4-Cl |
| 63 | 3-Br, 4-F |
| 64 | 2,6-Cl$_2$, 4-Br |
| 65 | 2-CH$_3$ |
| 66 | 3-CH$_3$ |
| 67 | 4-CH$_3$ |
| 68 | 2,3-(CH$_3$)$_2$ |
| 69 | 2,4-(CH$_3$)$_2$ |

TABLE 5-continued

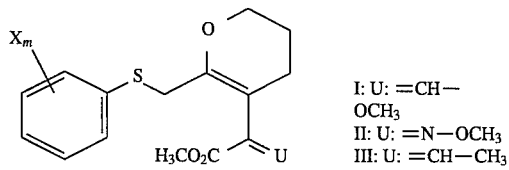

I: U: =CH—OCH$_3$
II: U: =N—OCH$_3$
III: U: =CH—CH$_3$

| No. | X$_m$ |
|---|---|
| 70 | 2,5-(CH$_3$)$_2$ |
| 71 | 2,6-(CH$_3$)$_2$ |
| 72 | 3,4-(CH$_3$)$_2$ |
| 73 | 3,5-(CH$_3$)$_2$ |
| 74 | 2,3,5-(CH$_3$)$_3$ |
| 75 | 2,3,4-(CH$_3$)$_3$ |
| 76 | 2,3,6-(CH$_3$)$_3$ |
| 77 | 2,4,5-(CH$_3$)$_3$ |
| 78 | 2,4,6-(CH$_3$)$_3$ |
| 79 | 3,4,5-(CH$_3$)$_3$ |
| 80 | 2,3,4,6-(CH$_3$)$_4$ |
| 81 | 2,3,5,6-(CH$_3$)$_4$ |
| 82 | 2,3,4,5,6-(CH$_3$)$_5$ |
| 83 | 2-C$_2$H$_5$ |
| 84 | 3-C$_2$H$_5$ |
| 85 | 4-C$_2$H$_5$ |
| 86 | 2,4-(C$_2$H$_5$)$_2$ |
| 87 | 2,6-(C$_2$H$_5$)$_2$ |
| 88 | 3,5-(C$_2$H$_5$)$_2$ |
| 89 | 2,4,6-(C$_2$H$_5$)$_3$ |
| 90 | 2-n-C$_3$H$_7$ |
| 91 | 3-n-C$_3$H$_7$ |
| 92 | 4-n-C$_3$H$_7$ |
| 93 | 2-i-C$_3$H$_7$ |
| 94 | 3-i-C$_3$H$_7$ |
| 95 | 4-i-C$_3$H$_7$ |
| 96 | 2,4-(i-C$_3$H$_7$)$_2$ |
| 97 | 2,6-(i-C$_3$H$_7$)$_2$ |
| 98 | 3,5-(i-C$_3$H$_7$)$_2$ |
| 99 | 2,4,6-(i-C$_3$H$_7$)$_3$ |
| 100 | 2-s-C$_4$H$_9$ |
| 101 | 3-s-C$_4$H$_9$ |
| 102 | 4-s-C$_4$H$_9$ |
| 103 | 2-t-C$_4$H$_9$ |
| 104 | 3-t-C$_4$H$_9$ |
| 105 | 4-t-C$_4$H$_9$ |
| 106 | 2,3-(t-C$_4$H$_9$)$_2$ |
| 107 | 2,4-(t-C$_4$H$_9$)$_2$ |
| 108 | 2,5-(t-C$_4$H$_9$)$_2$ |
| 109 | 2,6-(t-C$_4$H$_9$)$_2$ |
| 110 | 3,4-(t-C$_4$H$_9$)$_2$ |
| 111 | 2,4,6-(t-C$_4$H$_9$)$_3$ |
| 112 | 4-n-C$_9$H$_{19}$ |
| 113 | 4-n-C$_{12}$H$_{25}$ |
| 114 | 4-n-C$_{15}$H$_{31}$ |
| 115 | 4-(1,1,3,3,-Tetramethylbutyl) |
| 116 | 4-(2,4,4-Trimethylpropyl) |
| 117 | 2-t-C$_4$H$_9$, 4-CH$_3$ |
| 118 | 2-t-C$_4$H$_9$, 5-CH$_3$ |
| 119 | 2,6-(t-C$_4$H$_9$)$_2$, 4-CH$_3$ |
| 120 | 2-CH$_3$, 4-t-C$_4$H$_9$ |
| 121 | 2-CH$_3$, 6-t-C$_4$H$_9$ |
| 122 | 2-CH$_3$, 4-i-C$_3$H$_7$ |
| 123 | 2-CH$_3$, 5-i-C$_3$H$_7$ |
| 124 | 3-CH$_3$, 4-i-C$_3$H$_7$ |
| 125 | 2-i-C$_3$H$_7$, 5-CH$_3$ |
| 126 | 2,4-(t-C$_4$H$_9$)$_2$, 6-i-C$_3$H$_7$ |
| 127 | 2-Allyl |
| 128 | 3-Allyl |
| 129 | 4-Allyl |
| 30 | 2-Allyl, 6-CH$_3$ |
| 131 | 2-cyclo-C$_6$H$_{11}$ |
| 132 | 3-cyclo-C$_6$H$_{11}$ |
| 133 | 4-cyclo-C$_6$H$_{11}$ |
| 134 | 2,4-(cyclo-C$_6$H$_{11}$)$_2$, 6-CH$_3$ |
| 135 | 2-CH$_3$, 4-cyclo-C$_6$H$_{11}$ |
| 136 | 2-CH$_2$—C$_6$H$_5$ |
| 137 | 3-CH$_2$—C$_6$H$_5$ |
| 138 | 4-CH$_2$—C$_6$H$_5$ |

TABLE 5-continued

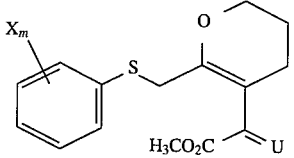

I: U: =CH—OCH$_3$
II: U: =N—OCH$_3$
III: U: =CH—CH$_3$

| No. | X$_m$ |
|---|---|
| 139 | 2-CH$_2$—C$_6$H$_5$, 4-CH$_3$ |
| 140 | 2-CH$_3$, 4-CH$_2$—C$_6$H$_5$ |
| 141 | 2-C$_6$H$_5$ |
| 142 | 3-C$_6$H$_5$ |
| 143 | 4-C$_6$H$_5$ |
| 144 | 4-(2-i-C$_3$H$_7$—C$_6$H$_4$) |
| 145 | 4-C$_6$H$_5$, 2,6-(CH$_3$)$_2$ |
| 146 | 2-Cl, 4-C$_6$H$_5$ |
| 147 | 2-Br, 4-C$_6$H$_5$ |
| 148 | 2-C$_6$H$_5$, 4-Cl |
| 149 | 2-C$_6$H$_5$, 4-Br |
| 150 | 2-CH$_2$C$_6$H$_5$, 4-Cl |
| 151 | 2-CH$_2$C$_6$H$_5$, 4-Br |
| 152 | 2-Cl, 4-CH$_2$C$_6$H$_5$ |
| 153 | 2-Br, 4-CH$_2$C$_6$H$_5$ |
| 154 | 2-cyclo-C$_6$H$_{11}$, 4-Cl |
| 155 | 2-cyclo-C$_6$H$_{11}$, 4-Br |
| 156 | 2-Cl, 4-cyclo-C$_6$H$_{11}$ |
| 157 | 2-Br, 4-cyclo-C$_6$H$_{11}$ |
| 158 | 2-OCH$_3$ |
| 159 | 3-OCH$_3$ |
| 160 | 4-OCH$_3$ |
| 161 | 2-OC$_2$H$_5$ |
| 162 | 3-O—C$_2$H$_5$ |
| 163 | 4-O—C$_2$H$_5$ |
| 164 | 2-O-n-C$_3$H$_7$ |
| 165 | 3-O-n-C$_3$H$_7$ |
| 166 | 4-O-n-C$_3$H$_7$ |
| 167 | 2-O-i-C$_3$H$_7$ |
| 168 | 3-O-i-C$_3$H$_7$ |
| 169 | 4-O-i-C$_3$H$_7$ |
| 170 | 2-O-n-C$_6$H$_{13}$ |
| 171 | 3-O-n-C$_6$H$_{13}$ |
| 172 | 4-O-n-C$_6$H$_{13}$ |
| 173 | 2-O-n-C$_8$H$_{17}$ |
| 174 | 3-O-n-C$_8$H$_{17}$ |
| 175 | 4-O-n-C$_8$H$_{17}$ |
| 176 | 2-O—CH$_2$C$_6$H$_5$ |
| 177 | 3-O—CH$_2$C$_6$H$_5$ |
| 178 | 4-O—CH$_2$C$_6$H$_5$ |
| 179 | 2-O—(CH$_2$)$_3$C$_6$H$_5$ |
| 180 | 3-O—(CH$_2$)$_3$C$_6$H$_5$ |
| 181 | 4-O—(CH$_2$)$_3$C$_6$H$_5$ |
| 182 | 2,4-(OCH$_3$)$_2$ |
| 183 | 2-CF$_3$ |
| 184 | 3-CF$_3$ |
| 185 | 4-CF$_3$ |
| 186 | 2-OCF$_3$ |
| 187 | 3-OCF$_3$ |
| 188 | 4-OCF$_3$ |
| 189 | 3-OCH$_2$CHF$_2$ |
| 190 | 2-NO$_2$ |
| 191 | 3-NO$_2$ |
| 192 | 4-NO$_2$ |
| 193 | 2-CN |
| 194 | 3-CN |
| 195 | 4-CN |
| 196 | 2-CH$_3$, 3-Cl |
| 197 | 2-CH$_3$, 4-Cl |
| 198 | 2-CH$_3$, 5-Cl |
| 199 | 2-CH$_3$, 6-Cl |
| 200 | 2-CH$_3$, 3-F |
| 201 | 2-CH$_3$, 4-F |
| 202 | 2-CH$_3$, 5-F |
| 203 | 2-CH$_3$, 6-F |
| 204 | 2-CH$_3$, 3-Br |
| 205 | 2-CH$_3$, 4-Br |
| 206 | 2-CH$_3$, 5-Br |
| 207 | 2-CH$_3$, 6-Br |

TABLE 5-continued

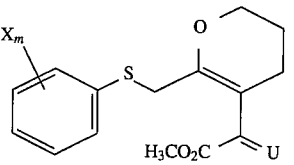

I: U: =CH—OCH$_3$
II: U: =N—OCH$_3$
III: U: =CH—CH$_3$

| No. | X$_m$ |
|---|---|
| 208 | 2-Cl, 3-CH$_3$ |
| 209 | 2-Cl, 4-CH$_3$ |
| 210 | 2-Cl, 5-CH$_3$ |
| 211 | 2-F, 3-CH$_3$ |
| 212 | 2-F, 4-CH$_3$ |
| 213 | 2-F, 5-CH$_3$ |
| 214 | 2-Br, 3-CH$_3$ |
| 215 | 2-Br, 4-CH$_3$ |
| 216 | 2-Br, 5-CH$_3$ |
| 217 | 3-CH$_3$, 4-Cl |
| 218 | 3-CH$_3$, 5-Cl |
| 219 | 3-CH$_3$, 4-F |
| 220 | 3-CH$_3$, 5-F |
| 221 | 3-CH$_3$, 4-Br |
| 222 | 3-CH$_3$, 5-Br |
| 223 | 3-F, 4-CH$_3$ |
| 224 | 3-Cl, 4-CH$_3$ |
| 225 | 3-Br, 4-CH$_3$ |
| 226 | 2-Cl, 4,5-(CH$_3$)$_2$ |
| 227 | 2-Br, 4,5-(CH$_3$)$_2$ |
| 228 | 2-Cl, 3,5-(CH$_3$)$_2$ |
| 229 | 2-Br, 3,5-(CH$_3$)$_2$ |
| 230 | 2,6-Cl$_2$, 4-CH$_3$ |
| 231 | 2,6-F$_2$, 4-CH$_3$ |
| 232 | 2,6-Br$_2$, 4-CH$_3$ |
| 233 | 2,4-Br$_2$, 6-CH$_3$ |
| 234 | 2,4-F$_2$, 6-CH$_3$ |
| 235 | 2,4-Br$_2$, 6-CH$_3$ |
| 236 | 2,6-(CH$_3$)$_2$, 4-F |
| 237 | 2,6-(CH$_3$)$_2$, 4-Cl |
| 238 | 2,6-(CH$_3$)$_2$, 4-Br |
| 239 | 3,5-(CH$_3$)$_2$, 4-F |
| 240 | 3,5-(CH$_3$)$_2$, 4-Cl |
| 241 | 3,5-(CH$_3$)$_2$, 4-Br |
| 242 | 2,3,6-(CH$_3$)$_3$, 4-F |
| 243 | 2,3,6-(CH$_3$)$_3$, 4-Cl |
| 244 | 2,3,6-(CH$_3$)$_3$, 4-Br |
| 245 | 2,4-(CH$_3$)$_2$, 6-F |
| 246 | 2,4-(CH$_3$)$_2$, 6-Cl |
| 247 | 2,4-(CH$_3$)$_2$, 6-Br |
| 248 | 2-i-C$_3$H$_7$, 4-Cl, 5-CH$_3$ |
| 249 | 2-Cl, 4-NO$_2$ |
| 250 | 2-NO$_2$, 4-Cl |
| 251 | 2-OCH$_3$, 5-NO$_2$ |
| 252 | 2,4-Cl$_2$, 5-NO$_2$ |
| 253 | 2,4-Cl$_2$, 6-NO$_2$ |
| 254 | 2,6-Cl$_2$, 4-NO$_2$ |
| 255 | 2,6-Br$_2$, 4-NO$_2$ |
| 256 | 2,6-I$_2$, 4-NO$_2$ |
| 257 | 2-CH$_3$, 5-i-C$_3$H$_7$, 4-Cl |
| 258 | 2-Pyridyl-2 |
| 259 | 3-Pyridyl-2 |
| 260 | 4-Pyridyl-2 |
| 261 | 2-CO$_2$CH$_3$ |
| 262 | 3-CO$_2$CH$_3$ |
| 263 | 4-CO$_2$CH$_3$ |
| 264 | 2-CO$_2$(C$_2$H$_5$) |
| 265 | 3-CO$_2$(C$_2$H$_5$) |
| 266 | 4-CO$_2$(C$_2$H$_5$) |
| 267 | 2-CO$_2$(n-C$_3$H$_7$) |
| 268 | 3-CO$_2$(n-C$_3$H$_7$) |
| 269 | 4-CO$_2$(n-C$_3$H$_7$) |
| 270 | 2-CO$_2$(i-C$_3$H$_7$) |
| 271 | 3-CO$_2$(i-C$_3$H$_7$) |
| 272 | 4-CO$_2$(i-C$_3$H$_7$) |
| 273 | 2-CO$_2$(n-C$_6$H$_{13}$) |
| 274 | 3-CO$_2$(n-C$_6$H$_{13}$) |
| 275 | 4-CO$_2$(n-C$_6$H$_{13}$) |
| 276 | 2-CO$_2$(n-C$_8$H$_{17}$) |

TABLE 5-continued

Structure with $X_m$ substituted phenyl-S-CH$_2$- connected to a dihydropyran ring with O, bearing $H_3CO_2C$ and U groups.

I: U: =CH—OCH$_3$
II: U: =N—OCH$_3$
III: U: =CH—CH$_3$

| No. | $X_m$ |
|---|---|
| 277 | 3-CO$_2$(n-C$_8$H$_{17}$) |
| 278 | 4-CO$_2$(n-C$_8$H$_{17}$) |
| 279 | 2-CH$_2$OCH$_3$ |
| 280 | 3-CH$_2$OCH$_3$ |
| 281 | 4-CH$_2$OCH$_3$ |
| 282 | 2-CH$_2$O(C$_2$H$_5$) |
| 283 | 3-CH$_2$O(C$_2$H$_5$) |
| 284 | 4-CH$_2$O(C$_2$H$_5$) |
| 285 | 2-CH$_2$O(n-C$_3$H$_7$) |
| 286 | 3-CH$_2$O(n-C$_3$H$_7$) |
| 287 | 4-CH$_2$O(n-C$_3$H$_7$) |
| 288 | 2-CH$_2$O(i-C$_3$H$_7$) |
| 289 | 3-CH$_2$O(i-C$_3$H$_7$) |
| 290 | 4-CH$_2$O(i-C$_3$H$_7$) |
| 291 | 2-CH$_2$O(n-C$_6$H$_{13}$) |
| 292 | 3-CH$_2$O(n-C$_6$H$_{13}$) |
| 293 | 4-CH$_2$O(n-C$_6$H$_{13}$) |
| 294 | 2-CH$_2$O(n-C$_8$H$_{17}$) |
| 295 | 3-CH$_2$O(n-C$_8$H$_{17}$) |
| 296 | 4-CH$_2$O(n-C$_8$H$_{17}$) |
| 297 | 2-CH$_2$OCH$_2$(C$_6$H$_5$) |
| 298 | 3-CH$_2$OCH$_2$(C$_6$H$_5$) |
| 299 | 4-CH$_2$OCH$_2$(C$_6$H$_5$) |
| 300 | 2-CH$_2$O(CH$_2$)$_3$(C$_6$H$_5$) |
| 301 | 3-CH$_2$O(CH$_2$)$_3$(C$_6$H$_5$) |
| 302 | 4-CH$_2$O(CH$_2$)$_3$(C$_6$H$_5$) |
| 303 | 2-CHO |
| 304 | 3-CHO |
| 305 | 4-CHO |
| 306 | 2-CO—CH$_3$ |
| 307 | 3-CO—CH$_3$ |
| 308 | 4-CO—CH$_3$ |
| 309 | 2-CO—CH$_2$—CH$_3$ |
| 310 | 3-CO—CH$_2$—CH$_3$ |
| 311 | 4-CO—CH$_2$—CH$_3$ |
| 312 | 2-CO—CH$_2$—CH$_2$—CH$_3$ |
| 313 | 3-CO—CH$_2$—CH$_2$—CH$_3$ |
| 314 | 4-CO—CH$_2$—CH$_2$—CH$_3$ |
| 315 | 2-CO—CH(CH$_3$)—CH$_3$ |
| 316 | 3-CO—CH(CH$_3$)—CH$_3$ |
| 317 | 4-CO—CH(CH$_3$)—CH$_3$ |
| 318 | 2-Me-4-CHO |
| 319 | 2-Me-4-CH$_3$—CO |
| 320 | 2-Me-4-CH$_3$—CH$_2$—CO |
| 321 | 2-Me-4-CH$_3$—CH$_2$—CH$_2$—CO |
| 322 | 2-Me-4-CH$_3$—CH(CH$_3$)—CO |
| 323 | 2,5-Me$_2$-4-CHO |
| 324 | 2,5-Me$_2$-4-CH$_3$—CO |
| 325 | 2,5-Me$_2$-4-CH$_3$—CH$_2$—CO |
| 326 | 2,5-Me$_2$-4-CH$_3$—CH$_2$—CH$_2$—CO |
| 327 | 2,5-Me$_2$-4-CH$_3$—CH(CH$_3$)—CO |
| 328 | 2-Cl-4-CHO |
| 329 | 2-Cl-4-CH$_3$—CO |
| 330 | 2-Cl-4-CH$_3$—CH$_2$—CO |
| 331 | 2-Cl-4-CH$_3$—CH$_2$—CH$_2$—CO |
| 332 | 2-Cl-4-CH$_3$—CH(CH$_3$)—CO |
| 333 | 2,5-Cl$_2$-4-CHO |
| 334 | 2,5-Cl$_2$-4-CH$_3$—CO |
| 335 | 2,5-Cl$_2$-4-CH$_3$—CH$_2$—CO |
| 336 | 2,5-Cl$_2$-4-CH$_3$—CH$_2$—CH$_2$—CO |
| 337 | 2,5-Cl$_2$-4-CH$_3$—CH(CH$_3$)—CO |
| 338 | 2-C(=NOCH$_3$)—CH$_3$ |
| 339 | 3-C(=NOCH$_3$)—CH$_3$ |
| 340 | 4-C(=NOCH$_3$)—CH$_3$ |
| 341 | 2-C(=NOC$_2$H$_5$)—CH$_3$ |
| 342 | 3-C(=NOC$_2$H$_5$)—CH$_3$ |
| 343 | 4-C(=NOC$_2$H$_5$)—CH$_3$ |
| 344 | 2-C(=NO-i-C$_3$H$_7$)—CH$_3$ |
| 345 | 3-C(=NO-i-C$_3$H$_7$)—CH$_3$ |
| 346 | 4-C(=NO-i-C$_3$H$_7$)—CH$_3$ |
| 347 | 2-C(=NO-Allyl)—CH$_3$ |
| 348 | 3-C(=NO-Allyl)—CH$_3$ |
| 349 | 4-C(=NO-Allyl)—CH$_3$ |
| 350 | 2-C(=NO-trans-chloroallyl)—CH$_3$ |
| 351 | 3-C(=NO-trans-chloroallyl)—CH$_3$ |
| 352 | 4-C(=NO-trans-chloroallyl)—CH$_3$ |
| 353 | 2-C(=NO-Propargyl)—CH$_3$ |
| 354 | 3-C(=NO-Propargyl)—CH$_3$ |
| 355 | 4-C(=NO-Propargyl)—CH$_3$ |
| 356 | 2-C(=NO—CH$_2$—C$_6$H$_5$)—CH$_3$ |
| 357 | 3-C(=NO—CH$_2$—C$_6$H$_5$)—CH$_3$ |
| 358 | 4-C(=NO—CH$_2$—C$_6$H$_5$)—CH$_3$ |
| 359 | 2-C(=NOCH$_3$)—C$_2$H$_5$ |
| 360 | 3-C(=NOCH$_3$)—C$_2$H$_5$ |
| 361 | 4-C(=NOCH$_3$)—C$_2$H$_5$ |
| 362 | 2-C(=NOC$_2$H$_5$)—C$_2$H$_5$ |
| 363 | 3-C(=NOC$_2$H$_5$)—C$_2$H$_5$ |
| 364 | 4-C(=NOC$_2$H$_5$)—C$_2$H$_5$ |
| 365 | 2-C(=NO-i-C$_3$H$_7$)—C$_2$H$_5$ |
| 366 | 3-C(=NO-i-C$_3$H$_7$)—C$_2$H$_5$ |
| 367 | 4-C(=NO-i-C$_3$H$_7$)—C$_2$H$_5$ |
| 368 | 2-C(=NO-Allyl)—C$_2$H$_5$ |
| 369 | 3-C(=NO-Allyl)—C$_2$H$_5$ |
| 370 | 4-C(=NO-Allyl)—C$_2$H$_5$ |
| 371 | 2-C(=NO-trans-chloroallyl)—C$_2$H$_5$ |
| 372 | 3-C(=NO-trans-chloroallyl)—C$_2$H$_5$ |
| 373 | 4-C(=NO-trans-chloroallyl)—C$_2$H$_5$ |
| 374 | 2-C(=NO-Propargyl)—C$_2$H$_5$ |
| 375 | 3-C(=NO-Propargyl)—C$_2$H$_5$ |
| 376 | 4-C(=NO-Propargyl)—C$_2$H$_5$ |
| 377 | 2-C(=NO—CH$_2$—C$_6$H$_5$)—C$_2$H$_5$ |
| 378 | 3-C(=NO—CH$_2$—C$_6$H$_5$)—C$_2$H$_5$ |
| 379 | 4-C(=NO—CH$_2$—C$_6$H$_5$)—C$_2$H$_5$ |
| 380 | 2-CH$_3$-4-CH=NOCH$_3$ |
| 381 | 2-CH$_3$-4-CH=NOC$_2$H$_5$ |
| 382 | 2-CH$_3$-4-CH=NO-i-C$_3$H$_7$ |
| 383 | 2-CH$_3$-4-CH=NO-Allyl |
| 384 | 2-CH$_3$-4-CH=NO-(trans-chloroallyl) |
| 385 | 2-CH$_3$-4-CH=NO-Propargyl |
| 386 | 2-CH$_3$-4-CH=NO—CH$_2$—C$_6$H$_5$ |
| 387 | 2-CH$_3$-4-(CH$_3$—C=NOCH$_3$) |
| 388 | 2-CH$_3$-4-(CH$_3$—C=NOC$_2$H$_5$) |
| 389 | 2-CH$_3$-4-(CH$_3$—C=NO-i-C$_3$H$_7$) |
| 390 | 2-CH$_3$-4-(CH$_3$—C=NO-Allyl) |
| 391 | 2-CH$_3$-4-(CH$_3$—C=NO-trans-chloroallyl) |
| 392 | 2-CH$_3$-4-(CH$_3$—C=NO-Propargyl) |
| 393 | 2-CH$_3$-4-(CH$_3$—C=NO—CH$_2$—C$_6$H$_5$) |
| 394 | 2-CH$_3$-4-(C$_2$H$_5$—C=NO—CH$_3$) |
| 395 | 2-CH$_3$-4-(C$_2$H$_5$—C=NO—C$_2$H$_5$) |
| 396 | 2-CH$_3$-4-(C$_2$H$_5$—C=NO-i-C$_3$H$_7$) |
| 397 | 2-CH$_3$-4-(C$_2$H$_5$—C=NO-Allyl) |
| 398 | 2-CH$_3$-4-(C$_2$H$_5$—C=NO-trans-chloroallyl) |
| 399 | 2-CH$_3$-4-(C$_2$H$_5$—C=NO-Propargyl) |
| 400 | 2-CH$_3$-4-(C$_2$H$_5$—C=NO—CH$_2$—C$_6$H$_5$) |
| 401 | 2,5-(CH$_3$)$_2$-4-(CH=NOCH$_3$) |
| 402 | 2,5-(CH$_3$)$_2$-4-(CH=NOC$_2$H$_5$) |
| 403 | 2,5-(CH$_3$)$_2$-4-(CH=NO-i-C$_3$H$_7$) |
| 404 | 2,5-(CH$_3$)$_2$-4-(CH=NO-Allyl) |
| 405 | 2,5-(CH$_3$)$_2$-4-(CH=NO-trans-chloroallyl) |
| 406 | 2,5-(CH$_3$)$_2$-4-(CH=NO-Propargyl) |
| 407 | 2,5-(CH$_3$)$_2$-4-(CH=NO—CH$_2$—C$_6$H$_5$) |
| 408 | 2,5-(CH$_3$)$_2$-4-(CH$_3$—C=NOCH$_3$) |
| 409 | 2,5-(CH$_3$)$_2$-4-(CH$_3$—C=NOC$_2$H$_5$) |
| 410 | 2,5-(CH$_3$)$_2$-4-(CH$_3$—C=NO-i-C$_3$H$_7$) |
| 411 | 2,5-(CH$_3$)$_2$-4-(CH$_3$—C=NO-Allyl) |
| 412 | 2,5-(CH$_3$)$_2$-4-(CH$_3$—C=NO-trans-chloroallyl) |
| 413 | 2,5-(CH$_3$)$_2$-4-(CH$_3$—C=NO-Propargyl) |
| 414 | 2,5-(CH$_3$)$_2$-4-(CH$_3$—C=NO—CH$_2$—C$_6$H$_5$) |

TABLE 5-continued

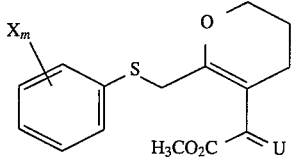

I: U: =CH—OCH$_3$
II: U: =N—OCH$_3$
III: U: =CH—CH$_3$

| No. | X$_m$ |
|---|---|
| 415 | 2,5-(CH$_3$)$_2$-4-(C$_2$H$_5$—C=NOCH$_3$) |
| 416 | 2,5-(CH$_3$)$_2$-4-(C$_2$H$_5$—C=NOC$_2$H$_5$) |
| 417 | 2,5-(CH$_3$)$_2$-4-(C$_2$H$_5$—C=NO-i-C$_3$H$_7$) |
| 418 | 2,5-(CH$_3$)$_2$-4-(C$_2$H$_5$—C=NO-Allyl) |
| 419 | 2,5-(CH$_3$)$_2$-4-(C$_2$H$_5$—C=NO-trans-chloroallyl) |
| 420 | 2,5-(CH$_3$)$_2$-4-(C$_2$H$_5$—C=NO-Propargyl) |
| 421 | 2,5-(CH$_3$)$_2$-4-(C$_2$H$_5$—C=NO—CH$_2$—C$_6$H$_5$) |
| 422 | H |

TABLE 6

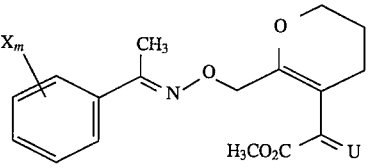

I: U: =CH—OCH$_3$
II: U: =N—OCH$_3$
III: U: =CH—CH$_3$

| No. | X$_m$ |
|---|---|
| 1 | 2-F |
| 2 | 3-F |
| 3 | 4-F |
| 4 | 2,4-F$_2$ |
| 5 | 2,4,6-F$_3$ |
| 6 | 2,3,4,5,6-F$_5$ |
| 7 | 2,3-F$_2$ |
| 8 | 2-Cl |
| 9 | 3-Cl |
| 10 | 4-Cl |
| 11 | 2,3-Cl$_2$ |
| 12 | 2,4-Cl$_2$ |
| 13 | 2,5-Cl$_2$ |
| 14 | 2,6-Cl$_2$ |
| 15 | 3,4-Cl$_2$ |
| 16 | 3,5-Cl2 |
| 17 | 2,3,4-Cl$_3$ |
| 18 | 2,3,5-Cl$_3$ |
| 19 | 2,3,6-Cl$_3$ |
| 20 | 2,4,5-Cl$_3$ |
| 21 | 2,4,6-Cl$_3$ |
| 22 | 3,4,5-Cl$_3$ |
| 23 | 2,3,4,6-Cl$_4$ |
| 24 | 2,3,5,6-Cl$_4$ |
| 25 | 2,3,4,5,6-Cl$_5$ |
| 26 | 2-Br |
| 27 | 3-Br |
| 28 | 4-Br |
| 29 | 2,4-Br$_2$ |
| 30 | 2,5-Br$_2$ |
| 31 | 2,6-Br$_2$ |
| 32 | 2,4,6-Br$_3$ |
| 33 | 2,3,4,5,6-Br$_5$ |
| 34 | 2-I |
| 35 | 3-I |
| 36 | 4-I |
| 37 | 2,4-I$_2$ |
| 38 | 2-Cl, 3-F |
| 39 | 2-Cl, 4-F |
| 40 | 2-Cl, 5-F |
| 41 | 2-Cl, 6-F |
| 42 | 2-Cl, 3-Br |
| 43 | 2-Cl, 4-Br |
| 44 | 2-Cl, 5-Br |
| 45 | 2-Cl, 6-Br |

TABLE 6-continued

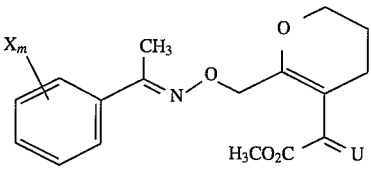

I: U: =CH—OCH$_3$
II: U: =N—OCH$_3$
III: U: =CH—CH$_3$

| No. | X$_m$ |
|---|---|
| 46 | 2-Br, 3-Cl |
| 47 | 2-Br, 4-Cl |
| 48 | 2-Br, 5-Cl |
| 49 | 2-Br, 3-F |
| 50 | 2-Br, 4-F |
| 51 | 2-Br, 5-F |
| 52 | 2-Br, 6-F |
| 53 | 2-F, 3-Cl |
| 54 | 2-F, 4-Cl |
| 55 | 2-F, 5-Cl |
| 56 | 3-Cl, 4-F |
| 57 | 3-Cl, 5-F |
| 58 | 3-Cl, 4-Br |
| 59 | 3-Cl, 5-Br |
| 60 | 3-F, 4-Cl |
| 61 | 3-F, 4-Br |
| 62 | 3-Br, 4-Cl |
| 63 | 3-Br, 4-F |
| 64 | 2,6-Cl$_2$, 4-Br |
| 65 | 2-CH$_3$ |
| 66 | 3-CH$_3$ |
| 67 | 4-CH$_3$ |
| 68 | 2,3-(CH$_3$)$_2$ |
| 69 | 2,4-(CH$_3$)$_2$ |
| 70 | 2,5-(CH$_3$)$_2$ |
| 71 | 2,6-(CH$_3$)$_2$ |
| 72 | 3,4-(CH$_3$)$_2$ |
| 73 | 3,5-(CH$_3$)$_2$ |
| 74 | 2,3,5-(CH$_3$)$_3$ |
| 75 | 2,3,4-(CH$_3$)$_3$ |
| 76 | 2,3,6-(CH$_3$)$_3$ |
| 77 | 2,4,5-(CH$_3$)$_3$ |
| 78 | 2,4,6-(CH$_3$)$_3$ |
| 79 | 3,4,5-(CH$_3$)$_3$ |
| 80 | 2,3,4,6-(CH$_3$)$_4$ |
| 81 | 2,3,5,6-(CH$_3$)$_4$ |
| 82 | 2,3,4,5,6-(CH$_3$)$_5$ |
| 83 | 2-C$_2$H$_5$ |
| 84 | 3-C$_2$H$_5$ |
| 85 | 4-C$_2$H$_5$ |
| 86 | 2,4-(C$_2$H$_5$)$_2$ |
| 87 | 2,6-(C$_2$H$_5$)$_2$ |
| 88 | 3,5-(C$_2$H$_5$)$_2$ |
| 89 | 2,4,6-(C$_2$H$_5$)$_3$ |
| 90 | 2-n-C$_3$H$_7$ |
| 91 | 3-n-C$_3$H$_7$ |
| 92 | 4-n-C$_3$H$_7$ |
| 93 | 2-i-C$_3$H$_7$ |
| 94 | 3-i-C$_3$H$_7$ |
| 95 | 4-i-C$_3$H$_7$ |
| 96 | 2,4-(i-C$_3$H$_7$)$_2$ |
| 97 | 2,6-(i-C$_3$H$_7$)$_2$ |
| 98 | 3,5-(i-C$_3$H$_7$)$_2$ |
| 99 | 2,4,6-(i-C$_3$H$_7$)$_3$ |
| 100 | 2-s-C$_4$H$_9$ |
| 101 | 3-s-C$_4$H$_9$ |
| 102 | 4-s-C$_4$H$_9$ |
| 103 | 2-t-C$_4$H$_9$ |
| 104 | 3-t-C$_4$H$_9$ |
| 105 | 4-t-C$_4$H$_9$ |
| 106 | 2,3-(t-C$_4$H$_9$)$_2$ |
| 107 | 2,4-(t-C$_4$H$_9$)$_2$ |
| 108 | 2,5-(t-C$_4$H$_9$)$_2$ |
| 109 | 2,6-(t-C$_4$H$_9$)$_2$ |
| 110 | 3,4-(t-C$_4$H$_9$)$_2$ |
| 111 | 2,4,6-(t-C$_4$H$_9$)$_3$ |
| 112 | 4-n-C$_9$H$_{19}$ |
| 113 | 4-n-C$_{12}$H$_{25}$ |

TABLE 6-continued

Structure: X_m-phenyl-C(CH₃)=N-O-CH₂-[dihydropyran with H₃CO₂C-C=U substituent]

I: U: =CH—OCH₃
II: U: =N—OCH₃
III: U: =CH—CH₃

| No. | X_m |
|---|---|
| 114 | 4-n-C₁₅H₃₁ |
| 115 | 4-(1,1,3,3-Tetramethylbutyl) |
| 116 | 4-(2,4,4-Trimethylpropyl) |
| 117 | 2-t-C₄H₉, 4-CH₃ |
| 118 | 2-t-C₄H₉, 5-CH₃ |
| 119 | 2,6-(t-C₄H₉)₂, 4-CH₃ |
| 120 | 2-CH₃, 4-t-C₄H₉ |
| 121 | 2-CH₃, 6-t-C₄H₉ |
| 122 | 2-CH₃, 4-i-C₃H₇ |
| 123 | 2-CH₃, 5-i-C₃H₇ |
| 124 | 3-CH₃, 4-i-C₃H₇ |
| 125 | 2-i-C₃H₇, 5-CH₃ |
| 126 | 2,4-(t-C₄H₉)₂, 6-i-C₃H₇ |
| 127 | 2-Allyl |
| 128 | 3-Allyl |
| 129 | 4-Allyl |
| 130 | 2-Allyl, 6-CH₃ |
| 131 | 2-cyclo-C₆H₁₁ |
| 132 | 3-cyclo-C₆H₁₁ |
| 133 | 4-cyclo-C₆H₁₁ |
| 134 | 2,4-(cyclo-C₆H₁₁)₂, 6-CH₃ |
| 135 | 2-CH₃, 4-cyclo-C₆H₁₁ |
| 136 | 2-CH₂—C₆H₅ |
| 137 | 3-CH₂—C₆H₅ |
| 138 | 4-CH₂—C₆H₅ |
| 139 | 2-CH₂—C₆H₅, 4-CH₃ |
| 140 | 2-CH₃, 4-CH₂—C₆H₅ |
| 141 | 2-C₆H₅ |
| 142 | 3-C₆H₅ |
| 143 | 4-C₆H₅ |
| 144 | 4-(2-i-C₃H₇—C₆H₄) |
| 145 | 4-C₆H₅, 2,6-(CH₃)₂ |
| 146 | 2-Cl, 4-C₆H₅ |
| 147 | 2-Br, 4-C₆H₅ |
| 148 | 2-C₆H₅, 4-Cl |
| 149 | 2-C₆H₅, 4-Br |
| 150 | 2-CH₂C₆H₅, 4-Cl |
| 151 | 2-CH₂C₆H₅, 4-Br |
| 152 | 2-Cl, 4-CH₂C₆H₅ |
| 153 | 2-Br, 4-CH₂C₆H₅ |
| 154 | 2-cyclo-C₆H₁₁, 4-Cl |
| 155 | 2-cyclo-C₆H₁₁, 4-Br |
| 156 | 2-Cl, 4-cyclo-C₆H₁₁ |
| 157 | 2-Br, 4-cyclo-C₆H₁₁ |
| 158 | 2-OCH₃ |
| 159 | 3-OCH₃ |
| 160 | 4-OCH₃ |
| 161 | 2-OC₂H₅ |
| 162 | 3-O—C₂H₅ |
| 163 | 4-O—C₂H₅ |
| 164 | 2-O-n-C₃H₇ |
| 165 | 3-O-n-C₃H₇ |
| 166 | 4-O-n-C₃H₇ |
| 167 | 2-O-i-C₃H₇ |
| 168 | 3-O-i-C₃H₇ |
| 169 | 4-O-i-C₃H₇ |
| 170 | 2-O-n-C₆H₁₃ |
| 171 | 3-O-n-C₆H₁₃ |
| 172 | 4-O-n-C₆H₁₃ |
| 173 | 2-O-n-C₈H₁₇ |
| 174 | 3-O-n-C₈H₁₇ |
| 175 | 4-O-n-C₈H₁₇ |
| 176 | 2-O—CH₂C₆H₅ |
| 177 | 3-O—CH₂C₆H₅ |
| 178 | 4-O—CH₂C₆H₅ |
| 179 | 2-O—(CH₂)₃C₆H₅ |
| 180 | 3-O—(CH₂)₃C₆H₅ |
| 181 | 4-O—(CH₂)₃C₆H₅ |
| 182 | 2,4-(OCH₃)₂ |
| 183 | 2-CF₃ |
| 184 | 3-CF₃ |
| 185 | 4-CF₃ |
| 186 | 2-OCF₃ |
| 187 | 3-OCF₃ |
| 188 | 4-OCF₃ |
| 189 | 3-OCH₂CHF₂ |
| 190 | 2-NO₂ |
| 191 | 3-NO₂ |
| 192 | 4-NO₂ |
| 193 | 2-CN |
| 194 | 3-CN |
| 195 | 4-CN |
| 196 | 2-CH₃, 3-Cl |
| 197 | 2-CH₃, 4-Cl |
| 198 | 2-CH₃, 5-Cl |
| 199 | 2-CH₃, 6-Cl |
| 200 | 2-CH₃, 3-F |
| 201 | 2-CH₃, 4-F |
| 202 | 2-CH₃, 5-F |
| 203 | 2-CH₃, 6-F |
| 204 | 2-CH₃, 3-Br |
| 205 | 2-CH₃, 4-Br |
| 206 | 2-CH₃, 5-Br |
| 207 | 2-CH₃, 6-Br |
| 208 | 2-Cl, 3-CH₃ |
| 209 | 2-Cl, 4-CH₃ |
| 210 | 2-Cl, 5-CH₃ |
| 211 | 2-F, 3-CH₃ |
| 212 | 2-F, 4-CH₃ |
| 213 | 2-F, 5-CH₃ |
| 214 | 2-Br, 3-CH₃ |
| 215 | 2-Br, 4-CH₃ |
| 216 | 2-Br, 5-CH₃ |
| 217 | 3-CH₃, 4-Cl |
| 218 | 3-CH₃, 5-Cl |
| 219 | 3-CH₃, 4-F |
| 220 | 3-CH₃, 4-Br |
| 221 | 3-CH₃, 5-F |
| 222 | 3-CH₃, 5-Br |
| 223 | 3-F, 4-CH₃ |
| 224 | 3-Cl, 4-CH₃ |
| 225 | 3-Br, 4-CH₃ |
| 226 | 2-Cl, 4,5-(CH₃)₂ |
| 227 | 2-Br, 4,5-(CH₃)₂ |
| 228 | 2-Cl, 3,5-(CH₃)₂ |
| 229 | 2-Br, 3,5-(CH₃)₂ |
| 230 | 2,6-Cl₂, 4-CH₃ |
| 231 | 2,6-F₂, 4-CH₃ |
| 232 | 2,6-Br₂, 4-CH₃ |
| 233 | 2,4-Br₂, 6-CH₃ |
| 234 | 2,4-F₂, 6-CH₃ |
| 235 | 2,4-Br₂, 6-CH₃ |
| 236 | 2,6-(CH₃)₂, 4-F |
| 237 | 2,6-(CH₃)₂, 4-Cl |
| 238 | 2,6-(CH₃)₂, 4-Br |
| 239 | 3,5-(CH₃)₂, 4-F |
| 240 | 3,5-(CH₃)₂, 4-Cl |
| 241 | 3,5-(CH₃)₂, 4-Br |
| 242 | 2,3,6-(CH₃)₃, 4-F |
| 243 | 2,3,6-(CH₃)₃, 4-Cl |
| 244 | 2,3,6-(CH₃)₃, 4-Br |
| 245 | 2,4-(CH₃)₂, 6-F |
| 246 | 2,4-(CH₃)₂, 6-Cl |
| 247 | 2,4-(CH₃)₂, 6-Br |
| 248 | 2-i-C₃H₇, 4-Cl, 5-CH₃ |
| 249 | 2-Cl, 4-NO₂ |

TABLE 6-continued

I: U: =CH—OCH₃
II: U: =N—OCH₃
III: U: =CH—CH₃

| No. | $X_m$ |
|---|---|
| 250 | 2-NO₂, 4-Cl |
| 251 | 2-OCH₃, 5-NO₂ |
| 252 | 2,4-Cl₂, 5-NO₂ |
| 253 | 2,4-Cl₂, 6-NO₂ |
| 254 | 2,6-Cl₂, 4-NO₂ |
| 255 | 2,6-Br₂, 4-NO₂ |
| 256 | 2,6-I₂, 4-NO₂ |
| 257 | 2-CH₃, 5-i-C₃H₇, 4-Cl |
| 258 | 2-Pyridyl-2 |
| 259 | 3-Pyridyl-2 |
| 260 | 4-Pyridyl-2 |
| 261 | 2-CO₂CH₃ |
| 262 | 3-CO₂CH₃ |
| 263 | 4-CO₂CH₃ |
| 264 | 2-CO₂(C₂H₅) |
| 265 | 3-CO₂(C₂H₅) |
| 266 | 4-CO₂(C₂H₅) |
| 267 | 2-CO₂(n-C₃H₇) |
| 268 | 3-CO₂(n-C₃H₇) |
| 269 | 4-CO₂(n-C₃H₇) |
| 270 | 2-CO₂(i-C₃H₇) |
| 271 | 3-CO₂(i-C₃H₇) |
| 272 | 4-CO₂(i-C₃H₇) |
| 273 | 2-CO₂(n-C₆H₁₃) |
| 274 | 3-CO₂(n-C₆H₁₃) |
| 275 | 4-CO₂(n-C₆H₁₃) |
| 276 | 2-CO₂(n-C₈H₁₇) |
| 277 | 3-CO₂(n-C₈H₁₇) |
| 278 | 4-CO₂(n-C₈H₁₇) |
| 279 | 2-CH₂OCH₃ |
| 280 | 3-CH₂OCH₃ |
| 281 | 4-CH₂OCH₃ |
| 282 | 2-CH₂O(C₂H₅) |
| 283 | 3-CH₂O(C₂H₅) |
| 284 | 4-CH₂O(C₂H₅) |
| 285 | 2-CH₂O(n-C₃H₇) |
| 286 | 3-CH₂O(n-C₃H₇) |
| 287 | 4-CH₂O(n-C₃H₇) |
| 288 | 2-CH₂O(i-C₃H₇) |
| 289 | 3-CH₂O(i-C₃H₇) |
| 290 | 4-CH₂O(i-C₃H₇) |
| 291 | 2-CH₂O(n-C₆H₁₃) |
| 292 | 3-CH₂O(n-C₆H₁₃) |
| 293 | 4-CH₂O(n-C₆H₁₃) |
| 294 | 2-CH₂O(N—C₈H₁₇) |
| 295 | 3-CH₂O(N—C₈H₁₇) |
| 296 | 4-CH₂O(N—C₈H₁₇) |
| 297 | 2-CH₂OCH₂(C₆H₅) |
| 298 | 3-CH₂OCH₂(C₆H₅) |
| 299 | 4-CH₂OCH₂(C₆H₅) |
| 300 | 2-CH₂O(CH₂)₃(C₆H₅) |
| 301 | 3-CH₂O(CH₂)₃(C₆H₅) |
| 302 | 4-CH₂O(CH₂)₃(C₆H₅) |
| 303 | 2-CHO |
| 304 | 3-CHO |
| 305 | 4-CHO |
| 306 | 2-CO—CH₃ |
| 307 | 3-CO—CH₃ |
| 308 | 4-CO—CH₃ |
| 309 | 2-CO—CH₂—CH₃ |
| 310 | 3-CO—CH₂—CH₃ |
| 311 | 4-CO—CH₂—CH₃ |
| 312 | 2-CO—CH₂CH₂—CH₃ |
| 313 | 3-CO—CH₂CH₂—CH₃ |
| 314 | 4-CO—CH₂CH₂—CH₃ |
| 315 | 2-CO—CH(CH₃)—CH₃ |
| 316 | 3-CO—CH(CH₃)—CH₃ |
| 317 | 4-CO—CH(CH₃)—CH₃ |
| 318 | 2-Me-4-CHO |
| 319 | 2-Me-4-CH₃—CO |
| 320 | 2-Me-4-CH₃—CH₂—CO |
| 321 | 2-Me-4-CH₃—CH₂—CH₂—CO |
| 322 | 2-Me-4-CH₃—CH(CH₃)—CO |
| 323 | 2,5-Me₂-4-CHO |
| 324 | 2,5-Me₂-4-CH₃—CO |
| 325 | 2,5-Me₂-4-CH₃—CH₂—CO |
| 326 | 2,5-Me₂-4-CH₃—CH₂—CH₂—CO |
| 327 | 2,5-Me₂-4-CH₃—CH(CH₃)—CO |
| 328 | 2-Cl-4-CHO |
| 329 | 2-Cl-4-CH₃—CO |
| 330 | 2-Cl-4-CH₃—CH₂—CO |
| 331 | 2-Cl-4-CH₃—CH₂—CH₂—CO |
| 332 | 2-Cl-4-CH₃—CH(CH₃)—CO |
| 333 | 2,5-Cl₂-4-CHO |
| 334 | 2,5-Cl₂-4-CH₃—CO |
| 335 | 2,5-Cl₂-4-CH₃—CH₂—CO |
| 336 | 2,5-Cl₂-4-CH₃—CH₂—CH₂—CO |
| 337 | 2,5-Cl₂-4-CH₃—CH(CH₃)—CO |
| 338 | 2-C(=NOCH₃)—CH₃ |
| 339 | 3-C(=NOCH₃)—CH₃ |
| 340 | 4-C(=NOCH₃)—CH₃ |
| 341 | 2-C(=NOC₂H₅)—CH₃ |
| 342 | 3-C(=NOC₂H₅)—CH₃ |
| 343 | 4-C(=NOC₂H₅)—CH₃ |
| 344 | 2-C(=NO-i-C₃H₇)—CH₃ |
| 345 | 3-C(=NO-i-C₃H₇)—CH₃ |
| 346 | 4-C(=NO-i-C₃H₇)—CH₃ |
| 347 | 2-C(=NO-Allyl)—CH₃ |
| 348 | 3-C(=NO-Allyl)—CH₃ |
| 349 | 4-C(=NO-Allyl)—CH₃ |
| 350 | 2-C(=NO-trans-chloroallyl)—CH₃ |
| 351 | 3-C(=NO-trans-chloroallyl)—CH₃ |
| 352 | 4-C(=NO-trans-chloroallyl)—CH₃ |
| 353 | 2-C(=NO-Propargyl)—CH₃ |
| 354 | 3-C(=NO-Propargyl)—CH₃ |
| 355 | 4-C(=NO-Propargyl)—CH₃ |
| 356 | 2-C(=NO—CH₂—C₆H₅)—CH₃ |
| 357 | 3-C(=NO—CH₂—C₆H₅)—CH₃ |
| 358 | 4-C(=NO—CH₂—C₆H₅)—CH₃ |
| 359 | 2-C(=NOCH₃)—C₂H₅ |
| 360 | 3-C(=NOCH₃)—C₂H₅ |
| 361 | 4-C(=NOCH₃)—C₂H₅ |
| 362 | 2-C(=NOC₂H₅)—C₂H₅ |
| 363 | 3-C(=NOC₂H₅)—C₂H₅ |
| 364 | 4-C(=NOC₂H₅)—C₂H₅ |
| 365 | 2-C(=NO-i-C₃H₇)—C₂H₅ |
| 366 | 3-C(=NO-i-C₃H₇)—C₂H₅ |
| 367 | 4-C(=NO-i-C₃H₇)—C₂H₅ |
| 368 | 2-C(=NO-Allyl)—C₂H₅ |
| 369 | 3-C(=NO-Allyl)—C₂H₅ |
| 370 | 4-C(=NO-Allyl)—C₂H₅ |
| 371 | 2-C(=NO-trans-chloroallyl)—C₂H₅ |
| 372 | 3-C(=NO-trans-chloroallyl)—C₂H₅ |
| 373 | 4-C(=NO-trans-chloroallyl)—C₂H₅ |
| 374 | 2-C(=NO-Propargyl)—C₂H₅ |
| 375 | 3-C(=NO-Propargyl)—C₂H₅ |
| 376 | 4-C(=NO-Propargyl)—C₂H₅ |
| 377 | 2-C(=NO—CH₂—C₆H₅)—C₂H₅ |
| 378 | 3-C(=NO—CH₂—C₆H₅)—C₂H₅ |
| 379 | 4-C(=NO—CH₂—C₆H₅)—C₂H₅ |
| 380 | 2-CH₃-4-CH=NOCH₃ |
| 381 | 2-CH₃-4-CH=NOC₂H₅ |
| 382 | 2-CH₃-4-CH=NO-i-C₃H₇ |
| 383 | 2-CH₃-4-CH=NO-Allyl |
| 384 | 2-CH₃-4-CH=NO-(trans-chloroallyl) |
| 385 | 2-CH₃-4-CH=NO-Propargyl |

TABLE 6-continued

Structure: Ar(X_m)-C(CH₃)=N-O-CH₂-[dihydropyran ring]-C(CO₂CH₃)=U

I: U: =CH—OCH₃
II: U: =N—OCH₃
III: U: =CH—CH₃

| No. | X_m |
|---|---|
| 386 | 2-CH₃-4-CH=NO—CH₂—C₆H₅ |
| 387 | 2-CH₃-4-(CH₃—C=NOCH₃) |
| 388 | 2-CH₃-4-(CH₃—C=NOC₂H₅) |
| 389 | 2-CH₃-4-(CH₃—C=NO-i-C₃H₇) |
| 390 | 2-CH₃-4-(CH₃—C=NO-Allyl) |
| 391 | 2-CH₃-4-(CH₃—C=NO-trans-chloroallyl) |
| 392 | 2-CH₃-4-(CH₃—C=NO-Propargyl) |
| 393 | 2-CH₃-4-(CH₃—C=NO—CH₂—C₆H₅) |
| 394 | 2-CH₃-4-(C₂H₅—C=NO—CH₃) |
| 395 | 2-CH₃-4-(C₂H₅—C=NO—C₂H₅) |
| 396 | 2-CH₃-4-(C₂H₅—C=NO-i-C₃H₇) |
| 397 | 2-CH₃-4-(C₂H₅—C=NO-Allyl) |
| 398 | 2-CH₃-4-(C₂H₅—C=NO-trans-chloroallyl) |
| 399 | 2-CH₃-4-(C₂H₅—C=NO-Propargyl) |
| 400 | 2-CH₃-4-(C₂H₅—C=NO—CH₂—C₆H₅) |
| 401 | 2,5-(CH₃)₂-4-(CH=NOCH₃) |
| 402 | 2,5-(CH₃)₂-4-(CH=NOC₂H₅) |
| 403 | 2,5-(CH₃)₂-4-(CH=NO-i-C₃H₇) |
| 404 | 2,5-(CH₃)₂-4-(CH=NO-Allyl) |
| 405 | 2,5-(CH₃)₂-4-(CH=NO-trans-chloroallyl) |
| 406 | 2,5-(CH₃)₂-4-(CH=NO-Propargyl) |
| 407 | 2,5-(CH₃)₂-4-(CH=NO—CH₂—C₆H₅) |
| 408 | 2,5-(CH₃)₂-4-(CH₃—C=NOCH₃) |
| 409 | 2,5-(CH₃)₂-4-(CH₃—C=NOC₂H₅) |
| 410 | 2,5-(CH₃)₂-4-(CH₃—C=NO-i-C₃H₇) |
| 411 | 2,5-(CH₃)₂-4-(CH₃—C=NO-Allyl) |
| 412 | 2,5-(CH₃)₂-4-(CH₃—C=NO-trans-chloroallyl) |
| 413 | 2,5-(CH₃)₂-4-(CH₃—C=NO-Propargyl) |
| 414 | 2,5-(CH₃)₂-4-(CH₃—C=NO—CH₂—C₆H₅) |
| 415 | 2,5-(CH₃)₂-4-(C₂H₅—C=NOCH₃) |
| 416 | 2,5-(CH₃)₂-4-(C₂H₅—C=NOC₂H₅) |
| 417 | 2,5-(CH₃)₂-4-(C₂H₅—C=NO-i-C₃H₇) |
| 418 | 2,5-(CH₃)₂-4-(C₂H₅—C=NO-Allyl) |
| 419 | 2,5-(CH₃)₂-4-(C₂H₅—C=NO-trans-chloroallyl) |
| 420 | 2,5-(CH₃)₂-4-(C₂H₅—C=NO-Propargyl) |
| 421 | 2,5-(CH₃)₂-4-(C₂H₅—C=NO—CH₂—C₆H₅) |
| 422 | H |

TABLE 7

Selected physical data of some compounds
a) Non-polar isomer b) Polar isomer

| No. | Compound | m.p./°C. | NMR/ppm |
|---|---|---|---|
| 1 | Table 1, No. I/1 | a) 98° C.<br>b) 102° C. | |
| 2 | Table 4, No. I/422 | a) 84° C.<br>b) — | 5.45(s, 1H); 3.65(s, 3H); 3.6(s, 3H) |
| 3 | Table 1, No. I/128 | a) —<br>b) — | 7.45(s, 1H); 3.85(s, 3H); 3.7(s, 3H)<br>6.5(s, 1H), 3.85(s, 3H); 3.75(s, 3H) |
| 4 | Table 4, No. I/65 | a) —<br>b) — | 7.3(s, 1H); 3.8(s, 3H); 3.65(s, 3H)<br>5.7(s, 1H); 3.65(s, 3H); 3.6(s, 3H) |

TABLE 7-continued

Selected physical data of some compounds
a) Non-polar isomer b) Polar isomer

| No. | Compound | m.p./°C. | NMR/ppm |
|---|---|---|---|
| 5 | [structure: 4-Cl-phenyl-C(=N-O-)-CH=C-CH=CH- pyran with H₃CO₂C/OCH₃ group] Table 2, No. I/396 | a) 171° b) 182° | |
| 6 | [structure: 1-methylcyclopropane-C(=O)-O-CH₂- pyran with H₃CO₂C/OCH₃ group] | a) — b) — | 7.35(s, 2H); 3.8(s, 3H); 3.7(s, 3H) 6.5(s, 1H); 3.85(s, 3H); 3.7(s, 3H) |
| 7 | [structure: 2,5-dimethylphenyl-CH=CH- pyran with H₃CO₂C/OCH₃ group] Table 1, No. I/133 | — | 7.45(s, 1H); 3.85(s, 3H); 3.75(s, 3H) |
| 8 | [structure: 2-methylphenyl-S-CH₂- pyran with H₃CO₂C/OCH₃ group] Table 5, No. I/65 | — | 7.3(s, 1H); 3.8(s, 3H); 3.7(s, 3H) |
| 9 | [structure: phenyl-CH=CH-CH=CH- pyran with H₃CO₂C/OCH₃ group] | a) — b) — | 7.4(s, 1H); 3.8(s, 3H); 3.7(s, 3H) 6.5(s, 1H); 3.9(s, 3H); 3.7(s, 3H) |
| 10 | [structure: 4-methylphenyl-CH=CH- pyran with H₃CO₂C/OCH₃ group] Table 1, No. I/130 | a) 120° C. b) 107° C. | |
| 11 | [structure: 3-methylphenyl-CH=CH- pyran with H₃CO₂C/OCH₃ group] Table 1, No. I/129 | a) — b) — | 7.45(s, 1H); 3.85(s, 3H); 3.75(s, 3H) 6.5(s, 1H); 3.9(s, 3H); 3.75(s, 3H) |
| 12 | [structure: 2-chlorophenyl-CH=CH- pyran with H₃CO₂C/OCH₃ group] Table 1, No. I/8 | a) — b) — | 7.45(s, 1H); 3.85(s, 3H); 3.75(s, 3H) 6.5(s, 1H); 3.9(s, 3H); 3.75(s, 3H) |

TABLE 7-continued

Selected physical data of some compounds
a) Non-polar isomer b) Polar isomer

| No. | Compound | m.p./°C | NMR/ppm |
|---|---|---|---|
| 13 | (3-Cl-C6H4)-CH=CH-[dihydropyran]-C(CO2CH3)=CH-OCH3 Table 1, No. I/9 | a) —<br>b) — | 7.45(s, 1H); 3.85(s, 3H); 3.75(s, 3H)<br>6.5(s, 1H); 3.9(s, 3H); 3.75(s, 3H) |
| 14 | (4-Cl-C6H4)-CH=CH-[dihydropyran]-C(CO2CH3)=CH-OCH3 Table 1, No. I/10 | a) 144° C.<br>b) 144° C. | |
| 15 | (2,4-diMe-C6H3)-CH=CH-[dihydropyran]-C(CO2CH3)=CH-OCH3 Table 9, No. I/132 | a) —<br>b) 86° C. | 7.4(s, 1H); 3.8(s, 3H); 3.7(s, 3H); |
| 16 | (2,3-diMe-C6H3)-CH=CH-[dihydropyran]-C(CO2CH3)=CH-OCH3 Table 1, No. I/131 | a) 110° C.<br>b) 95° C. | |
| 17 | (2,6-diMe-C6H3)-CH=CH-[dihydropyran]-C(CO2CH3)=CH-OCH3 Table 1, No. I/134 | a) 142° C.<br>b) 95° C. | |
| 18 | (3,4-diMe-C6H3)-CH=CH-[dihydropyran]-C(CO2CH3)=CH-OCH3 Table 1, No. I/135 | a) 116° C.<br>b) — | 6.5(s, 1H); 3.85(s, 3H); 3.75(s, 3H) |
| 19 | (C6H5)-CH=CH-[dihydropyran]-C(CO2CH3)=N-OCH3 Table 1, No. II/1 | a) 77° C.<br>b) 108° C. | |

TABLE 7-continued

Selected physical data of some compounds
a) Non-polar isomer b) Polar isomer

| No. | Compound | m.p./°C. | NMR/ppm |
|---|---|---|---|
| 20 | Table 4, No. II/422 | a) —<br>b) — | 3.9(s, 3H); 3.8(s, 3H)<br>4.0(s, 3H); 3.8(s, 3H) |
| 21 | Table 1, No. II/138 | a) —<br>b) — | 3.95(s, 3H); 3.85(s, 3H)<br>4.05(s, 3H); 3.85(s, 3H) |
| 22 | Table 4, No. II/65 | a) 45° C.<br>b) — | 4.0(s, 3H); 3.8(s, 3H) |
| 23 | Table 3, No. II/422 | a) —<br>b) — | 3.75(s, 3H); 3.85(s, 3H)<br>4.0(s, 3H); 3.8(s, 3H) |
| 24 | Table 3, No. II/65 | a) —<br>b) — | 3.85(s, 3H); 3.7(s, 3H)<br>3.95(s, 3H); 3.75(s, 3H) |
| 25 | | a) —<br>b) — | 3.8(s, 3H); 3.7(s, 3H)<br>3.95(s, 3H); 3.8(s, 3H) |
| 26 | Table 6, No. II/28 | a) 88° C.<br>b) — | 4.09(s, 3H); 3.8(s, 3H) |
| 27 | | a) 61° C.<br>b) 105° C. | |

TABLE 7-continued

Selected physical data of some compounds
a) Non-polar isomer b) Polar isomer

| No. | Compound | m.p./°C. | NMR/ppm |
|---|---|---|---|
| 28 | (structure with phenyl-CH=CH-dihydropyran, H₃CO₂C, N~OCH₃) | a) — b) — | 3.9(s, 3H); 3.8(s, 3H); 4.0(s, 3H); 3.8(s, 3H) |
| 29 | (3-methylphenyl analog) Table 1, No. II/129 | a) — b) — | 3.95(s, 3H); 3.85(s, 3H) 4.05(s, 3H); 3.85(s, 3H) |
| 30 | (4-methylphenyl analog) Table 1, No. II/130 | 99° C. | |
| 31 | (2-chlorophenyl analog) Table 1, No. II/8 | a) 64° C. b) — | 4.05(s, 3H); 3.85(s, 3H) |
| 32 | (3-chlorophenyl analog) Table 1, No. II/9 | a) — b) 80° C. | 3.95(s, 3H); 3.85(s, 3H) |
| 33 | (4-chlorophenyl analog) Table 1, No. II/10 | a) 77° C. b) 180° C. | |
| 34 | (3,4-dimethylphenyl analog) Table 1, No. II/135 | a) — b) 109° C. | 3.9(s, 3H); 3.8(s, 3H) |

TABLE 7-continued

Selected physical data of some compounds
a) Non-polar isomer b) Polar isomer

| No. | Compound | m.p./°C | NMR/ppm |
|---|---|---|---|
| 35 | Table 1, No. II/133 | a) 82° C. <br> b) 76° C. | |
| 36 | Table 1, No. II/132 | a) — <br> b) 82° C. | 3.9(s, 3H); 3.8(s, 3H) |
| 37 | Table 1, No. II/134 | a) 91° C. <br> b) 80° C. | |
| 38 | Table 1, No. II/131 | a) — <br> b) 102° C. | 3.9(s, 3H); 3.8(s, 3H) |
| 39 | Table 1, No. II/ | a) 119° C. <br> b) 133° C. | |
| 40 | Table 1, No. III/1 | | 7.1(q, 1H, I = 8 Hz); 3.75(s, 3H) |
| 41 | Table 1, No. III/128 | 88° C. | |

TABLE 7-continued

Selected physical data of some compounds
a) Non-polar isomer b) Polar isomer

| No. | Compound | m.p./°C. | NMR/ppm |
|---|---|---|---|
| 42 | (2-methylphenyl)-CH=CH-[dihydropyran]-C(CO₂CH₃)=CH-Cl | — | 7.5(s, 1H); 3.75(s, 3H) |
| 43 | (2-methylphenyl)-CH=CH-[dihydropyran]-C(CO₂CH₃)=CH-Br | — | 2 isomers (1:1); 7.75(s, 1H); 6.55 (s, 1H); 6.55(s, 1H); 3.8(s, 3H); 3.7(s, 3H); |
| 44 | (2-methylphenyl)-CH=CH-[dihydropyran]-C(CO₂CH₃)=CH-S-CH₃ | — | 7.7(s, 1H); 3.7(s, 3H); |
| 45 | (2,5-dimethylphenyl)-CH=CH-[dihydropyran]-C(=N-OCH₃)-C(=O)-NH-CH₃ | 140° C. | |
| 46 | (2-methylphenyl)-CH=CH-[dihydropyran]-C(CO₂-t-But)=CH-CH₃ | 90° C. | |
| 47 | (2,5-dimethylphenyl)-CH=CH-[dihydropyran]-C(=N-OCH₃)-C(=O)-NH-CH₃ | 168° C. | |
| 48 | (2,5-dimethylphenyl)-CH₂-[dihydropyran with CH₃]-C(CO₂CH₃)=N-OCH₃ | 105° C. | |

The novel compounds are suitable as fungicides, insecticides, nematicides and for regulating plant growth.

The novel compounds I, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients, or the seeds of the plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as ligninsulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of formulations are as follows:

I. A solution of 90 parts by weight of compound no. I/1a from Table 1 and 10 parts by weight of N-methyl-α-pyrrolidone, which is suitable for application in the form of very fine drops.

II. A mixture of 20 parts by weight of compound no. I/396b from Table 2, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By finely distributing the solution in water, an aqueous dispersion is obtained.

III. An aqueous dispersion of 20 parts by weight of compound no. 6a from Table 7, 40 parts by weight of cyclohexanone, 30 parts by weight of isobutanol, and 20 parts by weight of the adduct of 40 moles of ethylene oxide and 1 mole of castor oil.

IV. An aqueous dispersion of 20 parts by weight of compound no. I/133 from Table 1, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A mixture, triturated in a hammer mill, of 80 parts by weight of compound no. 9b from Table 7, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel; by uniformly distributing the mixture in water, a spray liquor is obtained.

VI. An intimate mixture of 3 parts by weight of compound no. I/130a from Table 1 is intimately mixed with 97 parts by weight of particulate kaolin; this dust contains 3% by weight of the active ingredient.

VII. An intimate mixture of 30 parts by weight of compound no. I/129b from Table 1, is intimately mixed with a mixture consisting of 92 parts by weight of powdered silica gel and 8 parts by weight of paraffin oil which has been sprayed onto the surface of this silica gel; this formulation of the active ingredient is obtained has good adherence.

VIII. A stable aqueous dispersion of 40 parts by weight of compound no. I/8a from Table 1, 10 parts by weight of the sodium salt of a phenolsulfonic acid-urea-formaldehyde condensate, 2 parts by weight of silica gel and 48 parts by weight of water, which can be further diluted.

IX. A stable, oily dispersion of 20 parts by weight of compound no. I/8b from Table 1, 2 parts by weight of the calcium salt of dodecylbenzenesulfonic acid, 8 parts by weight of a fatty alcohol polyglycol ether, 20 parts by weight of the sodium salt of a phenolsulfonic acid-urea-formaldehyde condensate, and 68 parts by weight of a paraffinic mineral oil.

The novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits, and the seeds of these plants.

The compounds are applied by treating the fungi, the seeds, plants or materials to be protected against fungus attack, or the soil with a fungicidally effective amount of the active ingredients.

Application may be effected before or after infection of the materials, plants or seed by the fungi.

The compounds I are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The novel compounds may also be used for protecting materials (timber), e.g., on *Paecilomyces variotii*.

The fungicidal agents generally contain from 0.1 to 95, and preferably from 0.5 to 90, wt % of active ingredient.

The application rates depend on the type of effect desired, and range from 0.02 to 3 kg of active ingredient per hectare.

When the active ingredients are used for treating seed, application rates of from 0.001 to 50, and preferably from 0.01 to 10, g are generally required per kg of seed.

When the active ingredients according to the invention are used as fungicides, they may be mixed and applied together with other active ingredients, for example herbicides, insecticides, growth regulators, other fungicides and fertilizers. When the compounds according to the invention are admixed with other fungicides, the spectrum of fungicidal action is in many instances increased.

The following list of fungicides with which the novel compounds may be combined is intended to illustrate possible combinations but not to impose any restrictions. Examples of fungicides which may be combined with the novel compounds are:

sulfur,
dithiocarbamates and their derivatives, such as ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and N,N'-polypropylenebis (thiocarbamyl) disulfide;
nitro derivative, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-—bis-(dimethylamino)-phosphinyl'-3-phenyl-1,2,4-triazole,
2,3-dicyano-1,4-dithioanthraquinone,
2-thio-1,3-dithio-4,5-b'quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N[3-(p-tert.-butylphenyl)-2-methylpropyl]-cis-2,6-dimethylmorpholine,
N-3-(p-tert.-butylphenyl)-2-methylpropyl]-piperidine,
1-2-(2,4-dichlorophenyl)-4-ethyl-1,3-dioxolan-2-yl-ethyl]-1H-1,2,4-triazole,
1-[2-(2,4-dichlorophenyl)-4-n-propyl-1,3-dioxolan-2-yl-ethyl]-1H-1,2,4-triazole,
N-(n-propyl)-N-(2,4,6-trichlorophenoxyethyl)-N]-imidazolylurea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3, 5-dimethyl-2-oxycyclohexyl)-2-hydroxyethyl]-glutaramide,
hexachlorobenzene,
DL-methyl-N-(2,6-dimethylphehyl)-N-fur-2-yl alanate,
methyl DL-N-(2,6-dimethylphenyl)-N-(2]-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine, 3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-a-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

For comparison purposes, 3,4-dihydro-6-methyl-2H-pyran-5-carboxanilide (A) known from page 902 of the 8th edition of Pesticide Manual was employed.

USE EXAMPLE 1

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients nos. 1a, 5b, 6a, 7, 9b, 10a, 11b, 12a, 12b, 13a, 13b, 14a, 14b, 15a, 17a, 17b, 18a, 27a, 27b, 28a, 29b, 30, 31a, 31b, 32a, 32b, 34a, 35a, 35b, 36a, 37a, 37b, 39a, 39b and 42 from Table 7, when applied as aqueous spray liquors containing 250 ppm of active ingredient, had a better fungicidal action (95%) than prior art comparative active ingredient A (55%).

USE EXAMPLE 2

Action on *Pyricularia oryzae*

Leaves of pot-grown rice seedlings of the "Bahia" variety were sprayed to runoff with aqueous emulsions containing (dry basis) 80% of active ingredient and 20% of emulsifier, and inoculated 24 hours later with an aqueous spore suspension of *Pyricularia oryzae*. The plants were then set up in climatic cabinets at 22° to 24° C. and 95 to 99% relative humidity. The extent of fungus attack was assessed after 6 days.

The results show that active ingredients nos. 3a, 6a, 7, 12a, 12b, 13a, 14b, 15a, 15b, 16b, 17a, 17b, 18a, 21, 25b, 31a, 31b, 32a, 34a, 34b, 35a, 35b, 36a, 36b, 37a, 37b, 42, 43 and 44, when applied as aqueous spray liquors containing 250 ppm of active ingredient, have a better fungicidal action (95%) than prior art comparative active ingredient A (55%).

We claim:
1. A dihydropyran of the formula (I):

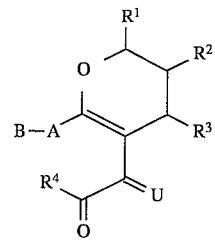

wherein:
$R^1$ is hydrogen;
$R^2$ is hydrogen;
$R^3$ is hydrogen
$R^4$ is $OCH_3$, $OCH_2CH_3$, $NHCH_3$, $NHCH_2CH_3$, $N(CH_3)_2$, $N(CH_2CH_3)_2$, $CH_3$, or $CH_2CH_3$;
U is $CHOR^5$, $CHSR^5$, $CH_2$, $CHR^5$, CH—halogen, or N—$OR^5$,
wherein $R^5$ is methyl or ethyl;
A is a single bond $CHR^6$, $(CHR^7—CHR^6)_n$, $(CR^{21}=CR^{20})_m—CR^7=CR^6$, C≡C, $OCHR^6$, S—$CHR^6$, $NCH_3—CHR^6$, $N(CH_2CH_3)—CHR^6$, CO—$OCHR^6$, CH=N—O—$CHR^6$, $C(CH_3)=N—O—CHR^6$, or $C(CH_2CH_3)=N—O—CHR^6$
wherein:
$R^6$ is hydrogen, $CH_3$, or $CH_2CH_3$;
$R^7$ is hydrogen, $CH_3$, or $CH_2CH_3$;
$R^{20}$ is hydrogen, $CH_3$, or $CH_2CH_3$;
$R^{21}$ is hydrogen, $CH_3$, or $CH_2CH_3$;
n is 1, 2, or 3; and
m is 0 or 1;
B is a $C_3$-$C_{10}$-cycloalkyl, $C_5$-$C_{14}$ cycloalkenyl, phenyl, naphthyl, anthracenyl, furyl, thienyl, pyrryl, isoxazolyl, isothiazolyl, pyrazolyl, oxazolyl, thiazolyl, imidazolyl, 1,2,3-thiadiazolyl, 1,2,4-thiadiazolyl, 1,3,4-thiadiazolyl, tetrazolyl, 1,2,3,4-thiatriazolyl, 1,2,3,4-oxatriazolyl, pyridyl, pyridazinyl, pyrimidinyl, pyrazinyl, 1,2,4-triazinyl, 1,3,5-triazinyl or 1,2,4,5-tetrazinyl group, or where these groups may be substituted with from one to four of the following radicals: halogen, cyano, nitro, $C_1$-$C_4$-haloalkyl, $R^{23}$, $OR^{23}$, =$NOR^{23}$, $COOR^{23}$, $CONR^{12}R^{13}$, $SR^{23}$, $NR^{23}R^{12}$, $COR^{23}$, $SOR^{23}$, $SO_2R^{23}$ or O—$SOR^{23}$, wherein $R^{12}$ is methyl or ethyl; $R^{13}$ is methyl or ethyl; and $R^{23}$ is a $C_1$-$C_{10}$-alkyl, $C_2$-$C_{10}$-alkenyl, $C_2$-$C_{10}$-alkynyl, $C_3$-$C_{10}$-cycloalkyl, $C_5$-$C_{14}$ cycloalkenyl, furyl, thienyl, pyrryl, isoxazolyl, isothiazolyl, pyrazolyl, oxazolyl, thiazolyl, imidazolyl, 1,2,3-thiadiazolyl, 1,2,4-thiadiazolyl, 1,3,4-thiadiazolyl, tetrazolyl, 1,2,3,4-thiatriazolyl, 1,2,3,4-oxatriazolyl, pyridyl, pyridazinyl, pyrimidinyl, pyrazinyl, 1,2,4-triazinyl, 1,3,5-triazinyl or 1,2,4,5-tetrazinyl group.

2. The dihydropyran of formula (I) of claim 1, wherein A is $(CR^{21}=CR^{20})_m—CR^7=CR^6$, and U is $NOR^5$.

3. The dihydropyran of formula (I) of claim 1, wherein B is a furyl, thienyl, pyrryl, isoxazolyl, isothiazolyl, pyrazolyl, oxazolyl, thiazolyl, imidazolyl, 1,2,3-thiadiazolyl, 1,2,4-thiadiazolyl, 1,3,4-thiadiazolyl, tetrazolyl, 1,2,3,4-thiatriazolyl, 1,2,3,4-oxatriazolyl, pyridyl, pyridazinyl, pyrimidinyl, pyrazinyl, 1,2,4-triazinyl, 1,3,5-triazinyl or 1,2,4,5-tetrazinyl group, where these groups may be substituted with from one to four of the following radicals: halogen, cyano, nitro, $C_1$-$C_4$-haloalkyl, $R^{23}$, $OR^{23}$, =$NOR^{23}$, $COOR^{23}$, $CONR^{12}R^{13}$, $SR^{23}$, $NR^{23}R^{12}$, $COR^{23}$, $SOR^{23}$, $SO_2R^{23}$ or O—$SOR^{23}$.

4. The dihydropyran of formula (I) of claim 1, wherein B is a phenyl, naphthyl or anthracenyl group, where these groups may be substituted with from one to four of the following radicals: halogen, cyano, nitro, $C_1$-$C_4$-haloalkyl, $R^{23}$, $OR^{23}$, $=NOR^{23}$, $COOR^{23}$, $CONR^{12}R^{13}$, $SR^{23}$, $NR^{23}R^{12}$, $COR^{23}$, $SOR^{23}$, $SO_2R^{23}$ or $O-SOR^{23}$.

5. A fungicide, comprising an inert carrier and a fungicidal amount of a dihydropyran of the formula (I):

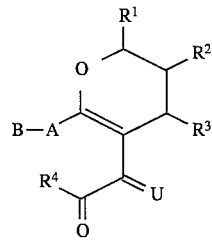

wherein:
$R^1$ is hydrogen;
$R^2$ is hydrogen;
$R^3$ is hydrogen
$R^4$ is $OCH_3$, $OCH_2CH_3$, $NHCH_3$, $NHCH_2CH_3$, $N(CH_3)_2$, $N(CH_2CH_3)_2$, $CH_3$, or $CH_2CH_3$;
U is $CHOR^5$, $CHSR^5$, $CH_2$, $CHR^5$, CH—halogen, or N—$OR^5$,
wherein $R^5$ is methyl or ethyl;
A is a single bond $CHR^6$, $(CHR^7\text{-}CHR^6)_n$, $(CR^{21}=CR^{20})_m$—$CR^7=CR^6$, C≡C, $OCHR^6$, S—$CHR^6$, $NCH_3$-$CHR^6$, $N(CH_2CH_3)$—$CHR^6$, CO—$OCHR^6$, CH=N—O—$CHR^6$, $C(CH_3)=N$—O—$CHR^6$, or $C(CH_2CH_3)=N$—O—$CHR^6$
wherein:
$R^6$ is hydrogen, $CH_3$, or $CH_2CH_3$;
$R^7$ is hydrogen, $CH_3$, or $CH_2CH_3$;
$R^{20}$ is hydrogen, $CH_3$, or $CH_2CH_3$;
$R^{21}$ is hydrogen, $CH_3$, or $CH_2CH_3$;
n is 1, 2, or 3; and
m is 0 or 1;
B is a $C_3$-$C_{10}$-cycloalkyl, $C_5$-$C_{14}$ cycloalkenyl, phenyl, naphthyl, anthracenyl, furyl, thienyl, pyrryl, isoxazolyl, isothiazolyl, pyrazolyl, oxazolyl, thiazolyl, imidazolyl, 1,2,3-thiadiazolyl, 1,2,4-thiadiazolyl, 1,3,4-thiadiazolyl, tetrazolyl, 1,2,3,4-thiatriazolyl, 1,2,3,4-oxatriazolyl, pyridyl, pyridazinyl, pyrimidinyl, pyrazinyl, 1,2,4-triazinyl, 1,3,5-triazinyl or 1,2,4,5-tetrazinyl group, or where these groups may be substituted with from one to four of the following radicals: halogen, cyano, nitro, $C_1$-$C_4$-haloalkyl, $R^{23}$, $OR^{23}$, $=NOR^{23}$, $COOR^{23}$, $CONR^{12}R^{13}$, $SR^{23}$, $NR^{23}R^{12}$, $COR^{23}$, $SOR^{23}$, $SO_2R^{23}$ or $O-SOR^{23}$, wherein $R^{12}$ is methyl or ethyl; $R^{13}$ is methyl or ethyl; and $R^{23}$ is a $C_1$-$C_{10}$-alkyl, $C_2$-$C_{10}$-alkenyl, $C_2$-$C_{10}$-alkynyl, $C_3$-$C_{10}$-cycloalkyl, $C_5$-$C_{14}$ cycloalkenyl, furyl, thienyl, pyrryl, isoxazolyl, isothiazolyl, pyrazolyl, oxazolyl, thiazolyl, imidazolyl, 1,2,3-thiadiazolyl, 1,2,4-thiadiazolyl, 1,3,4-thiadiazolyl, tetrazolyl, 1,2,3,4-thiatriazolyl, 1,2,3,4-oxatriazolyl, pyridyl, pyridazinyl, pyrimidinyl, pyrazinyl, 1,2,4-triazinyl, 1,3,5-triazinyl or 1,2,4,5-tetrazinyl group.

6. A method of controlling fungi, wherein the fungi or the material, plant or seed threatened by fungal attack or the soil are treated with a fungicidal amount of a dihydropyran of the formula (I):

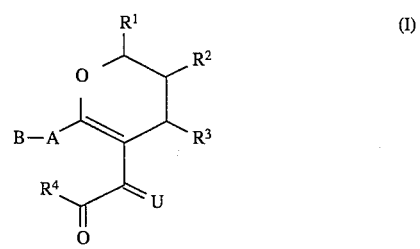

wherein:
$R^1$ is hydrogen;
$R^2$ is hydrogen;
$R^3$ is hydrogen;
$R^4$ is $OCH_3$, $OCH_2CH_3$, $NHCH_3$, $NHCH_2CH_3$, $N(CH_3)_2$, $N(CH_2CH_3)_2$, $CH_3$, or $CH_2CH_3$;
U is $CHOR^5$, $CHSR^5$, $CH_2$, $CHR^5$, CH—halogen, or N—$OR^5$,
wherein $R^5$ is methyl or ethyl;
A is a single bond $CHR^6$, $(CHR^7-CHR^6)_n$, $(CR^{21}=CR^{20})_m$—$CR^7=CR^6$, C≡C, $OCHR^6$, S—$CHR^6$, $NCH_3$—$CHR^6$, $N(CH_2CH_3)$—$CHR^6$, CO—$OCHR^6$, CH=N—O—$CHR^6$, $C(CH_3)=N$—O—$CHR^6$, or $C(CH_2CH_3)=N$—O—$CHR^6$
wherein:
$R^6$ is hydrogen, $CH_3$, or $CH_2CH_3$;
$R^7$ is hydrogen, $CH_3$, or $CH_2CH_3$;
$R^{20}$ is hydrogen, $CH_3$, or $CH_2CH_3$;
$R^{21}$ is hydrogen, $CH_3$, or $CH_2CH_3$;
n is 1, 2, or 3; and
m is 0 or 1;
B is a $C_3$-$C_{10}$-cycloalkyl, $C_5$-$C_{14}$ cycloalkenyl, phenyl, naphthyl, anthracenyl, furyl, thienyl, pyrryl, isoxazolyl, isothiazolyl, pyrazolyl, oxazolyl, thiazolyl, imidazolyl, 1,2,3-thiadiazolyl, 1,2,4-thiadiazolyl, 1,3,4-thiadiazolyl, tetrazolyl, 1,2,3,4-thiatriazolyl, 1,2,3,4-oxatriazolyl, pyridyl, pyridazinyl, pyrimidinyl, pyrazinyl, 1,2,4-triazinyl, 1,3,5-triazinyl or 1,2,4,5-tetrazinyl group, or where these groups may be substituted with from one to four of the following radicals: halogen, cyano, nitro, $C_1$-$C_4$-haloalkyl, $R^{23}$, $OR^{23}$, $=NOR^{23}$, $COOR^{23}$, $CONR^{12}R^{13}$, $SR^{23}$, $NR^{23}R^{12}$, $COR^{23}$, $SOR^{23}$, $SO_2R^{23}$ or $O-SOR^{23}$, wherein $R^{12}$ is methyl or ethyl; $R^{13}$ is methyl or ethyl; and $R^{23}$ is a $C_1$-$C_{10}$-alkyl, $C_2$-$C_{10}$-alkenyl, $C_2$-$C_{10}$-alkynyl, $C_3$-$C_{10}$-cycloalkyl, $C_5$-$C_{14}$ cycloalkenyl, furyl, thienyl, pyrryl, isoxazolyl, isothiazolyl, pyrazolyl, oxazolyl, thiazolyl, imidazolyl, 1,2,3-thiadiazolyl, 1,2,4-thiadiazolyl, 1,3,4-thiadiazolyl, tetrazolyl, 1,2,3,4-thiatriazolyl, 1,2,3,4-oxatriazolyl, pyridyl, pyridazinyl, pyrimidinyl, pyrazinyl, 1,2,4-triazinyl, 1,3,5-triazinyl or 1,2,4,5-tetrazinyl group.

* * * * *